(12) United States Patent
Khetani et al.

(10) Patent No.: US 11,407,979 B2
(45) Date of Patent: Aug. 9, 2022

(54) INTERMITTENT STARVATION TECHNIQUES TO PROLONG FUNCTIONAL LIFETIME OF LIVER CELLS IN CULTURE

(71) Applicant: Colorado State University Research Foundation, Fort Collins, CO (US)

(72) Inventors: Salman R. Khetani, Chicago, IL (US); Matthew D. Davidson, Philadelphia, PA (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 492 days.

(21) Appl. No.: 16/119,399

(22) Filed: Aug. 31, 2018

(65) Prior Publication Data
US 2019/0071638 A1    Mar. 7, 2019

Related U.S. Application Data
(60) Provisional application No. 62/553,635, filed on Sep. 1, 2017.

(51) Int. Cl.
*C12N 15/88* (2006.01)
*C12N 5/071* (2010.01)
*G01N 33/50* (2006.01)

(52) U.S. Cl.
CPC .......... *C12N 5/067* (2013.01); *G01N 33/5014* (2013.01); *G01N 33/5067* (2013.01); *C12N 2500/34* (2013.01); *C12N 2500/90* (2013.01); *C12N 2502/02* (2013.01); *C12N 2502/1323* (2013.01); *C12N 2503/00* (2013.01); *C12N 2533/54* (2013.01); *C12N 2535/00* (2013.01); *C12N 2535/10* (2013.01)

(58) Field of Classification Search
CPC ..................................................... C12N 5/067
USPC ......................................................... 435/373
See application file for complete search history.

(56) References Cited

U.S. PATENT DOCUMENTS

| | | | |
|---|---|---|---|
| 6,133,030 A * | 10/2000 | Bhatia ............... | B82Y 30/00 435/177 |
| 8,580,248 B2 | 11/2013 | Elliott et al. | |
| 8,617,815 B2 | 12/2013 | Khetani et al. | |
| 8,778,607 B2 | 7/2014 | Sokal et al. | |
| 2001/0023073 A1* | 9/2001 | Bhatia ............... | C12N 5/0697 435/373 |
| 2006/0199172 A1 | 9/2006 | Aikawa et al. | |
| 2006/0270032 A1 | 11/2006 | Bhatia et al. | |
| 2008/0233607 A1 | 9/2008 | Yu | |
| 2011/0262956 A1 | 10/2011 | Elias et al. | |
| 2011/0318730 A1 | 12/2011 | Rice et al. | |
| 2012/0111795 A1 | 5/2012 | Chamuleau et al. | |
| 2013/0164266 A1 | 6/2013 | Jensen | |
| 2013/0266939 A1 | 10/2013 | McVay et al. | |
| 2013/0309677 A1 | 11/2013 | Blackman et al. | |
| 2014/0212918 A1 | 7/2014 | Yarmush | |
| 2015/0079673 A1 | 3/2015 | Khetani et al. | |
| 2015/0240203 A1 | 8/2015 | Khetani et al. | |
| 2016/0252494 A1 | 9/2016 | Bhatia et al. | |
| 2018/0172668 A1 | 6/2018 | Khetani et al. | |
| 2018/0223253 A1 | 8/2018 | Khetani et al. | |
| 2018/0321224 A1 | 11/2018 | Khetani et al. | |

FOREIGN PATENT DOCUMENTS

| | | |
|---|---|---|
| EP | 2495310 A2 | 9/2012 |
| WO | WO 98/51785 | 11/1998 |
| WO | WO 2012/119012 A1 | 9/2012 |
| WO | WO 2015/003160 A2 | 1/2015 |

OTHER PUBLICATIONS

Bhatia et al. Effect of cell-cell interations in preservation of cellular phenotype: cocultivation of hepatocytes and nonparenchymal cells. FASEB J. Nov. 1999;13(14):1883-900.
Bi et al. Use of Cryopreserved Human Hepatocytes in Sandwich Culture to Measure Hepatobiliary Transport. Drug Metab Dispos. Sep. 2006;34(9):1658-65.
Dusabineza et al. Hepatic Stellate Cells Improve Engraftment of Human Primary Hepatocytes: A Preclinical Transplantation Study in an Animal Model. Cell Transplant. Feb. 20, 2015; vol. 24, pp. 2557-2571.
Gregory PG et al. The Effect of Coculture with Nonparenchymal Cells on Porcine Hepatocyte Function. Cell Transplantation. 2001;10:731-738.
Khetani S et al. Exploring Interactions Between Rat Hepatocytes and Nonparenchymal Cells Using Gene Expression Profiling. *Hepatology* 2004;40:545-554.
Khetani SR et al. Toxicological Sciences, Scholarone—Manuscripts: The Use of Micropatterned Co-cultures to Detect Compounds that Cause Drug Induced Liver Injury in Human. ToxSci Advance Access. Nov. 14, 2012.
Khetani SR, Bhatia SN. Microscale culture of human liver cells for drug development. *Nature Biotechnology* 2008; vol. 26, No. 1: pp. 120-126.
Lin C, Shi J, Moore A, Khetani SR. Prediction of Drug Clearance and Drug-Drug Interactions in Microscale Cultures of Human Hepatocytes. Drug Metabolism and Disposition: the biological fate of chemicals. Oct. 2015; DOI:10.1124/dmd.115.066027.
Liu et al. Hepatocyte cocultures with endothelial cells and fibroblasts on micropatterned fibrous mats to promote liver-specific functions and capillary formation capabilities. Biomacromolecules. Mar. 10, 2014; vol. 15, No. 3: 1044-1054.

(Continued)

*Primary Examiner* — Christopher M Babic
*Assistant Examiner* — Alexander W Nicol
(74) *Attorney, Agent, or Firm* — Polsinelli PC

(57) ABSTRACT

The present disclosure relates to compositions and methods for culturing a population of hepatocytes in vitro, comprising co-culturing the population of hepatocytes with at least one non-parenchymal cell population and incubating the co-culture in culture medium, wherein the co-culture is periodically incubated in culture medium that does not comprise serum (serum-free culture medium).

17 Claims, 33 Drawing Sheets
(7 of 33 Drawing Sheet(s) Filed in Color)

(56) References Cited

OTHER PUBLICATIONS

March S et al. Micropatterned coculture of primary human hepatocytes and supportive cells for the study of hepatotropic pathogens. *Nature Protocols* 2015; vol. 10, No. 12: 2027-2053.

March S, Hui EE, Underhill GH, Khetani S, Bhatia SN. Microenvironmental Regulation of the Sinusoidal Endothelial Cell Phenotype in vitro. Hepatology. Sep. 2009; 50(3):920-928.

Morin O, Normand C. Long-Term Maintenance of Hepatocyte Functional Activity in Co-Culture: Requirements for Sinusoidal Endothelial Cells and Dexamethasone. Journal of Cellular Physiology. 1986;129(1):103-110.

Nagamoto et al. The promotion of hepatic maturation of human pluripotent stem cells in 3D co-culture using type I collagen and Swiss 3T3 cell sheets. Biomaterials, Jun. 2012;33(18):4526-34.

Nahmias Y et al. Endothelium-Mediated Hepatocyte Recruitment in the Establishment of Liver-Like Tissue in vitro. Tissue Engineering. vol. 12, No. 6, Jul. 19, 2006, pp. 1627-1638.

Wang WW, Khetani SR, Krzyzewski S, Duignan DB, Obach RS. Assessment of a Micropatterned Hepatocyte Coculture System to Generate Major Human Excretory and Circulating Drug Metabolites. Drug Metabolism and Disposition. Oct. 2010; DOI: 10.1124/dmd.110.034876.

Ware et al. A Cell Culture Platform to Maintain Long-Term Phenotype of Primary Human Hepatocytes and Endothelial Cells. *Cellular and Molecular Gastroenterology and Hepatology* 2017;vol. 5, No. 3:187-207.

Westlind-Johnsson, et al.,Comparative analysis of CYP3A expression in human liver suggests only a minor role for CYP3A5 in drug metabolism, Drug Metab Dispos. Jun. 2003;31(6):755-61.

Yu, B. Effects of Metformin On Glucose and Glucagon Regulated Gluconeogenesis In Cultured Normal and Diabetic Hepatocytes, Biochem Pharm. 1994; vol. 48, No. 5, pp. 949-954.

Zinchenko YS et al. Contribution of Non-parenchymal Cells to the Performance of Micropatterned Hepatocytes. Tissue Engineering. 2006;12(8):2241-2251.

Zinchenko YS et al. Hepatocyte and Kupffer Cells Co-cultured on Micropatterned Surfaces to Optimize Hepatocyte Function. Tissue Engineering. 2006;12(4):751-761.

Kostadinova R et al. A long-term three dimensional liver co-culture system for improved prediction of clinically relevant drug-induced hepatotoxicity. Toxicology and Applied Pharmacology, 268 (2013) 1-16.

Mittal N et al. Complex Interplay between Serum and Fibroblasts in 3D Hepatocyte Co-culture. bioRxiv, Mar. 22, 2018. Retrieved from internet: https://www.biorxiv.org/content/biorxiv/early/2018/03/22/286088.full.pdf.

Torisawa et al. Transwells with Microstamped Membranes Produce Micropatterned Two-Dimensional and Three-Dimensional Co-Cultures. Tissue Engineering, Part C, vol. 17, No. 1, 2011.

Ware BR, Berger DR, Khetani SR. Prediction of Drug-Induced Liver Injury in Micropatterned Co-cultures Containing iPSC-Derived Human Hepatocytes. Toxicological Sciences, 2015, 1-11.

Hughes et al. Matrigel: A complex protein mixture required for optimal growth of cell culture. Proteomics Jan. 2010, 10, 1886-1890.

March et al. Supplemental Material: Microenvironmental Regulation of the Sinusoidal Endothelial Cell Phenotype in vitro. Hepatology. Sep. 2009; 50(3):920-928.

Hino H et al. A Long-Term Culture of Human Hepatocytes which Show a High Growth Potential and Express Their Differentiated Phenotypes. Biochemical and Biophysical Research Communications 256 (1999) 184-191.

Salerno S, Campana C, Morelli S, Drioli E, De Bartolo L. Human hepatocytes and endothelial cells in organotypic membrane systems. Biomaterials 32 (2011) 8848-8859.

\* cited by examiner

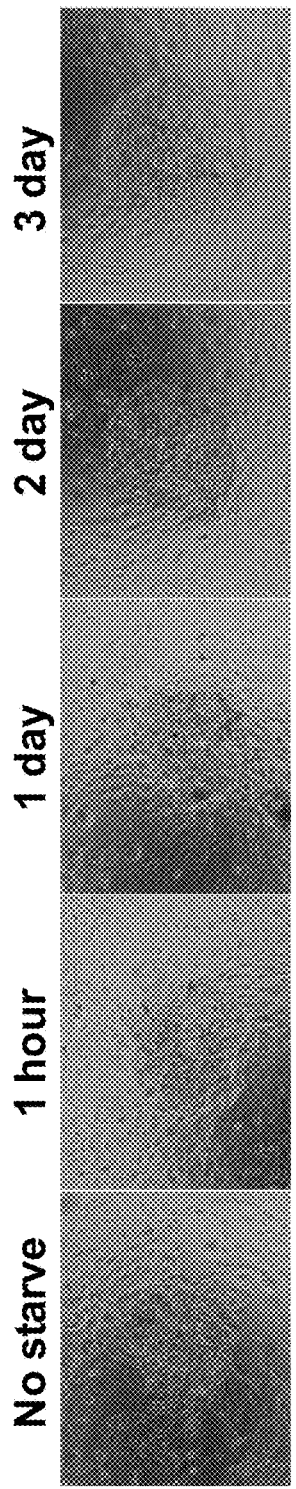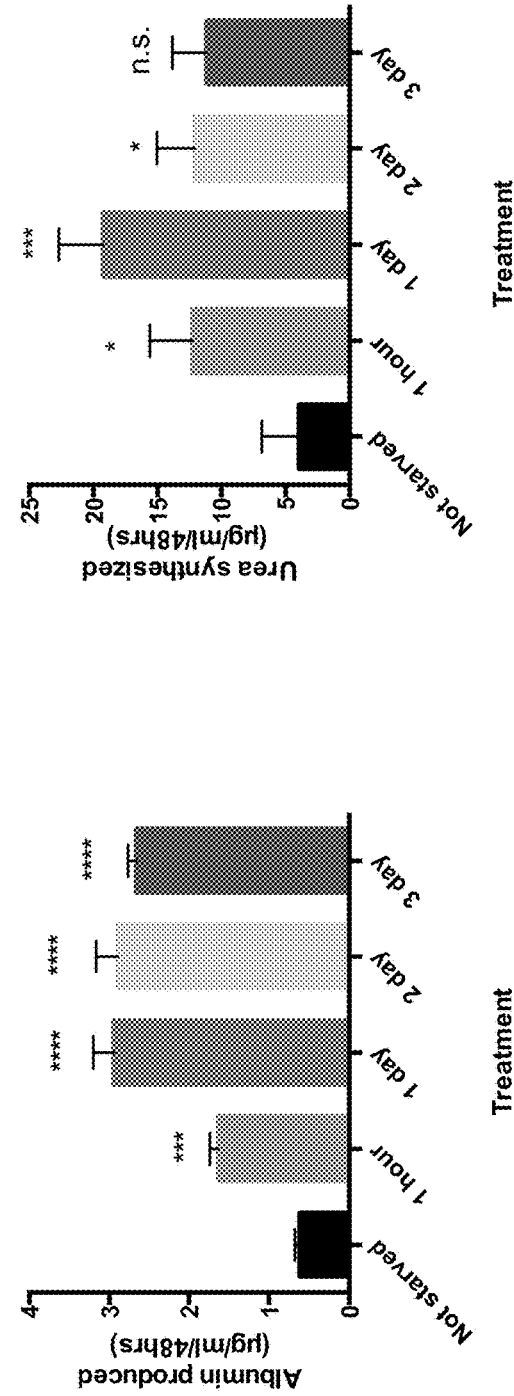

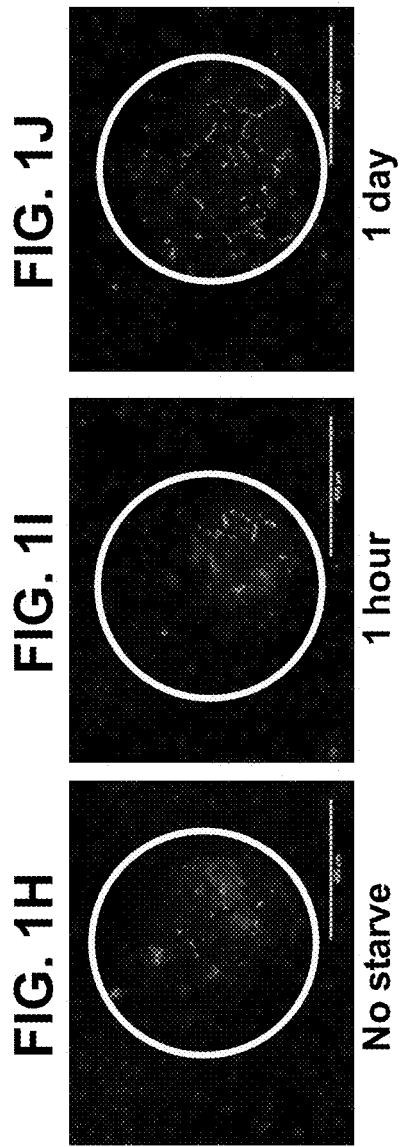
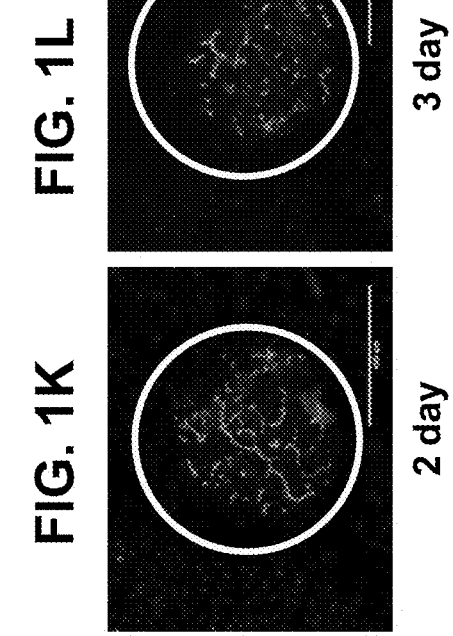

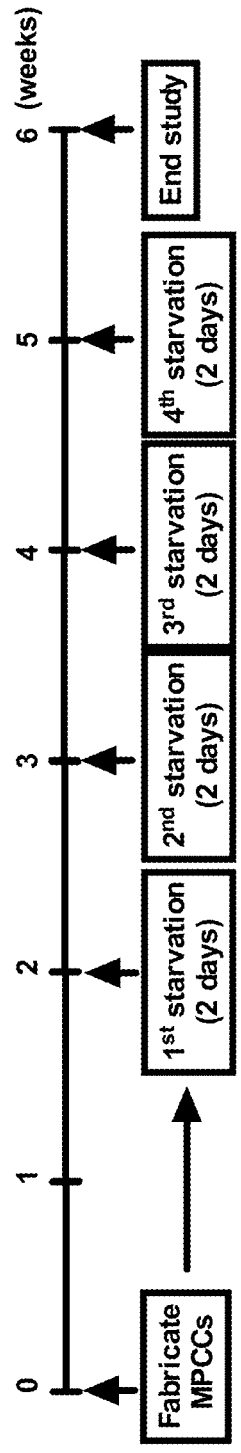
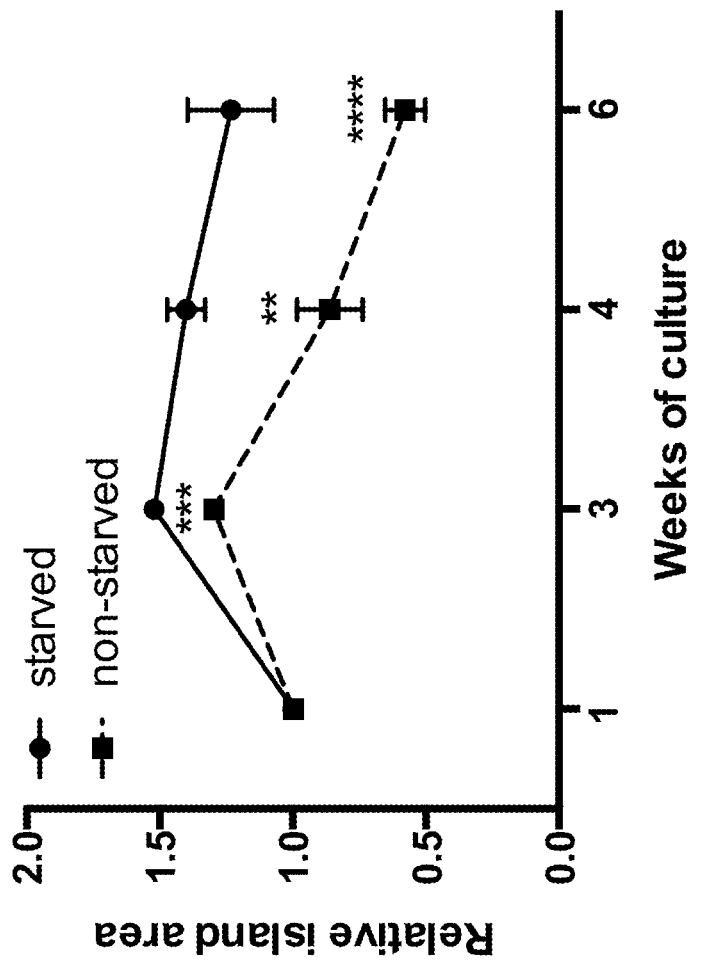
FIG. 3A
FIG. 3B

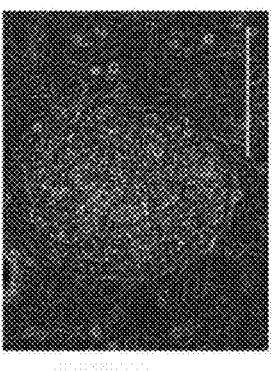
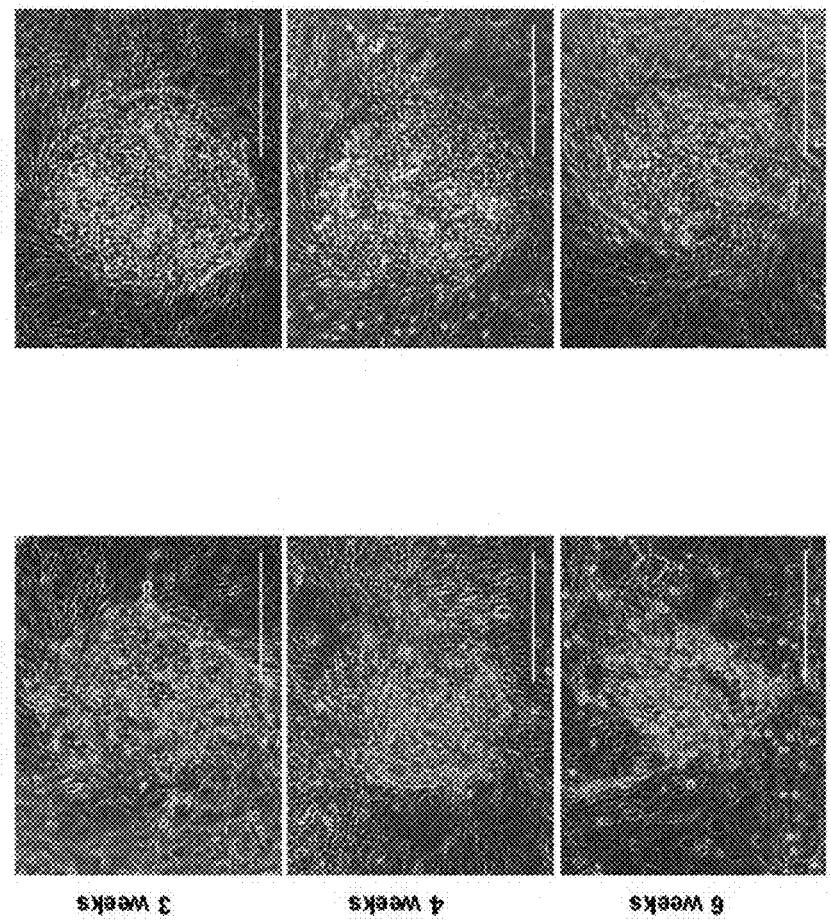
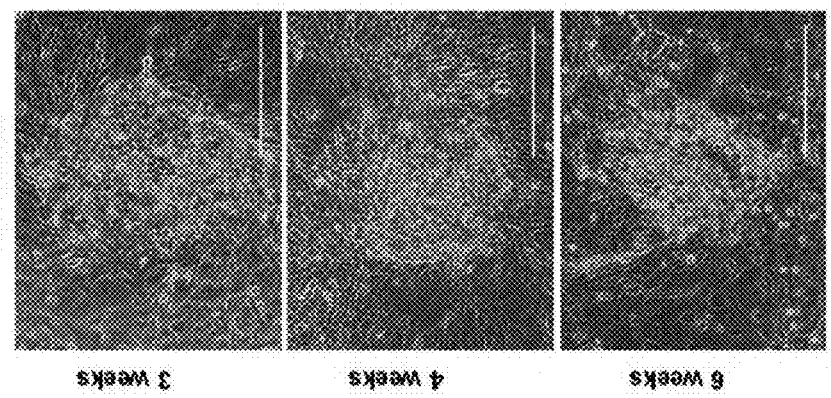
FIG. 3C
FIG. 3D
FIG. 3E
FIG. 3F
FIG. 3G
FIG. 3H
FIG. 3I

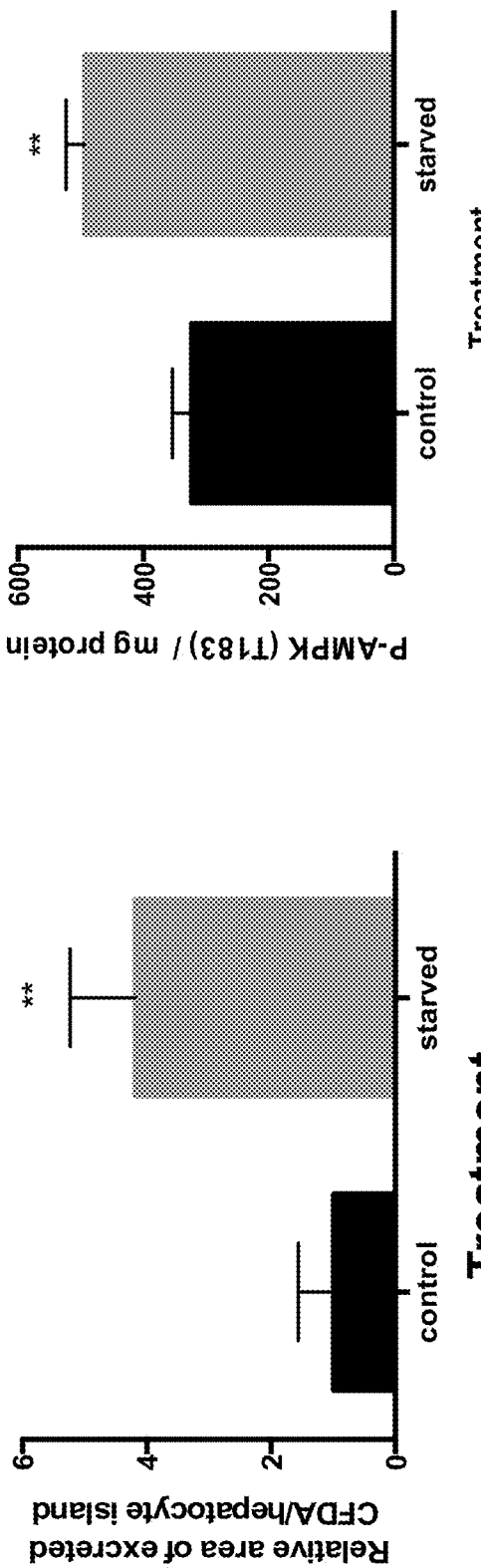
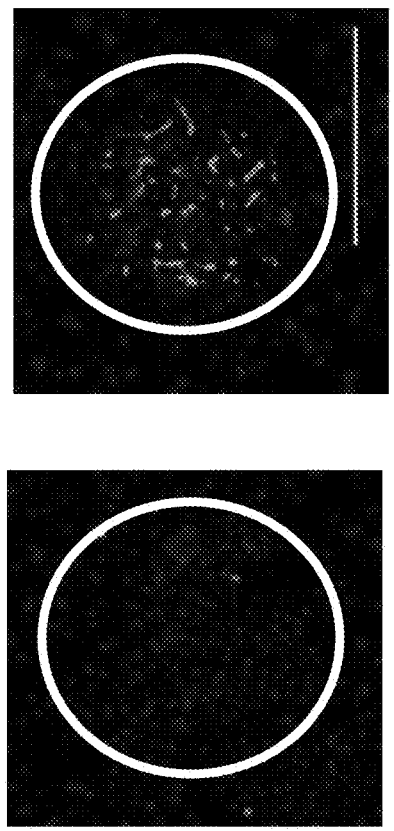
FIG. 4D
FIG. 4E
FIG. 4F
FIG. 4G

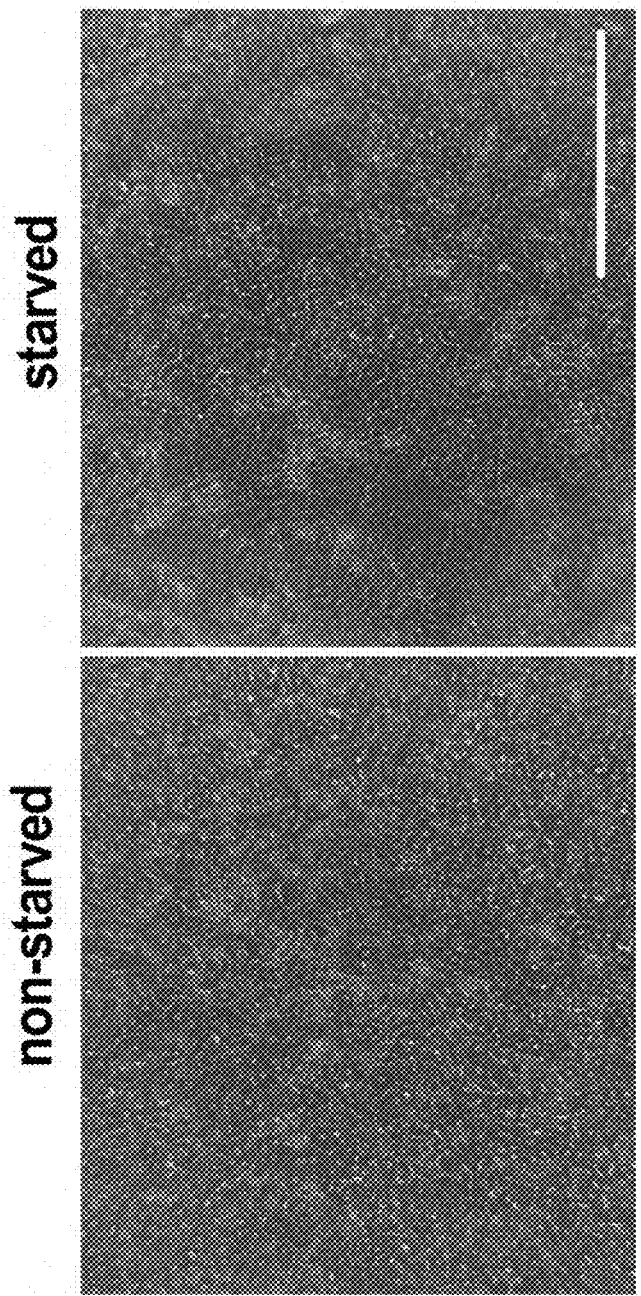

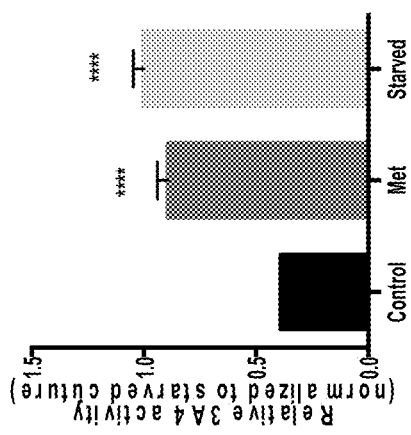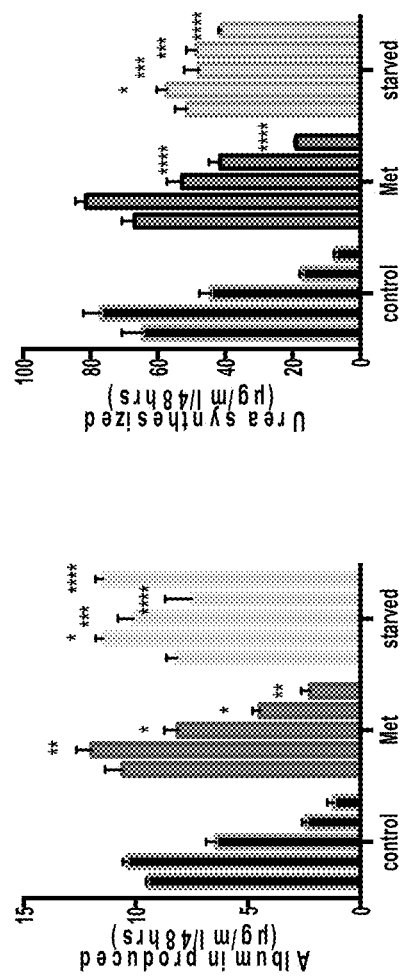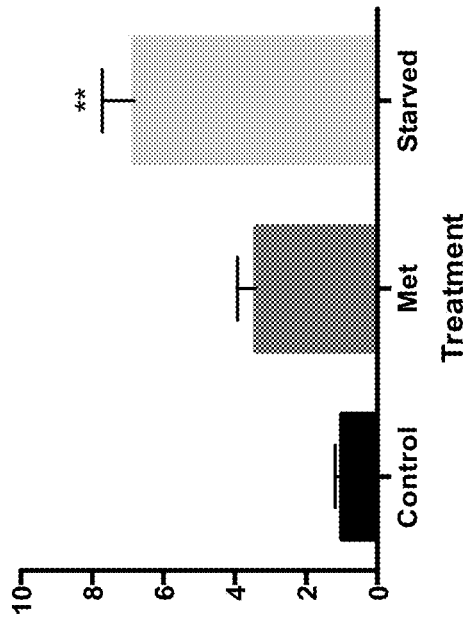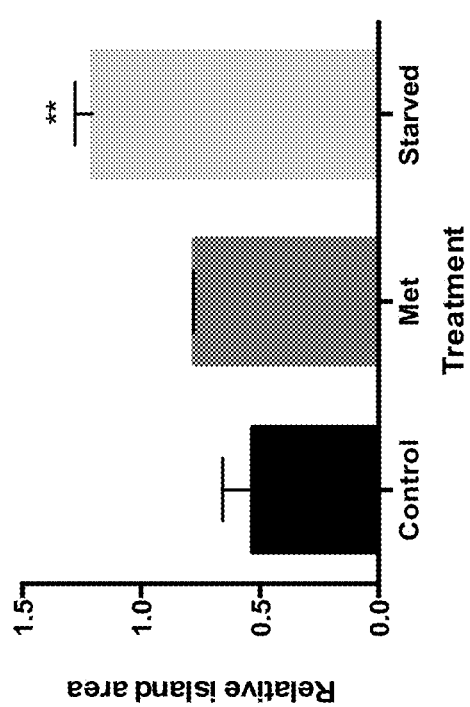
FIG. 7A, FIG. 7B, FIG. 7C, FIG. 7D, FIG. 7E

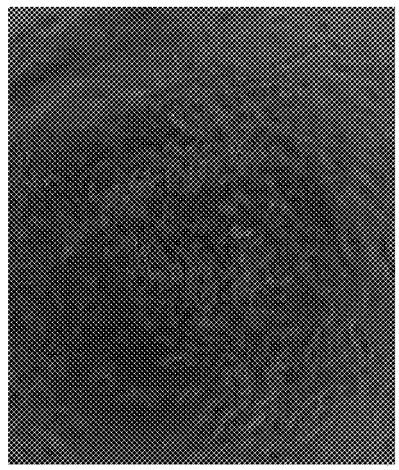
FIG. 7F control
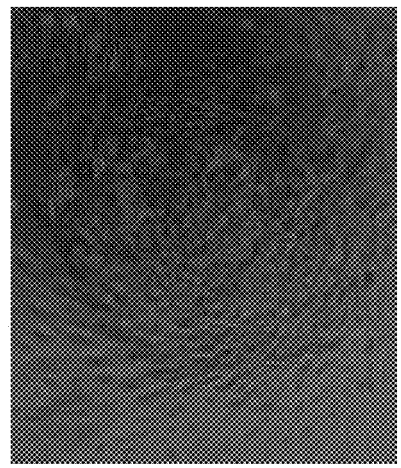
FIG. 7G Met
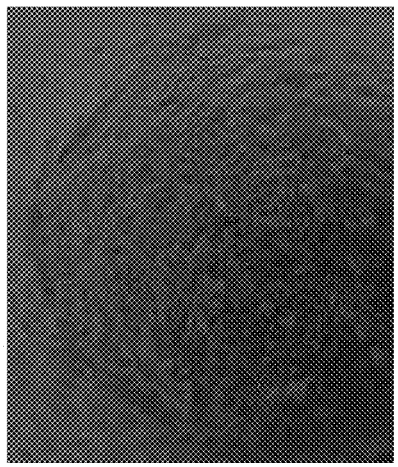
FIG. 7H starved
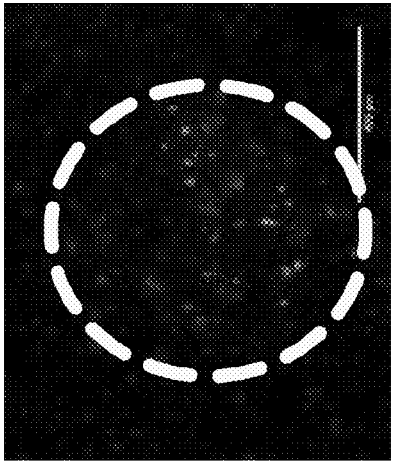
FIG. 7I control
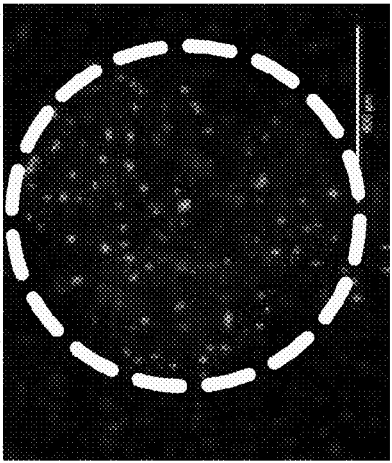
FIG. 7J Met
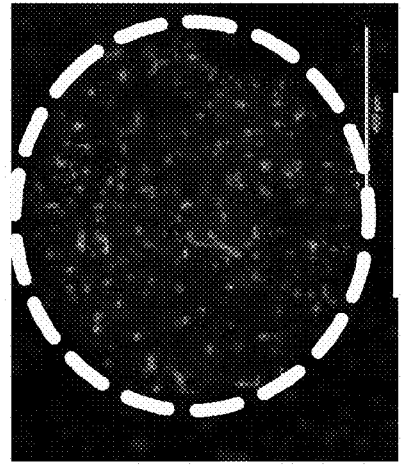
FIG. 7K starved

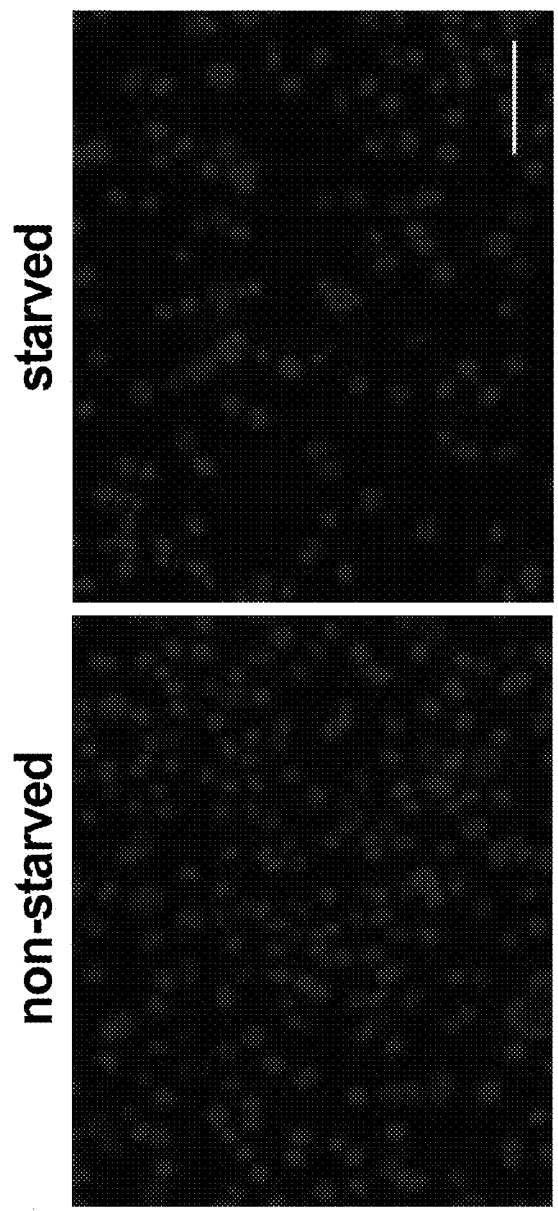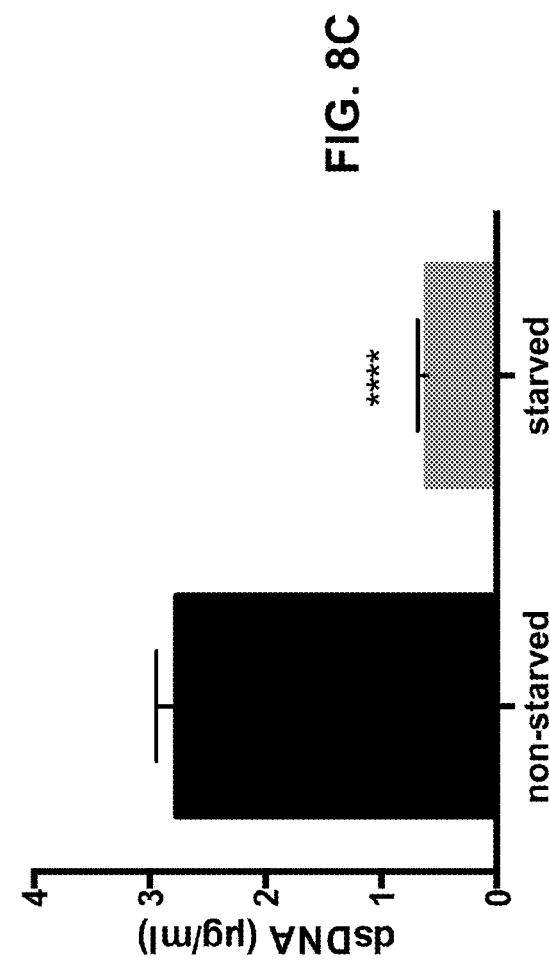

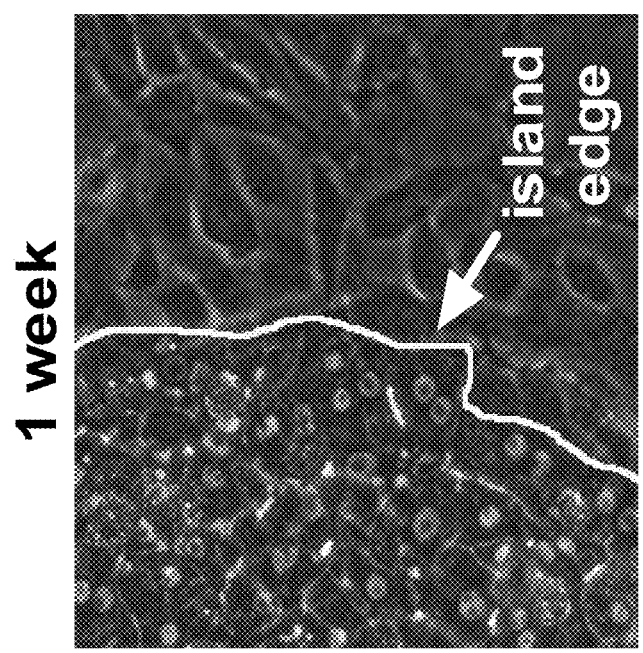

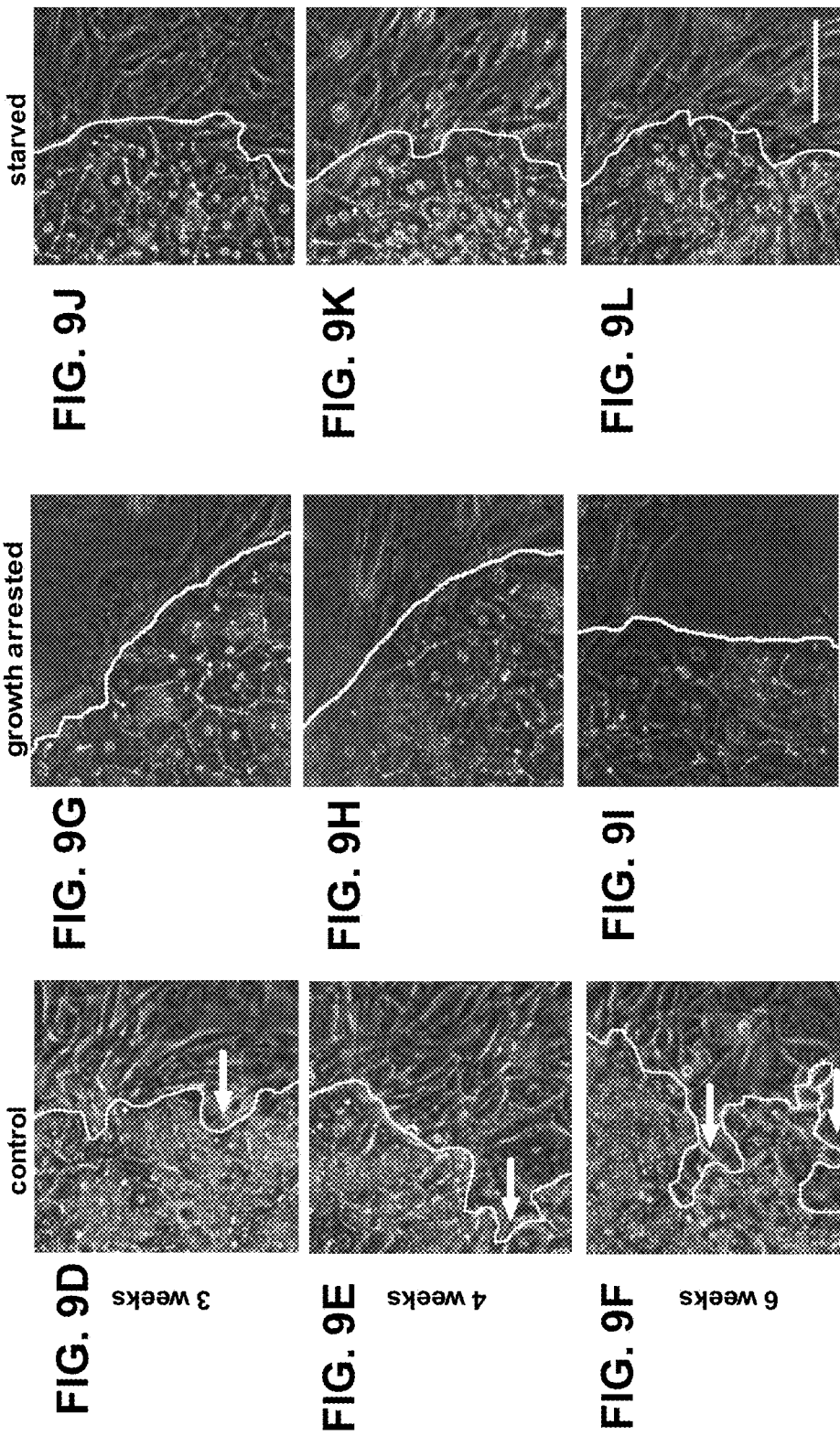

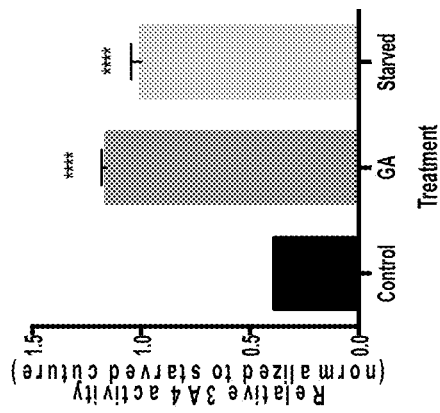
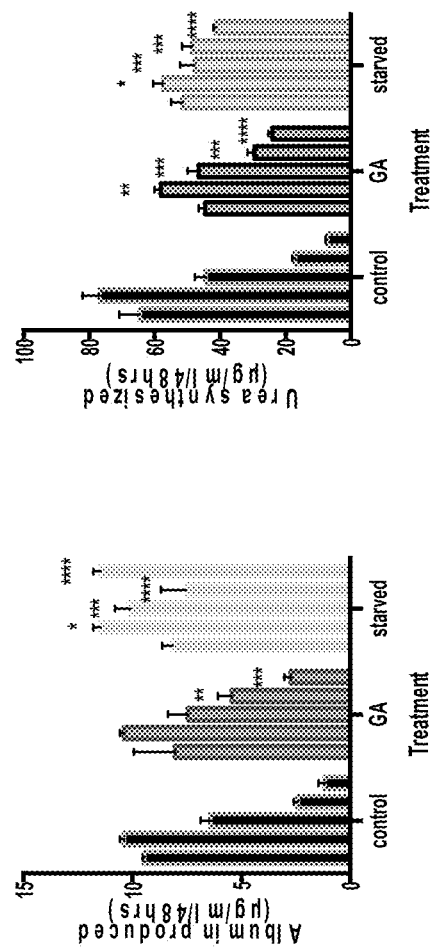
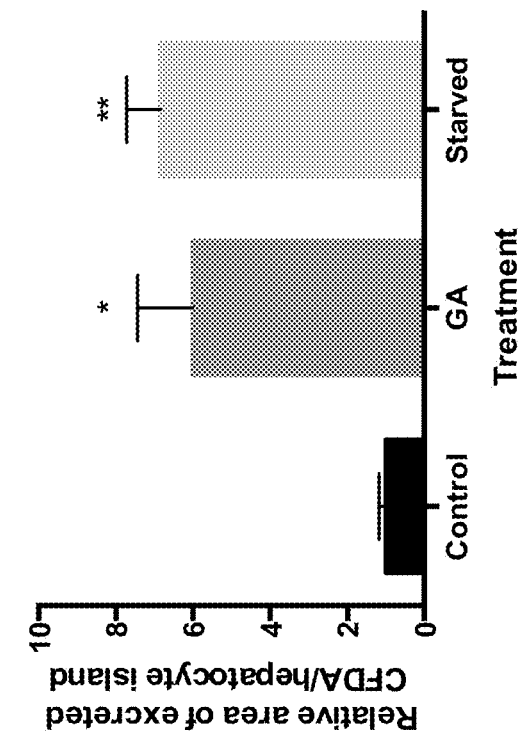
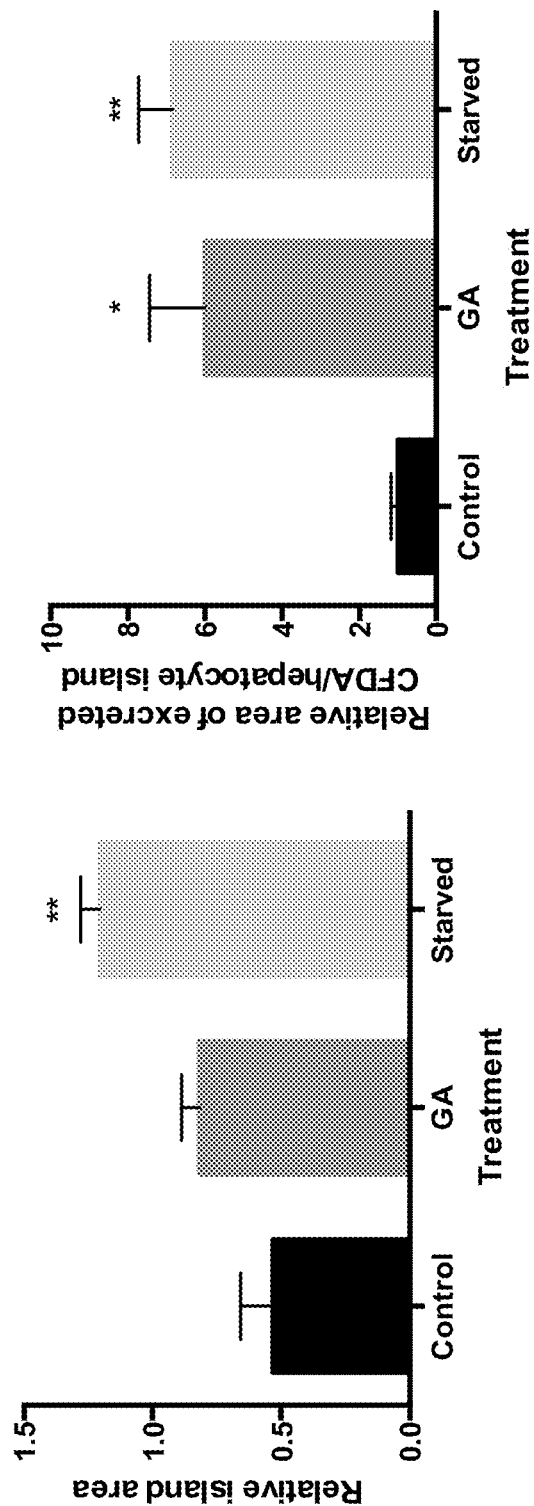

INTERMITTENT STARVATION TECHNIQUES TO PROLONG FUNCTIONAL LIFETIME OF LIVER CELLS IN CULTURE

CROSS REFERENCE TO RELATED APPLICATIONS

This application claims the benefit of U.S. Provisional Application No. 62/553,635, filed Sep. 1, 2017, the disclosures of which is hereby incorporated by reference in its entirety.

GOVERNMENTAL RIGHTS

This invention was made with government support under CBET -1351909 awarded by the National Science Foundation. The government has certain rights in the invention.

FIELD OF THE INVENTION

The present disclosure relates to compositions and methods for culturing a population of hepatocytes in vitro, comprising co-culturing the population of hepatocytes with at least one non-parenchymal cell population and incubating the co-culture in culture medium, wherein the co-culture is incubated in culture medium comprising serum for at least one time period of about 1 hour to about 6 weeks and is incubated in culture medium that does not comprise serum (serum-free culture medium) for at least one time period of about 1 hour to about 6 weeks.

BACKGROUND OF THE INVENTION

Hepatocytes, the main cell type of the liver, rapidly lose their phenotypic functions under conventional culture formats that rely exclusively on extracellular matrices (ECM). Co-culture of hepatocytes with stromal cells from both within and outside the liver in either 2-dimensional or 3-dimensional configurations can prolong hepatic phenotype to ~4 weeks in vitro. The lifetime of a hepatocyte in vivo is around 150 days; however, no current culture platform can keep hepatocytes highly functional for that length of time. The culture medium plays an important role in hepatocyte survival in any culture configuration; however, most models do not maintain hepatic functions past 3-4 weeks of co-culture in current media formulations. There is a need in the art for improving the culture media formulation and timed administration of culture media to further prolong the lifetime of hepatocytes in vitro. Such a medium can result in hepatocyte cultures that have applications in testing the effects of chronically administered drugs and diseases that affect the liver, such as hepatitis, type 2 diabetes, malaria, liver fibrosis, liver cancer and fatty liver disease.

SUMMARY OF THE INVENTION

In an aspect, the disclosure provides a method of culturing a population of hepatocytes in vitro, comprising co-culturing the population of hepatocytes with at least one non-parenchymal cell population and incubating the co-culture in culture medium, wherein the cell populations are disposed in a micropattern on a culture substrate and the micropattern comprises a predetermined two-dimensional pattern of multiple microdots, the micropattern defined by a microdot diameter and a center-to-center spacing between each of any two neighboring microdots, and the microdots comprise the hepatocytes and the space between the microdots comprises the non-parenchymal cell population, and wherein the co-culture is incubated in culture medium comprising serum for at least one time period of about 1 hour to about 6 weeks and is incubated in culture medium that does not comprise serum (serum-free culture medium) for at least one time period of about 1 hour to about 6 weeks. Each microdot can have a diameter of about 500 µm and the center-to-center spacing between each of any two neighboring microdots is about 1200 µm. The co-culture can be incubated in culture medium comprising serum for at least one time period of at least 1 week before the composition is incubated in serum-free culture medium. The co-culture can be incubated in culture medium comprising serum for at least one time period of at least 2 weeks before the composition is incubated in serum-free culture medium. The co-culture can be incubated in serum-free culture medium for at least one time period of about 1 hour to about 3 days. The co-culture can be incubated serum-free culture medium for at least one time period of about 2 days. Specifically, the co-culture can be (a) incubated in serum-free culture medium for a time period of about 1 hour to about 3 days and (b) incubated in culture medium comprising serum for a time period of about 5 to about 8 days, wherein (a) and (b) are alternated for up to 6 weeks.

The co-culture can exhibit at least one indicator of hepatocyte function at least 4 weeks in culture. The co-culture can exhibit at least one indicator of hepatocyte function at least 6 weeks in culture. The at least one indicator of hepatocyte function can be selected from albumin production, urea production, ATP production, glutathione production, enzyme activity, lipid accumulation, liver gene expression, liver protein expression, or CYP2C9 activity, CYP3A4 activity, CYP1A1 activity, CYP1A2 activity, CYP2B6 activity, CYP2A6 activity, CYP2D6 activity, CYP2C8 activity, CYP2C19 activity, or CYP2E1 activity.

The co-culture can retain hepatocyte morphology at least 4 weeks in culture. The co-culture can retain hepatocyte morphology at least 6 weeks in culture.

The serum-free culture medium can comprise glucose. The serum-free culture medium can comprise glucagon.

The co-culture of a population of hepatocytes with at least one non-parenchymal cell population can compromise human hepatocytes. The co-culture of a population of hepatocytes with at least one non-parenchymal cell population can compromise primary human hepatocytes.

The co-culture of a population of hepatocytes with at least one non-parenchymal cell population wherein at least one of the non-parenchymal cell populations can comprise non-human stromal cells. The non-human stromal cells can be selected from the group consisting of fibroblasts, fibroblast-derived cells, macrophages, endothelial cells, stellate cells, pericytes, inflammatory cells, cholangiocytes and other types of stromal cells, and combinations thereof. The co-culture of a population of hepatocytes with at least one non-parenchymal cell population can further compromise murine embryonic fibroblasts. Specifically, the co-culture of a population of hepatocytes with at least one non-parenchymal cell population can further compromise 3T3-J2 murine embryonic fibroblasts. The co-culture of a population of hepatocytes with at least one non-parenchymal cell population can further compromise growth arrested stromal cells. The co-culture of a population of hepatocytes with at least one non-parenchymal cell population can further compromise stromal cells that are not growth arrested.

In another aspect, the disclosure provides a composition comprising a population of hepatocytes in vitro, comprising co-culturing the population of hepatocytes with at least one non-parenchymal cell population and incubating the co-culture in culture medium, wherein the cell populations are disposed in a micropattern on a culture substrate and the micropattern comprises a predetermined two-dimensional pattern of multiple microdots, the micropattern defined by a microdot diameter and a center-to-center spacing between each of any two neighboring microdots, and the microdots comprise the hepatocytes and the space between the microdots comprises the non-parenchymal cell population, and wherein the co-culture is incubated in culture medium comprising serum for at least one time period of about 1 hour to about 6 weeks and is incubated in culture medium that does not comprise serum (serum-free culture medium) for at least one time period of about 1 hour to about 6 weeks. Each microdot can have a diameter of about 500 µm and the center-to-center spacing between each of any two neighboring microdots is about 1200 µm. The co-culture can be incubated in culture medium comprising serum for at least one time period of at least 1 week before the composition is incubated in serum-free culture medium. The co-culture can be incubated in culture medium comprising serum for at least one time period of at least 2 weeks before the composition is incubated in serum-free culture medium. The co-culture can be incubated in serum-free culture medium for at least one time period of about 1 hour to about 3 days. The co-culture can be incubated serum-free culture medium for at least one time period of about 2 days. Specifically, the co-culture can be (a) incubated in serum-free culture medium for a time period of about 1 hour to about 3 days and (b) incubated in culture medium comprising serum for a time period of about 5 to about 8 days, wherein (a) and (b) are alternated for up to 6 weeks.

The co-culture can exhibit at least one indicator of hepatocyte function at least 4 weeks in culture. The co-culture can exhibit at least one indicator of hepatocyte function at least 6 weeks in culture. The least one indicator of hepatocyte function can be selected from albumin production, urea production, ATP production, glutathione production, enzyme activity, lipid accumulation, liver gene expression, liver protein expression, or CYP2C9 activity, CYP3A4 activity, CYP1A1 activity, CYP1A2 activity, CYP2B6 activity, CYP2A6 activity, CYP2D6 activity, CYP2C8 activity, CYP2C19 activity, or CYP2E1 activity.

The co-culture can retain hepatocyte morphology at least 4 weeks in culture. The co-culture can retain hepatocyte morphology at least 6 weeks in culture.

The co-culture of a population of hepatocytes with at least one non-parenchymal cell population can compromise human hepatocytes. The co-culture of a population of hepatocytes with at least one non-parenchymal cell population can compromise primary human hepatocytes.

The co-culture of a population of hepatocytes with at least one non-parenchymal cell population wherein at least one of the non-parenchymal cell populations can comprise non-human stromal cells. The non-human stromal cells can be selected from fibroblasts, fibroblast-derived cells, macrophages, endothelial cells, stellate cells, pericytes, inflammatory cells, cholangiocytes and other types of stromal cells, and combinations thereof. The co-culture of a population of hepatocytes with at least one non-parenchymal cell population can further compromise murine embryonic fibroblasts. Specifically, the co-culture of a population of hepatocytes with at least one non-parenchymal cell population can further compromise 3T3-J2 murine embryonic fibroblasts. The co-culture of a population of hepatocytes with at least one non-parenchymal cell population can further compromise growth arrested stromal cells. The co-culture of a population of hepatocytes with at least one non-parenchymal cell population can further compromise stromal cells that are not growth arrested.

In still another aspect, the disclosure provides a method of identifying a candidate test compound for use in treating a disorder of the liver, the method comprising: contacting a composition of the disclosure with the test compound; maintaining the composition for a time and under conditions sufficient to allow an effect of the test compound on the hepatocytes; measuring at least one indicator of hepatic function in the hepatocytes to obtain a test measurement, or applying hepatocyte imaging technology (HIAT) to the hepatocytes to obtain a test image; and comparing the test measurement to a control measurement from the hepatocytes before contact with the test compound, or the test image to a control image of the hepatocytes before contact with the test compound, wherein a difference between the test and control is indicative of whether the test compound is a candidate for use in treating a disorder of the liver. The at least one indicator of hepatic function can be selected from the group consisting of albumin production, urea production, ATP production, glutathione production, enzyme activity, lipid accumulation, liver gene expression, and liver protein expression in the hepatocytes. The at least one inducible liver enzyme can be selected from CYP2C9, CYP3A4, a combination of CYP1A1, CYP1A2, CYP2B6, CPY2A6, and CYP2D6, and any combination thereof.

BRIEF DESCRIPTION OF THE FIGURES

The application file contains at least one drawing executed in color. Copies of this patent application publication with color drawing(s) will be provided by the Office upon request and payment of the necessary fee.

FIGS. 1A-1E depict images of co-cultures comprising hepatocytes and non-parenchymal cell populations wherein the composition is periodically incubated in serum-free culture medium for 1 hour (FIG. 1B), 1 day (FIG. 1C), 2 days (FIG. 1D), or 3 days (FIG. 1E) and a co-culture comprising hepatocytes and non-parenchymal cell populations continually cultured in culture medium comprising serum (not starved) (FIG. 1A).

FIG. 1F depicts a graph showing the amount of albumin produced by co-cultures comprising hepatocytes and non-parenchymal cell populations wherein the composition is periodically incubated in serum-free culture medium for 1 hour, 1 day, 2 days, or 3 days and a co-culture comprising hepatocytes and non-parenchymal cell populations continually cultured in culture medium comprising serum (not starved). Error bars represent SD where *, *, and ** represent $p<0.05$, $p<0.001$ and $<0.0001$, respectively, assessed via one-way ANOVA between treatments.

FIG. 1G depicts a graph showing the amount of urea produced by co-cultures comprising hepatocytes and non-parenchymal cell populations wherein the composition is periodically incubated in serum-free culture medium for 1 hour, 1 day, 2 days, or 3 days and a co-culture comprising hepatocytes and non-parenchymal cell populations continually cultured in culture medium comprising serum (not starved). Error bars represent SD where *, *, and ** represent $p<0.05$, $p<0.001$ and $<0.0001$, respectively, assessed via one-way ANOVA between treatments.

FIGS. 1H-1L depicts images of co-cultures comprising hepatocytes and non-parenchymal cell populations wherein the composition is periodically incubated in serum-free culture medium for 1 hour (FIG. 1I), 1 day (FIG. 1J), 2 days (FIG. 1K), or 3 days (FIG. 1L) and a co-culture comprising hepatocytes and non-parenchymal cell populations continually cultured in culture medium comprising serum (not starved) (FIG. 1H) wherein bile canaliculi was assessed using CDCFDA fluorescent staining (green) and Hoechst 33342 (blue) to visualize cell nuclei. Circles outline hepatocyte islands and scale bars represent 400 μm.

FIG. 3A depicts a schematic of the timeline used to periodically serum-starve micropatterned co-cultures ("MPCCs") comprising hepatocytes and non-parenchymal cell populations.

FIG. 3B depicts a graph showing the relative area of hepatocyte islands (n=3-6 islands; normalized to 1 week area) in co-cultures comprising hepatocytes and non-parenchymal cell populations wherein the composition is periodically incubated in serum-free culture medium and a co-culture comprising hepatocytes and non-parenchymal cell populations continually cultured in culture medium comprising serum (non-starved) over 6 weeks of culture. Error bars represent SEM where , *, and **** represent $p<0.01$, $p<0.001$ and $<0.0001$, respectively, assessed via t-test between non-starved and starved cultures.

FIGS. 3C-3I depict images of co-cultures comprising hepatocytes and non-parenchymal cell populations at one week (FIG. 3C) and thereafter wherein after one week the composition is periodically incubated in serum-free culture medium (starved) at 3 (FIG. 3G), 4 (FIG. 3H), and 6 (FIG. 3I) weeks of culture or the co-cultures comprising hepatocytes and non-parenchymal cell populations are continually cultured in culture medium comprising serum (non-starved) at 3 (FIG. 3D), 4 (FIG. 3E), and 6 (FIG. 3F) weeks of culture. Scale bars represent 400 μm.

FIG. 4D depicts a graph showing the relative area of secreted CDF (bile canaliculi) from co-cultures comprising hepatocytes and non-parenchymal cell populations, normalized to control cell cultures, wherein the composition is periodically incubated in serum-free culture medium and co-cultures comprising hepatocytes and non-parenchymal cell populations continually cultured in culture medium comprising serum (non-starved) over 40 days of culture. Error bars represent SEM where , *, and **** represent $p<0.01$, $p<0.001$ and $<0.0001$, respectively, assessed via t-test between non-starved and starved cultures.

FIGS. 4E-F depict images of co-cultures comprising hepatocytes and non-parenchymal cell populations wherein the composition is periodically incubated in serum-free culture medium for 40 days (starved) (FIG. 4F) and a co-culture comprising hepatocytes and non-parenchymal cell populations continually cultured in culture medium comprising serum (not starved) (FIG. 4E) wherein bile canaliculi was assessed using CDCFDA fluorescent staining (green) and Hoechst 33342 (blue) to visualize cell nuclei. Circles outline hepatocyte islands and scale bars represent 400 μm.

FIG. 4G depicts a graph showing the amount of phosphorylated adenosine monophosphate activated kinase (p-AMPK) in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) at 6 weeks of culture. Error bars represent SEM where , *, and **** represent $p<0.01$, $p<0.001$ and $<0.0001$, respectively, assessed via t-test between non-starved and starved cultures.

FIGS. 6A-6B depicts images of MPCCs comprising hepatocytes wherein the composition is periodically incubated in serum-free culture medium every two days for 2 weeks (FIG. 6B) and MPCCs comprising hepatocytes continually cultured in culture medium comprising serum (non-starved) (FIG. 6A) after 14 days of culture. Scale bars represent 400 µm.

FIG. 7A depicts a graph showing the amount of albumin produced in co-cultures comprising hepatocytes and non-parenchymal cell populations wherein the composition is periodically incubated in serum-free culture medium (starved), co-cultures comprising hepatocytes and non-parenchymal cell populations wherein the composition is periodically incubated in serum-free culture medium in the presence of metformin (met), and co-cultures comprising hepatocytes and non-parenchymal cell populations continually cultured in culture medium comprising serum (control) after 4 weeks of culture. Error bars represent SEM where , *, and **** represent $p<0.01$, $p<0.001$ and $<0.0001$, respectively, assessed via one-way ANOVA between treatments.

FIG. 7B depicts a graph showing the amount of urea produced in co-cultures comprising hepatocytes and non-parenchymal cell populations wherein the composition is periodically incubated in serum-free culture medium (starved), co-cultures comprising hepatocytes and non-parenchymal cell populations wherein the composition is periodically incubated in serum-free culture medium in the presence of metformin (met), and co-cultures comprising hepatocytes and non-parenchymal cell populations continually cultured in culture medium comprising serum (control) after 4 weeks of culture. Error bars represent SEM where , *, and **** represent $p<0.01$, $p<0.001$ and $<0.0001$, respectively, assessed via one-way ANOVA between treatments.

FIG. 7C depicts a graph showing the amount of CYP3A4 activity in co-cultures comprising hepatocytes and non-parenchymal cell populations wherein the composition is periodically incubated in serum-free culture medium (starved), co-cultures comprising hepatocytes and non-parenchymal cell populations wherein the composition is periodically incubated in serum-free culture medium in the presence of metformin (met), and co-cultures comprising hepatocytes and non-parenchymal cell populations continually cultured in culture medium comprising serum (control) after 4 weeks of culture. Error bars represent SEM where , *, and **** represent $p<0.01$, $p<0.001$ and $<0.0001$, respectively, assessed via one-way ANOVA between treatments.

FIG. 7D depicts a graph showing the hepatocyte island area of co-cultures comprising hepatocytes and non-parenchymal cell populations wherein the composition is periodically incubated in serum-free culture medium (starved), co-cultures comprising hepatocytes and non-parenchymal cell populations wherein the composition is periodically incubated in serum-free culture medium in the presence of metformin (met), and co-cultures comprising hepatocytes and non-parenchymal cell populations continually cultured in culture medium comprising serum (control) after 4 weeks of culture. Error bars represent SEM where , *, and **** represent $p<0.01$, $p<0.001$ and $<0.0001$, respectively, assessed via one-way ANOVA between treatments.

FIG. 7E depicts a graph showing the amount of CDCFDA excreted from co-cultures comprising hepatocytes and non-parenchymal cell populations wherein the composition is periodically incubated in serum-free culture medium (starved), co-cultures comprising hepatocytes and non-parenchymal cell populations wherein the composition is periodically incubated in serum-free culture medium in the presence of metformin (met), and co-cultures comprising hepatocytes and non-parenchymal cell populations continually cultured in culture medium comprising serum (control) after 4 weeks of culture. Error bars represent SEM where , *, and **** represent $p<0.01$, $p<0.001$ and $<0.0001$, respectively, assessed via one-way ANOVA between treatments.

FIGS. 7F-7H depicts images of co-cultures comprising hepatocytes wherein the composition is periodically incubated in serum-free culture medium (starved) (FIG. 7H), co-cultures comprising hepatocytes and non-parenchymal cell populations wherein the composition is periodically incubated in serum-free culture medium in the presence of metformin (met) (FIG. 7G), and co-cultures comprising hepatocytes and non-parenchymal cell populations continually cultured in culture medium comprising serum (control) (FIG. 7F) after 6 weeks of culture. Scale bars represent 400 µm.

FIGS. 7I-7K depicts images of co-cultures comprising hepatocytes wherein the composition is periodically incubated in serum-free culture medium (starved) (FIG. 7K), co-cultures comprising hepatocytes and non-parenchymal cell populations wherein the composition is periodically incubated in serum-free culture medium in the presence of metformin (met) (FIG. 7J), and co-cultures comprising hepatocytes and non-parenchymal cell populations continually cultured in culture medium comprising serum (control) (FIG. 7I) after 6 weeks of culture wherein bile canaliculi was assessed using CDCFDA fluorescent staining (green) and Hoechst 33342 (blue) to visualize cell nuclei. Circles outline hepatocyte islands and scale bars represent 400 µm.

FIGS. 8A-8B depict images displaying the amount of DNA (blue) in the non-parenchymal cells (fibroblasts) from co-cultures comprising hepatocytes and non-parenchymal cell populations wherein the composition is periodically incubated in serum-free culture medium (starved) (FIG. 8B) and in the non-parenchymal cells (fibroblasts) from co-cultures comprising hepatocytes and non-parenchymal cell populations continually cultured in culture medium comprising serum (non-starved) (FIG. 8A) after 4 weeks of culture. Scale bar represents 100 µm.

FIG. 8C depicts a graph showing the amount of DNA in the non-parenchymal cells (fibroblasts) from co-cultures comprising hepatocytes and non-parenchymal cell populations wherein the composition is periodically incubated in serum-free culture medium (starved) and in the non-parenchymal cells (fibroblasts) from co-cultures comprising hepatocytes and non-parenchymal cell populations continually cultured in culture medium comprising serum (non-starved) after 4 weeks of culture. Error bars represent SEM where , *, and **** represent $p<0.01$, $p<0.001$ and $<0.0001$, respectively, assessed via t-test between non-starved and starved cultures.

FIGS. 9C-9L depict images of co-cultures comprising hepatocytes and non-parenchymal cell populations at one week (FIG. 9C) and thereafter. After one week, the composition is periodically incubated in serum-free culture medium (starved) for 3 weeks (FIG. 9J), 4 weeks, (FIG. 9K) and 6 weeks (FIG. 9L) or continually cultured in culture medium comprising serum (control) for 3 weeks (FIG. 9D), 4 weeks, (FIG. 9E) and 6 weeks (FIG. 9F). Co-cultures comprising hepatocytes and non-parenchymal cell populations wherein the non-parenchymal cells (fibroblasts) are growth arrested (growth arrested) continually cultured in culture medium comprising serum for 3 weeks (FIG. 9G), 4 weeks, (FIG. 9H) and 6 weeks (FIG. 9I). Hepatocyte island edges and outlines of the island are in white. Arrows indicate fibroblasts invading the island. Scale bar represents 50 µm.

FIG. 11A depicts a graph showing the amount of albumin produced in co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) at 1, 2, 3, 4, and 6 weeks of culture. Error bars represent SEM where *, , *, and **** represent $p<0.05$, $p<0.01$, $p<0.001$ and $<0.0001$, respectively, assessed via one-way ANOVA between treatments.

FIG. 11B depicts a graph showing the amount of urea produced in co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) at 1, 2, 3, 4, and 6 weeks of culture. Error bars represent SEM where *, , *, and **** represent $p<0.05$, $p<0.01$, $p<0.001$ and $<0.0001$, respectively, assessed via one-way ANOVA between treatments.

FIG. 11C depicts a graph showing the amount of CYP3A4 activity in co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) at 6 weeks of culture. Error bars represent SEM where *, , *, and **** represent $p<0.05$, $p<0.01$, $p<0.001$ and $<0.0001$, respectively, assessed via one-way ANOVA between treatments.

FIG. 11D depicts a graph showing the area of hepatocyte islands in co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) at 6 weeks of culture. Error bars represent SEM where *, , *, and **** represent $p<0.05$, $p<0.01$, $p<0.001$ and $<0.0001$, respectively, assessed via one-way ANOVA between treatments.

FIG. 11E depicts a graph showing the amount of CDCFDA excreted from co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) at 6 weeks of culture. Error bars represent SEM where *, , *, and **** represent p<0.05, p<0.01, p<0.001 and <0.0001, respectively, assessed via one-way ANOVA between treatments.

DETAILED DESCRIPTION OF THE INVENTION

Figure 2B:
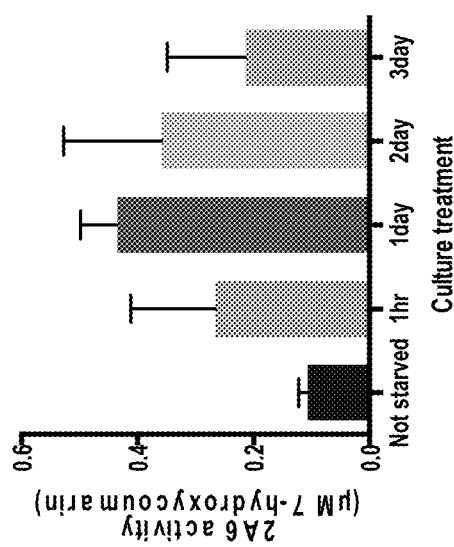
FIG. 2B depicts a graph showing the amount of CYP2A6 activity by co-cultures comprising hepatocytes and non-parenchymal cell populations wherein the composition is periodically incubated in serum-free culture medium for 1 hour, 1 day, 2 days, or 3 days and a co-culture comprising hepatocytes and non-parenchymal cell populations continually cultured in culture medium comprising serum (not starved). Error bars represent SD.

The present disclosure is based in part on the surprising discovery by the inventors that hepatocytes survive when cultures are periodically serum starved. Accordingly, the present disclosure provides a method of culturing a population of hepatocytes in vitro, comprising co-culturing the population of hepatocytes with at least one non-parenchymal cell population wherein the composition is periodically incubated in serum-free culture medium. It has been surprisingly found that incubating co-cultures of hepatocytes and least one non-parenchymal cell population periodically with serum-free culture medium can enhance functions of hepatocytes. Use of the method as described herein was found to improve morphology, promote bile canaliculi formation and extend hepatocyte functional lifetime in vitro for at least 4 weeks, as compared to only about 3-4 weeks when using a conventional culture medium containing serum for the duration. The provided long-term culture model can be used to screen drugs for their efficacious and/or toxic effects over several weeks, improve drug-transporter assays via the larger bile canaliculi network, and to model several chronic liver diseases such as hepatitis, type 2 diabetes, malaria, liver fibrosis, liver cancer, and fatty liver disease.

The present disclosure describes the development and uses of method of incubating co-cultures periodically with serum-free culture medium described above. Alternating the exposure of hepatocytes in co-culture with the serum-free culture medium and culture medium comprising serum exhibits numerous benefits relative to continuous exposure of hepatocytes to medium comprising serum. The disclosed periodic serum starvation of hepatocytes in co-culture results in cultures in which hepatocyte morphology is retained by at least 4 weeks. Hepatocyte function (e.g., enzyme activity, urea synthesis, and albumin production) is maintained significantly longer than cultures continuously exposed to culture medium comprised of serum and cultures that are continuously exposed to culture medium that is serum free. Accordingly, the disclosed periodic serum-starvation of hepatocyte co-cultures prolongs the lifetime of hepatocytes in culture relative to hepatocytes in culture that have not been serum starved. Further, the disclosed periodic serum-starvation of hepatocyte co-cultures retains hepatocyte polarity and transporters over at least 6 weeks. Notably, hepatocytes cultured under periodic serum-starvation retain the ability to correctly identify potential hepatotoxins and non-toxic compounds. The periodic starvation of cultured hepatocytes is broadly applicable to random co-cultures and micropatterned co-cultures ("MPCCs"). Various aspects of the disclosure are described in more detail below.

Unless otherwise required by context, singular terms as used herein and in the claims shall include pluralities and plural terms shall include the singular. For example, reference to "a cellular island" includes a plurality of such cellular islands and reference to "the cell" includes reference to one or more cells known to those skilled in the art, and so forth.

The use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

Described herein are several definitions. Such definitions are meant to encompass grammatical equivalents.

The term "co-culture" means the growth of more than one distinct cell type in a combined culture. Co-cultures of the present disclosure can include two or more distinct cell types. In some aspects, three or more distinct cell types are included in a co-culture. Co-cultures include, but are not limited to, cultures where two or more cell types are contained in the same container. This includes configurations where one or more of the cell types are contained within a transwell or similar device that is in contact with a container housing one or more cell types.

The term "donor" includes human and other mammalian subjects from which cells such as stem cells, primary endothelial cells, and/or primary hepatocytes may be obtained.

The term "patient" includes human and other mammalian subjects that receive either prophylactic or therapeutic treatment.

The term "periodic," when referring to the action of exchanging culture medium comprising serum with serum-free culture medium, refers to the exchanging of the two types of media in recurring, fixed intervals of time.

The term "population," when referring to a "cell population," "population of . . . cells," and the like, refers to a group of cells of a distinct cell type. The population of cells may contain cells of the same distinct cell type obtained from one or more donors. In other aspects, the population of cells may contain cells of the same distinct type obtained from one or more cell lines.

The term "stabilize" refers to a population of hepatocytes and at least one non-parenchymal cell population in co-culture initially cultured in culture media comprising serum for a period of time until the co-culture demonstrates one or more markers of hepatic function and/or hepatic morphology.

The term "subject" refers to an animal, including but not limited to a mammal including a human and a non-human primate (for example, a monkey or great ape), a cow, a pig, a cat, a dog, a rat, a mouse, a horse, a goat, a rabbit, a sheep, a hamster, a guinea pig). Preferably, the subject is a human.

I. Co-Cultures of Hepatocytes and at Least One Non-Parenchymal Cell Population

The present disclosure provides a composition comprising a population of hepatocytes and at least one non-parenchymal cell population in co-culture in vitro; and a culture medium. The composition may also comprise a culture substrate. The culture medium may comprise serum or it may not include serum (i.e., "serum-free"). The present disclosure also provides method of culturing a population of hepatocytes in vitro, comprising co-culturing the population of hepatocytes with at least one non-parenchymal cell population, and incubating the co-culture in culture medium, wherein the co-culture is incubated in culture medium comprising serum for at least one time period of about 1 hour to about 6 weeks and is incubated in culture medium that does not comprise serum (serum-free culture medium) for at least one time period of about 1 hour to about 6 weeks. The co-cultures as described herein provide a useful in vitro liver model and thus also provide a unique platform for the development and toxicology screening of therapeutic agents, including high-throughput screening of drug candidates for efficacy and toxicity. The co-cultures described herein include, but are not limited to, random co-cultures and micropatterned co-cultures ("MPCC").

The hepatocytes may be human in origin. The human hepatocytes can be, for example, primary human hepatocytes ("PHHs"). Additionally, the human hepatocytes could be derived from any human pluripotent stem cell, and an immortalized human hepatocyte cell line. The human hepatocytes may be obtained from a normal human donor or a human donor suffering from a disorder of the liver. Disorders of the liver include, but are not limited to, metabolic disorders such as type 2 diabetes, metabolic syndrome, non-alcoholic fatty liver disease ("NAFLD"), non-alcoholic steatohepatitis ("NASH"), and cardiovascular disease. Disorders of the liver may also include infectious diseases such as hepatitis B, hepatitis C, hepatitis E, dengue fever, and Ebola. The present disclosure provides a population of hepatocytes obtained from one or more human donors. Another non-limiting, exemplary co-culture is one which includes hepatocytes obtained from one or more normal human donors. Additionally, the human hepatocytes may be derived from any pluripotent stem cells, for example human induced pluripotent stem cells ("iPSC's"), embryonic stem cells ("ESC's"), hepatic resident stem cells (oval cells), and the like. A non-limiting, exemplary co-culture is one which includes hepatocytes derived from human induced pluripotent stem cells such as iCell® Hepatocytes ("iHep" or "iHeps") available from Cellular Dynamics International of Madison, Wis. The pluripotent stem cell may be from a normal or a diseased donor.

At least one of the non-parenchymal cell populations may be non-human. It is contemplated that in some instances other non-parenchymal cells, both human and non-human, may be included with the disclosed composition. At least one of the non-parenchymal cell populations may comprise stromal cells, such as but not limited to: fibroblasts, fibroblast-derived cells, macrophages, endothelial cells, pericytes, inflammatory cells, cholangiocytes, and other types of stromal cells, and combinations thereof. Fibroblasts may be, for example, mammalian fibroblasts, such as murine embryonic fibroblasts. Non-limiting examples of murine embryonic fibroblasts include 3T3-J2, NIH-3T3, Swiss-3T3, and L1-3T3 murine embryonic fibroblasts. In an aspect, the nonparenchymal cells are 3T3-J2 murine embryonic fibroblasts. A non-limiting, exemplary co-culture is one which includes non-human, mammalian fibroblasts. Another non-limiting, exemplary co-culture is one which includes non-parenchymal cells from normal and diseased donors. Non-parenchymal cells may be obtained from one or more donors suffering from a disorder of the liver. It is contemplated that other non-parenchymal cells, both liver and non-liver, and non-parenchymal cells specifically implicated in a disease can be used to provide an in vitro model for drug testing new drugs to treat the disease. The other non-parenchymal cells, both liver and non-liver, may include non-parenchymal cells that are human or non-human. In some instances, the nonparenchymal cells may be growth arrested. In other, the non-parenchymal cells are not growth arrested.

The culture substrate may comprise a glass or elastomeric structure with a suitable culture surface, such as a glass, polystyrene, or silicon slide, or polystyrene dish, slide, or microwells. A biopolymer scaffold may optionally be disposed on the culture substrate to further support and promote cell viability. Biopolymers suitable as scaffold material include, but are not limited to, alginate, chitosan, hyaluronate, fibrous proteins, collagen, silk, and elastin. Alternatively, a scaffold may be disposed on the culture substrate that comprises a hydrogel such as collagens, polyacrylamides, polyelectrolyte multilayers, polydimethylsiloxane. In an aspect, a hard substrate may be used.

The co-cultures described herein encompass, but are not limited to, randomly distributed co-cultures of hepatocytes and non-parenchymal cells, MPCCs, and hybrids of ECM overlay ("sandwich") and MPCCs. Co-culturing methods and techniques in general have been described in the literature. In particular, MPCC co-culturing materials, methods and techniques are described detail in Khetani and Bhatia, NATURE BIOTECHNOLOGY, 2008, 26(1): 120-126, the disclosure of which is herein incorporated by reference in its entirety. The co-cultures may be contact models where the hepatocyte population and at least one non-parenchymal cell population are all contained with the same well. Additionally, small molecules for hepatocyte maturation can also be applied in the co-cultures described herein. Small molecule hepatocyte maturation factors can be any from among those described in the literature and as known to those of skill in the art, including for example any of the small molecules described in Shan et al., NATURE CHEM BIOL. 2013, 9(8): 514-20, the disclosure of which is herein incorporated by reference in its entirety.

Co-cultures of the disclosure may be established as randomly distributed co-cultures of hepatocytes and non-parenchymal cells. A co-culture of hepatocytes and non-parenchymal cells may be established by seeding both cell populations at the same time. In other aspects, a culture of hepatocytes may be established first, and then non-parenchymal cells added.

The co-cultures may be established according to a micropattern established on the culture surface (MPCC). Micropatterning is not required to create co-culture models; however, micropatterning allows for clear demarcation of the hepatocyte islands. The micropattern may comprise for example a predetermined two-dimensional pattern of multiple microdots ("islands") of the hepatocytes, wherein each microdot has approximately the same microdot diameter and each of any two neighboring microdots shares approximately the same edge-to-edge spacing. While the microdot diameters and microdot spacing may be varied and do vary for cultures with different cell types, it has been found that for hepatocytes, the micropattern may be characterized by microdots each having a diameter of about 500 µm to about 700 µm, and a center-to-center spacing between each microdot of about 700 µm to about 1300 µm, or about 1000 µm to about 1300 µm, including about 1100 µm and about 1200 µm. In some aspects the micropattern may be characterized by microdots each having a diameter of about 500 µm, and an edge-to-edge spacing between each microdot of at least about 700 µm. A micropattern having the foregoing characteristics has been found to result in co-cultures of hepatocytes that remain viable and show evidence of mature phenotype retention for several days and weeks, including up to at least about 8 days, at least about 28 days, and at least 35 days. (U.S. Patent Publication No. 2015/0240203, the disclosure of which is herein incorporated by reference in its entirety.) In another aspect, the micropatterned co-cultures may be established as described in PCT/US2016/039068 and PCT/US2016/045719, both the disclosures of which are herein incorporated by reference in their entirety.

To establish the micropattern, a cell adhesion molecule may be applied to the culture substrate at the microdots, using for example a PDMS stencil. The cell adhesion molecule is any molecule to which the hepatocytes selectively adhere relative to inter-microdot space, such as collagen, fibronectin, vitronectin, laminin, extracellular matrix proteins, Arg-Gly-Asp (RGD) peptide, Tyr-Ile-Gly-Ser-Arg (YIGSR) peptide, glycosaminoglycans, hyaluronic acid, integrins, ICAMs, selectins, cadherins, cell surface protein-specific antibodies, any combination thereof, and any composition composed substantially of purified extracellular matrix protein, or mixtures of extracellular matrix proteins. Suitable extracellular matrix can be provided for example by ECM derived directly from mammalian liver, such as porcine or human liver. In one micropatterned hepatocyte co-culture, the cell adhesion molecule is, for example, any of the many extracellular matrix protein products available from a variety of commercial suppliers. Some non-limiting examples of extracellular matrix protein products available from commercial suppliers include rat tail collagen 1, matrigel, human collagens 1, 3 or 4, fibronectin, laminin and decorin, available from suppliers such as Corning Life Sciences, R& D Systems, Thermo-Fisher, and VWR. In another micropatterned hepatocyte co-culture, the cell adhesion molecule is, for example, a commercially available collagen, such as rat tail collagen.

In both the randomly distributed co-cultures and MPCCs, the hepatocytes are seeded onto the culture substrate and allowed to attach. In general, the attachment of hepatocytes to substrate occurs in the absence of serum (i.e. culture medium not supplemented with serum). The hepatocytes may be allowed to attach for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In an aspect, the hepatocytes are allowed to attach for about 3 hours to about 24 hours. In another aspect, the hepatocytes are allowed to attach for about 4 hours to about 5 hours. In another aspect, the hepatocytes are allowed to attach for about 16 hours to about 18 hours. Following attachment, the hepatocytes are incubated in medium comprising serum to allow the hepatocytes to spread. The serum maybe fetal bovine serum. The hepatocytes may be incubated in medium comprising fetal bovine serum for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours. In an aspect, the hepatocytes are incubated in the medium comprising fetal bovine serum for about 16 to about 24 hours.

Following seeding of the hepatocytes onto the culture substrate, the non-parenchymal cell population may be seeded onto the culture substrate. Prior to seeding of the non-parenchymal cell population, the non-parenchymal cell population may be expanded in the presence of medium comprising serum. In some instances the serum may be bovine serum. In other instances, the bovine serum is calf (12-18 month) serum. In further instances, the bovine serum is fetal bovine serum. Upon seeding of the non-parenchymal cell population onto the culture substrate comprising hepatocytes, the hepatocytes and non-parenchymal cell population may be incubated in the presence of medium comprising serum until the non-parenchymal cells are confluent. For example, the hepatocytes and non-parenchymal cell population may be incubated in the presence of medium comprising serum for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 26 hours, about 28 hours, about 30 hours, about 32 hours, about 34 hours, about 36 hours, about 42 hours, about 48 hours, about 54 hours, about 60 hours, about 66 hours, about 72 hours, about 78 hours, or about 84 hours. In an aspect, the hepatocytes and non-parenchymal cell population may be incubated in the presence of medium comprising serum for about 24 hours to about 72 hours.

Following the establishment of confluence of the hepatocytes and non-parenchymal cell population, the hepatocytes and non-parenchymal cell population are cultured in the presence of culture medium comprising serum or culture medium that does not comprise serum ("serum-free"). In some aspects, the hepatocytes and non-parenchymal cell population are periodically cultured in the presence of culture medium that does not contain serum ("serum-free") or culture medium comprising serum. In certain aspects, the hepatocytes and non-parenchymal cell population are first cultured in the presence of culture medium comprising serum. In other aspects, the hepatocytes and non-parenchymal cell population are first cultured in the presence of culture medium comprising serum prior to culturing said cell population in the presence of culture medium that does not contain serum ("serum-free"). In yet other aspects, the hepatocytes and non-parenchymal cell population are first cultured in the presence of culture medium comprising serum prior to culturing said cell population in the presence of culture medium that does not contain serum ("serum-free"), and followed by culturing said cell population in the presence of culture medium comprising serum.

Both the serum-free and serum containing culture mediums may comprise a base medium and may further comprise other components. In some aspects the culture medium may comprise a base medium, insulin, glucose, and/or glucagon. In some aspects the culture medium may further comprise L-glutamine, transferrin, selenium, dexamethasone and/or a buffer such as HEPES.

The culture medium may comprise a base medium. In some instances the base medium can be Dulbecco's modified Eagle's medium (DMEM), William's E base, glucose-free Dulbecco's modified Eagle's medium (DMEM,) glucose-free William's E base, Roswell Park Memorial Institute medium (RPMI), Ham's F-12 medium, or combinations thereof.

The culture medium may comprise insulin. In an aspect, the culture medium comprises from about 0.1 nM to about 10 µM of insulin. In another aspect, the culture medium comprises from about 0.1 nM to about 1 µM of insulin, from about 0.1 nM to about 100 nM of insulin, from about 0.1 nM to about 1 nM of insulin, from about 0.5 nM to about 100 nM of insulin, from about 0.5 nM to about 10 nM of insulin, or from about 0.5 nM to about 1 nM of insulin. The culture medium can comprise about 0.1 nM, about 0.5 nM, about 1 nM, about 10 nM, about 100 nM, about 1 µM, or about 10 µM insulin. Specifically, the culture medium comprises about 1 µM insulin.

Still further, the culture medium may comprise glucose. The culture medium may comprise physiologic levels of glucose. Accordingly, the culture medium comprises from about 1 mM to about 25 mM of glucose, from about 1 mM to about 20 mM of glucose, from about 1 mM to about 15 mM of glucose, from about 1 mM to about 10 mM of glucose, from about 1 mM to about 5 mM of glucose, from about 5 mM to about 25 mM of glucose, from about 5 mM to about 20 mM of glucose, from about 5 mM to about 15 mM of glucose, or from about 5 mM to about 10 mM of glucose. The culture medium can comprise about 1 mM, about 5 mM, about 10 mM, about 15 mM, about 20 mM, or about 25 mM glucose. Specifically, the culture medium comprises about 5 mM glucose.

The culture medium may comprise glucagon. The culture medium may comprise about 1 nM to about 10 nM glucagon, or about 1 nM to about 5 nM glucagon, or about 2 nM glucagon. Specifically, the culture medium comprises about 5 nM glucose.

The culture medium may be supplemented with various other components known to facilitate growth of cells, specifically hepatocytes. In an aspect, the culture medium further comprises L-glutamine, transferrin, selenium, dexamethasone, and/or a buffer such as HEPES.

The culture medium may comprise about 1 mM to about 20 mM L-glutamine, or about 1 mM to about 10 mM L-glutamine, or about 1 mM to about 5 mM L-glutamine, or about 1 mM to about 4 mM L-glutamine, or about 4 mM L-glutamine.

Further, the culture medium may comprise about 1 µg/mL to about 10 µg/mL transferrin, or about 3 µg/mL to about 8 µg/mL transferrin, or about 5 µg/mL to about 7 µg/mL transferrin, or about 6 µg/mL transferrin.

Additionally, the culture medium may comprise about 1 ng/mL to about 10 ng/mL selenium, or about 3 ng/mL to about 8 ng/mL selenium, or about 5 ng/mL to about 7 ng/mL selenium, or about 6 ng/mL selenium.

Still further, the culture medium may comprise about 1 nM to about 1000 nM dexamethasone, or about 10 nM to about 1000 nM dexamethasone, or about 100 nM to about 1000 nM dexamethasone, or about 250 nM to about 750 nM dexamethasone, or about 500 nM dexamethasone.

The culture medium may also comprise about 1 mM to about 50 mM of a buffer such as HEPES, or about 5 mM to about 25 mM of a buffer such as HEPES, or about 10 mM to about 20 mM of a buffer such as HEPES, or about 15 mM of a buffer such as HEPES.

In some aspects, the hepatocytes and non-parenchymal cell population are cultured in the presence of culture medium contains serum. In culture medium that comprises serum, the culture medium may comprise from about 1% vol/vol to about 100% vol/vol serum, from about 1% vol/vol to about 90% vol/vol serum, from about 1% vol/vol to about 80% vol/vol serum, from about 1% vol/vol to about 70% vol/vol serum, from about 1% vol/vol to about 60% vol/vol serum, from about 1% vol/vol to about 50% vol/vol serum, from about 1% vol/vol to about 40% vol/vol serum, from about 1% vol/vol to about 30% vol/vol serum, from about 1% vol/vol to about 20% vol/vol serum, from about 1% vol/vol to about 15% vol/vol serum, from about 1% vol/vol to about 10% vol/vol serum, from about 5% vol/vol to about 20% vol/vol serum, from about 5% vol/vol to about 15% vol/vol serum, or from about 5% vol/vol to about 10% vol/vol serum. The culture medium can comprise about 5% vol/vol, about 6% vol/vol, about 7% vol/vol, about 8% vol/vol, about 9% vol/vol, or about 10% vol/vol serum. Specifically, the culture medium comprises about 10% vol/vol serum. The serum can be from animal or human sources. The serum may be obtained from a normal donor or a donor suffering from a disorder of the liver. The serum can be obtained from one or more donors.

In an aspect, the culture medium containing serum comprises Dulbecco's modified Eagle's medium (DMEM) or William's E base, from about 1% to about 20% vol/vol serum, from about 0.1 µM to about 10 µM of insulin, from about 1 mM to about 30 mM of glucose, and L-glutamine, transferrin, selenium, dexamethasone, glucagon, and a buffer such as HEPES. In another aspect, the culture medium comprises Dulbecco's modified Eagle's medium (DMEM) or William's E base, from about 1% to about 20% vol/vol serum, from about 0.1 µM to about 10 µM of insulin, from about 1 mM to about 40 mM of glucose, about 1 mM to about 10 mM L-glutamine, about 1 µg/mL to about 10 µg/mL transferrin, about 1 ng/mL to about 10 ng/mL selenium, about 1 nM to about 1000 nM dexamethasone, about 1 nM to about 10 nM glucagon, and about 1 mM to about 50 mM of a buffer such as HEPES. In still another aspect, the culture medium comprises Dulbecco's modified Eagle's medium (DMEM) or William's E base, from about 5% to about 15% vol/vol serum, from about 0.1 µM to about 10 µM of insulin, from about 1 mM to about 40 mM of glucose, about 1 mM to about 10 mM L-glutamine, about 1 µg/mL to about 10 µg/mL transferrin, about 1 ng/mL to about 10 ng/mL selenium, about 1 nM to about 1000 nM dexamethasone, about 1 nM to about 10 nM glucagon, and about 1 mM to about 50 mM of a buffer such as HEPES. In still yet another aspect, the culture medium comprises Dulbecco's modified Eagle's medium (DMEM) or William's E base, about 10% vol/vol serum, about 1 µM insulin, about 25 mM glucose, about 4 mM L-glutamine, about 6 µg/mL transferrin, about 6 ng/mL selenium, about 500 nM dexamethasone, about 2 nM glucagon, and about 15 mM of a buffer such as HEPES.

In some aspects, the hepatocytes and non-parenchymal cell population are cultured in the presence of culture medium that does not contain serum ("serum-free"). The culture medium that does not contain serum ("serum-free") may comprise Dulbecco's modified Eagle's medium (DMEM) or William's E base, from about 0.1 µM to about 10 µM of insulin, from about 1 mM to about 30 mM of glucose, and L-glutamine, transferrin, selenium, dexamethasone, glucagon, and a buffer such as HEPES. In another aspect, the culture medium comprises Dulbecco's modified Eagle's medium (DMEM) or William's E base, from about 0.1 µM to about 10 µM of insulin, from about 1 mM to about 40 mM of glucose, about 1 mM to about 10 mM L-glutamine, about 1 µg/mL to about 10 µg/mL transferrin, about 1 ng/mL to about 10 ng/mL selenium, about 1 nM to about 1000 nM dexamethasone, about 1 nM to about 10 nM glucagon, and about 1 mM to about 50 mM of a buffer such as HEPES. In still another aspect, the culture medium comprises Dulbecco's modified Eagle's medium (DMEM) or William's E base, from about 0.1 µM to about 10 µM of insulin, from about 1 mM to about 40 mM of glucose, about 1 mM to about 10 mM L-glutamine, about 1 µg/mL to about 10 µg/mL transferrin, about 1 ng/mL to about 10 ng/mL selenium, about 1 nM to about 1000 nM dexamethasone, about 1 nM to about 10 nM glucagon, and about 1 mM to about 50 mM of a buffer such as HEPES. In still yet another aspect, the culture medium comprises Dulbecco's modified Eagle's medium (DMEM) or William's E base, about 1 µM insulin, about 25 mM glucose, about 4 mM L-glutamine, about 6 µg/mL transferrin, about 6 ng/mL selenium, about 500 nM dexamethasone, about 2 nM glucagon, and about 15 mM of a buffer such as HEPES.

Following the establishment of confluence of the hepatocytes and non-parenchymal cell population, the hepatocytes and non-parenchymal cell population may be cultured in the presence of culture medium comprising serum. Upon reaching confluence, the hepatocytes and non-parenchymal cell population may be incubated in the presence of culture medium comprising serum until the hepatocytes and non-parenchymal cell population is stabilized. For example, the hepatocytes and non-parenchymal cell population may be incubated in the presence of culture medium comprising serum for about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, or about 21 days. In an aspect, the hepatocytes and non-parenchymal cell population may be incubated in the presence of medium comprising serum for about 7 days to about 14 days.

Following the stabilization of the hepatocytes and non-parenchymal cell population, the hepatocytes and non-parenchymal cell population are periodically cultured in the presence of culture medium that does not contain serum ("serum-free") or culture medium comprising serum. In some aspects, the hepatocytes and non-parenchymal cell population are cultured in the presence of serum-free culture medium for at least 1 hour to about 1 day at which point the serum-free culture medium is removed and replaced with culture medium comprising serum. In other aspects, the hepatocytes and non-parenchymal cell population are cultured in the presence of serum-free culture medium for at least 1 day at which point the serum-free culture medium is removed and replaced with culture medium comprising serum. In other aspects, the hepatocytes and non-parenchymal cell population are cultured in the presence of serum-free culture medium for at least 2 days at which point the serum-free culture medium is removed and replaced with culture medium comprising serum. In other aspects, the hepatocytes and non-parenchymal cell population are cultured in the presence of serum-free culture medium for at least 3 days at which point serum-free culture medium is removed and replaced with culture medium comprising serum. In some aspects, the hepatocytes and non-parenchymal cell population are cultured in the presence of serum-free culture medium for at least 1 day at which point the serum-free culture medium is removed and replaced with culture medium comprising serum for at least 6 days. In other aspects, the hepatocytes and non-parenchymal cell population are cultured in the presence of serum-free culture medium for at least 2 days at which point the serum-free culture medium is removed and replaced with culture medium comprising serum for at least 5 days. In other aspects, the hepatocytes and non-parenchymal cell population are cultured in the presence of serum-free culture medium for at least 3 days at which point serum-free culture medium is removed and replaced with culture medium comprising serum for at least 4 days. In some aspects, one interval of periodic treatment comprises culturing the hepatocytes and non-parenchymal cell population in the presence of serum-free culture medium for at least 1 day at which point the serum-free culture medium is removed and replaced with culture medium comprising serum for at least 6 days. In other aspects, one interval of periodic treatment comprises culturing the hepatocytes and non-parenchymal cell population in the presence of serum-free culture medium for at least 2 days at which point the serum-free culture medium is removed and replaced with culture medium comprising serum for at least 5 days. In some aspects, one interval of periodic treatment comprises culturing the hepatocytes and non-parenchymal cell population in the presence of serum-free culture medium for at least 3 days at which point the serum-free culture medium is removed and replaced with culture medium comprising serum for at least 4 days. In an aspect, one interval of periodic treatment is repeated at least once, at least twice, at least three times, at least four times. In a specific aspect, stabilized hepatocytes and non-parenchymal cell population are cultured in the presence of serum-free culture medium for at least 2 days at which point the serum-free culture medium is removed and replaced with culture medium comprising serum for at least 5 days, whereby this one interval of periodic treatment is repeated three additional times for a total of 4 intervals of periodic treatment.

In an aspect, the hepatocytes are disposed in a micropattern on a culture substrate as described herein and in PCT/US2016/039068 and PCT/US2016/045719, both the disclosures of which are herein incorporated by reference in their entirety. Following the establishment of confluence of the hepatocytes, the hepatocytes are cultured in the presence of culture medium comprising serum or culture medium that does not comprise serum ("serum-free"). In one aspect, hepatocytes are periodically cultured in the presence of culture medium comprising serum for at least 1 hour to at least 1 day prior to removal of culture medium comprising serum and replacement of serum-free culture medium. In another aspect, hepatocytes are periodically cultured in the presence of culture medium comprising serum for at least 1 to at least 2 days prior to removal of culture medium comprising serum and replacement of serum-free culture medium. In another aspect, hepatocytes are periodically cultured in the presence of culture medium comprising serum for at least 1 to at least 2 days prior to removal of culture medium comprising serum and replacement of serum-free culture medium for at least 1 to at least 2 days. In yet another aspect, hepatocytes are periodically cultured for one periodic interval comprising culturing hepatocytes in the presence of culture medium comprising serum for at least 2 days prior to removal of culture medium comprising serum and replacement of serum-free culture medium for at least 2 days. In another aspect, hepatocytes are periodically cultured for at least one periodic interval, at least 2 periodic intervals, at least 3 periodic intervals, at least 4 periodic intervals, at least 5 periodic intervals, at least 6 periodic intervals, or at least 7 periodic intervals. In another aspect, hepatocytes are periodically cultured at periodic intervals for at least 4 days, at least 8 days, at least 12 days or at least 16 days.

Hepatocytes and non-parenchymal cell populations that are periodically cultured in the presence of serum-free culture medium retain hepatocyte island morphology compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain hepatocyte island morphology for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum. Hepatocytes and non-parenchymal cell populations periodically cultured in the presence of serum-free culture medium retain hepatocyte island area compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain hepatocyte island area for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium for 2 days followed by 5 days in the presence of culture medium comprising serum retain hepatocyte island morphology at least about 10% compared to hepatocytes and non-parenchymal cell populations continuously cultured in culture medium comprising serum for at least 3 weeks. In one aspect, hepatocytes and non-parenchymal cell populations that are periodically cultured in the presence of serum-free culture medium for 2 days followed by 5 days in the presence of culture medium comprising serum retain hepatocyte island morphology at least about 50% compared to hepatocytes and non-parenchymal cell populations continuously cultured in culture medium comprising serum for at least 4 weeks. In one aspect, hepatocytes and non-parenchymal cell populations that are periodically cultured in the presence of serum-free culture medium for 2 days followed by 5 days in the presence of culture medium comprising serum retain hepatocyte island morphology at least about 50% compared to hepatocytes and non-parenchymal cell populations continuously cultured in culture medium comprising serum for at least 6 weeks.

Hepatocytes and non-parenchymal cell populations that are periodically cultured in the presence of serum-free culture medium retain hepatocyte polarization compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain hepatocyte polarization for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium for 2 days followed by 5 days in the presence of culture medium comprising serum retain hepatocyte polarization at least about 4-fold higher than hepatocytes and non-parenchymal cell populations continuously cultured in culture medium comprising serum for at least 6 weeks. Hepatocytes and non-parenchymal cell populations that are periodically cultured in the presence of serum-free culture medium retain more bile canaliculi compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain more bile canaliculi by at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum.

Hepatocytes and non-parenchymal cell populations that are periodically cultured in the presence of serum-free culture medium retain hepatocyte function compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain hepatocyte function for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum.

Hepatocytes and non-parenchymal cell populations that are periodically cultured in the presence of serum-free culture medium retain the process of albumin production compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain the process of albumin production for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium for 1 day followed by 6 days in the presence of culture medium comprising serum produce at least 3-fold more albumin than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 2 days followed by 5 days in the presence of culture medium comprising serum produce at least 3-fold more albumin than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 3 days followed by 4 days in the presence of culture medium comprising serum produce at least 3-fold more albumin than hepatocytes and non-parenchymal cell populations continuously cultured in culture medium comprising serum for at least 6 weeks.

Hepatocytes and non-parenchymal cell populations that are periodically cultured in the presence of serum-free culture medium retain the process of urea synthesis compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain the process of urea synthesis for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium for 1 day followed by 6 days in the presence of culture medium comprising serum synthesize at least 4-fold more urea than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 2 days followed by 5 days in the presence of culture medium comprising serum synthesize at least 2-fold more urea than hepatocytes and non-parenchymal cell populations continuously cultured in culture medium comprising serum for at least 6 weeks. In another aspect, hepatocytes and non-parenchymal cell populations that are periodically cultured in the presence of serum-free culture medium retain the processes of albumin production and urea synthesis for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum.

Hepatocytes and non-parenchymal cell populations that are periodically cultured in the presence of serum-free culture medium retain drug enzyme activity compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain drug enzyme activity for at least 7 weeks, at least 6 weeks, at least 5 weeks, at least 4 weeks, at least 3 weeks, at least 2 weeks, or at least 1 week compared to compared to hepatocytes and non-parenchymal cell populations continuously cultured in culture medium comprising serum, hepatocytes periodically cultured in the presence of serum-free culture medium, and hepatocytes continuously cultured in culture medium comprising serum. Hepatocytes and non-parenchymal cell populations that are periodically cultured in the presence of serum-free culture medium retain activity of one or more of the enzymes CYP3A4, CYP2A6, CYP2C9, and/or CYP1A2 compared to hepatocytes and non-parenchymal cell populations continuously cultured in culture medium comprising serum, hepatocytes periodically cultured in the presence of serum-free culture medium, and hepatocytes continuously cultured in culture medium comprising serum. In one aspect, hepatocytes and non-parenchymal cell populations that are periodically cultured in the presence of serum-free culture medium retain activity of one or more of the enzymes CYP3A4, CYP2A6, CYP2C9, and/or CYP1A2 activity for at least 7 weeks, at least 6 weeks, at least 5 weeks, at least 4 weeks, at least 3 weeks, at least 2 weeks, or at least 1 week compared to hepatocytes and non-parenchymal cell populations continuously cultured in culture medium comprising serum.

In one aspect, hepatocytes and non-parenchymal cell populations that are periodically cultured in the presence of serum-free culture medium for 1 day followed by 6 days in the presence of culture medium comprising serum have at least 2-fold more CYP3A4 activity than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 2 days followed by 5 days in the presence of culture medium comprising serum have at least 5-fold more CYP3A4 activity than hepatocytes and non-parenchymal cell populations continuously cultured in culture medium comprising serum for at least 4 weeks. In one aspect, hepatocytes and non-parenchymal cell populations that are periodically cultured in the presence of serum-free culture medium for 2 days followed by 5 days in the presence of culture medium comprising serum have at least 2-fold more CYP3A4 activity than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 3 days followed by 4 days in the presence of culture medium comprising serum have at least 2-fold more CYP3A4 activity than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 1 day followed by 6 days in the presence of culture medium comprising serum have at least 3-fold more CYP2A6 activity than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 2 days followed by 5 days in the presence of culture medium comprising serum have at least 3-fold more CYP2A6 activity than hepatocytes and non-parenchymal cell populations continuously cultured in culture medium comprising serum for at least 3 weeks. In one aspect, hepatocytes and non-parenchymal cell populations that are periodically cultured in the presence of serum-free culture medium for 2 days followed by 5 days in the presence of culture medium comprising serum have at least 2-fold more CYP2A6 activity than hepatocytes and non-parenchymal cell populations continuously cultured in culture medium comprising serum for at least 4 weeks. In one aspect, hepatocytes and non-parenchymal cell populations that are periodically cultured in the presence of serum-free culture medium for 2 days followed by 5 days in the presence of culture medium comprising serum have at least 2-fold more CYP2A6 activity than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 3 days followed by 4 days in the presence of culture medium comprising serum have at least 2-fold more CYP2A6 activity than hepatocytes and non-parenchymal cell populations continuously cultured in culture medium comprising serum for at least 6 weeks. In one aspect, hepatocytes and non-parenchymal cell populations that are periodically cultured in the presence of serum-free culture medium for 2 days followed by 5 days in the presence of culture medium comprising serum have at least 2-fold more CYP2C9 activity than hepatocytes and non-parenchymal cell populations continuously cultured in culture medium comprising serum for at least 4 weeks. In one aspect, hepatocytes and non-parenchymal cell populations that are periodically cultured in the presence of serum-free culture medium for 2 days followed by 5 days in the presence of culture medium comprising serum have at least 1-fold more CYP1A2 activity than hepatocytes and non-parenchymal cell populations continuously cultured in culture medium comprising serum for at least 4 weeks.

The co-culture described above may be used for drug discovery and drug screening as described in greater detail below.

II. Uses

The hepatocytes and non-parenchymal cell populations periodically cultured in the presence of serum-free culture medium as described herein may be used in various methods, such as but not limited to drug discovery and drug screening. The hepatocytes and non-parenchymal cell populations periodically cultured in the presence of serum-free culture medium as described herein can be used to develop and screen candidate therapeutic agents for treating any hepatic disease or disorder, or for screening the toxicity of candidate therapeutic agents for treating any other disease or disorder. In an aspect, the hepatic disease or disorder is metabolic disorder such as type 2 diabetes, metabolic syndrome, non-alcoholic fatty liver disease ("NAFLD"), non-alcoholic steatohepatitis ("NASH"), and cardiovascular disease or an infectious disease such as hepatitis B, hepatitis C, hepatitis E, dengue fever, and Ebola. For example, hepatocytes and non-parenchymal cell populations periodically cultured in the presence of serum-free culture medium as described herein provide for a model of in vitro prediction of drug induced liver toxicity, and establish a new direction in in vitro models of the liver. Notably, the periodically serum starved hepatocytes and non-parenchymal cell populations provided herein facilitates the use of in vitro cultures for at least 1 week, at least 2 weeks, at least 3 weeks, at least 4 weeks, at least 5 weeks, at least 6 weeks. The periodically serum starved hepatocytes and non-parenchymal cell populations provided herein have a significantly prolonged lifetime and maintain function without losing their utility for drug screening and glucose metabolism studies.

A candidate therapeutic agent (also referred to as a "drug candidate" or "test compound") may be a small molecule, a peptide, a polypeptide, an oligonucleotide, a polynucleotide, or an antibody.

Any of the methods may involve determining a baseline or control value, for example, of any indicator of liver function such as gluconeogenesis, glycolysis, glycogen storage, enzyme activity, albumin secretion, urea production, gene expression, inducible liver enzyme activity and the like, in the hepatocytes in co-culture before administering a dosage of a candidate therapeutic agent or other test agent, and comparing this with a value or level after the exposure and noting any significant change (i.e., greater than the typical margin of experimental error in repeat measurements of the same sample, expressed as one standard deviation from the mean of such measurements) over the control. In a non-limiting example, at least one indicator of hepatic function can be a measure of albumin production, urea production, ATP production, glutathione production, enzyme activity, lipid accumulation, liver gene expression, liver protein expression, or inducible liver enzyme activity in the hepatocytes.

In some aspects, albumin production can be measured from the hepatocyte culture supernatant after at least 1 day, at least 1 week, at least 2 weeks, at least 3 weeks, at least 4 weeks, at least 5 weeks, at least 6 weeks, or at least 7 weeks. In some aspects, albumin production can be measured from hepatocyte culture supernatant using an enzyme-linked immunosorbent assay (ELISA), high-performance liquid chromatography (HPLC), and/or other methods known in the art. In other aspects, albumin production can be an indicator of hepatic function if hepatocytes produce at least 5%, at least 10%, at least 20%, at least 30%, at least 40%, at least 50%, at least 60%, at least 70%, at least 80%, at least 90%, at least 100% more albumin compared to one or more control standards known in the art.

In some aspects, urea production can be measured from the hepatocyte culture supernatant after at least 1 day, at least 1 week, at least 2 weeks, at least 3 weeks, at least 4 weeks, at least 5 weeks, at least 6 weeks, or at least 7 weeks. In some aspects, urea production can be measured from hepatocyte culture supernatant using colorimetric detection, and/or other methods known in the art. In other aspects, urea production can be an indicator of hepatic function if hepatocytes produce at least 5%, at least 10%, at least 20%, at least 30%, at least 40%, at least 50%, at least 60%, at least 70%, at least 80%, at least 90%, at least 100% more urea compared to one or more control standards known in the art.

In some aspects, ATP production can be measured from hepatocytes after at least 1 day, at least 1 week, at least 2 weeks, at least 3 weeks, at least 4 weeks, at least 5 weeks, at least 6 weeks, or at least 7 weeks. In some aspects, ATP production can be measured using an ELISA, a luciferase-based assay, by the hexokinase/glucose-6-phosphate dehydrogenase method, and/or other methods known in the art. In other aspects, ATP production can be an indicator of hepatic function if hepatocytes produce at least 5%, at least 10%, at least 20%, at least 30%, at least 40%, at least 50%, at least 60%, at least 70%, at least 80%, at least 90%, at least 100% more ATP compared to one or more control standards known in the art.

In some aspects, glutathione production can be measured from hepatocytes at least 1 day, at least 1 week, at least 2 weeks, at least 3 weeks, at least 4 weeks, at least 5 weeks, at least 6 weeks, or at least 7 weeks. In some aspects, glutathione production can be measured by reacting glutathione with dithionitrobenzoic acid to produce a conjugate that can be detected by fluorescence or absorbance, reaction of glutathione with orthophthaldehyde to yield a product that can be measured spectrofluorometrically or separated by separated by HPLC, and/or other methods known in the art.

In other aspects, glutathione production can be an indicator of hepatic function if hepatocytes produce at least 5%, at least 10%, at least 20%, at least 30%, at least 40%, at least 50%, at least 60%, at least 70%, at least 80%, at least 90%, at least 100% more glutathione compared to one or more control standards known in the art.

In some aspects, lipid accumulation can be measured from hepatocytes after at least 1 day, at least 1 week, at least 2 weeks, at least 3 weeks, at least 4 weeks, at least 5 weeks, at least 6 weeks, or at least 7 weeks. In some aspects, lipid accumulation can be measured by a fatty acid oxidation assay, a lipogenesis assay, and/or other methods known in the art. In other aspects, lipid accumulation can be an indicator of hepatic function if cultures accumulate at least 5%, at least 10%, at least 20%, at least 30%, at least 40%, at least 50%, at least 60%, at least 70%, at least 80%, at least 90%, at least 100% more lipids compared to one or more control standards known in the art.

In some aspects, liver gene expression can be measured from hepatocytes after at least 1 day, at least 1 week, at least 2 weeks, at least 3 weeks, at least 4 weeks, at least 5 weeks, at least 6 weeks, or at least 7 weeks. In some aspects, liver gene expression can be measured by northern blot, microarray analysis, reverse transcription polymerase chain reaction (RT-PCR), and/or other methods known in the art. In other aspects, liver gene expression can be an indicator of hepatic function if liver gene expression is either increased or decreased by at least 5%, at least 10%, at least 20%, at least 30%, at least 40%, at least 50%, at least 60%, at least 70%, at least 80%, at least 90%, at least 100% in hepatocytes compared to gene expression in one or more control standards known in the art.

In some aspects, liver protein expression can be measured from hepatocytes after at least 1 day, at least 1 week, at least 2 weeks, at least 3 weeks, at least 4 weeks, at least 5 weeks, at least 6 weeks, or at least 7 weeks. In some aspects, liver protein expression can be measured by western blot, immunohistochemistry, and/or other methods known in the art. In other aspects, liver protein expression can be an indicator of hepatic function if liver protein expression is either increased or decreased by at least 5%, at least 10%, at least 20%, at least 30%, at least 40%, at least 50%, at least 60%, at least 70%, at least 80%, at least 90%, at least 100% in hepatocytes compared to protein expression in one or more control standards known in the art.

In some aspects, inducible liver enzyme activity can be measured from hepatocytes after at least 1 day, at least 1 week, at least 2 weeks, at least 3 weeks, at least 4 weeks, at least 5 weeks, at least 6 weeks, or at least 7 weeks. In some aspects, any method involving measurement of one or more inducible liver enzymes, such enzymes include, in non-limiting example, CYP enzymes such as CYP2C9 (luciferin-H), CYP3A4 (luciferin-IPA), CYP1A1, CYP1A2, CYP2B6, CYP2A6, and CYP2D6 (luciferin ME-EGE), all CYP450 enzymes such as CYP2C8, CYP2C19, CYP2E1, and phase II enzymes such as UGTs, SULTs and NATs, and any combination thereof may be used. In other aspects, inducible liver enzyme activity can be indicator of hepatic function if inducible liver enzyme activity is at least 5%, at least 10%, at least 20%, at least 30%, at least 40%, at least 50%, at least 60%, at least 70%, at least 80%, at least 90%, at least 100% higher in hepatocytes compared to one or more control standards known in the art.

Any of the methods may involve determining a baseline or control value, for example, of any indicator of normal liver morphology such as hepatocyte island area, hepatocyte polarization and the like, in the hepatocytes in co-culture before administering a dosage of a candidate therapeutic agent or other test agent, and comparing this with a value or level after the exposure and noting any significant change (i.e., greater than the typical margin of experimental error in repeat measurements of the same sample, expressed as one standard deviation from the mean of such measurements) over the control. In a non-limiting example, at least one indicator of normal liver morphology can be a measure of hepatocyte island area or hepatocyte polarization.

In some aspects, area of hepatocyte island formation in co-cultures can be measured after at least 1 day, at least 1 week, at least 2 weeks, at least 3 weeks, at least 4 weeks, at least 5 weeks, at least 6 weeks, or at least 7 weeks. In some aspects, hepatocyte island area can be measured using phase contrast imaging, and/or other methods known in the art. In other aspects, hepatocyte island area can be an indicator of normal liver morphology if the average hepatocyte island area is increased by at least 5%, at least 10%, at least 20%, at least 30%, at least 40%, at least 50%, at least 60%, at least 70%, at least 80%, at least 90%, at least 100% in hepatocytes compared to hepatocyte island area in one or more control standards known in the art.

In some aspects, hepatocyte polarization in co-cultures can be measured after at least 1 day, at least 1 week, at least 2 weeks, at least 3 weeks, at least 4 weeks, at least 5 weeks, at least 6 weeks, or at least 7 weeks. In some aspects, hepatocyte polarization can be measured the number of bile canaliculi in co-cultures using CDCFDA fluorescent staining to measure CDCFDA secretion per cell number (determined by Hoechst 33342 staining to visualize cell nuclei), and/or other methods known in the art. In other aspects, hepatocyte polarization can be an indicator of normal liver morphology if the number of bile canaliculi is increased by at least 5%, at least 10%, at least 20%, at least 30%, at least 40%, at least 50%, at least 60%, at least 70%, at least 80%, at least 90%, at least 100% in hepatocytes compared to the number of bile canaliculi in one or more control standards known in the art.

(a) Screening Assays

The present disclosure provides an in vitro model of diseases or disorders of the liver which can be utilized in various methods for identifying and screening of potential therapeutic agents, and for drug development. Disorders of the liver include, but are not limited to, metabolic disorders such as type 2 diabetes, metabolic syndrome, non-alcoholic fatty liver disease ("NAFLD"), and non-alcoholic steatohepatitis ("NASH"). In an aspect, the hepatic disease or disorder is an infectious disease, such as hepatitis B, hepatitis C, hepatitis E, dengue fever, and Ebola.

For example, the compositions of the present disclosure may be used in vitro to screen a wide variety of compounds, such as small molecules, antibodies, peptides, polypeptides, nucleic acid-based agents and the like, to identify therapeutic agents having a therapeutic effect on liver function in any disease or disorder of the liver, and/or to assess the toxicity of any such therapeutic agent before clinical implementation. For example, following contact of a co-culture with a candidate therapeutic agent, various cellular functions in the hepatocytes and/or human endothelial cells may be assessed by examining gene expression, albumin production, urea production, cytochrome P450 (CYP) metabolic activity or any inducible liver enzyme activity, organelle stress, cell surface markers, secreted factors, uptake and secretion of liver-specific products, and response to hepatotoxins, by detecting and/or measuring level of a protein, metabolite, reporter molecule, label, or gene expression level such as through gene fluorescence in the cell or in the culture media.

In non-limiting example, at least one indicator of hepatic function can be, for example, albumin production, urea production, ATP production, glutathione production, enzyme activity, lipid accumulation, liver gene expression, or liver protein expression in the hepatocytes. Additionally, following contact with a candidate therapeutic agent, hepatocytes and non-parenchymal cell populations periodically cultured in the presence of serum-free culture medium as described may be used to determine the hepatic clearance of a potential therapeutic agent. Accordingly, periodically serum-starved hepatocytes and non-parenchymal cell populations may be used to quantitatively determine hepatic clearance rates of drugs. See for example, Lin et al., DRUG METAB DISPOS 2016; 44(1): 127-36, the disclosure of which is hereby incorporated by reference in its entirety. Further, following contact of periodically serum-starved hepatocytes and non-parenchymal cell populations with a candidate therapeutic agent, the periodically serum-starved hepatocytes and non-parenchymal cell populations may be used to determine drug metabolites. Accordingly, using the periodically serum-starved hepatocytes and non-parenchymal cell populations disclosed herein, metabolite profile data may be obtained for a potential therapeutic agent. See for example, Wang et al., DRUG METAB DISPOS 2010; 38(10): 1900-5, the disclosure of which is hereby incorporated by reference in its entirety.

Gluconeogenesis and other liver functions such as albumin secretion, urea production, and glycolysis and glycogen storage may be monitored in the presence and absence of one or more stimuli, test agent, or candidate therapeutic agent. For example, periodically serum-starved hepatocytes and non-parenchymal cell populations as described herein may be tested for any one or more of albumin secretion, urea production, ATP production, lipid accumulation, induction of inducible liver (e.g., CYP) enzyme levels, gluconeogenesis, glycolysis and glycogen storage in the presence and absence of varying levels of candidate therapeutic agents. In any method involving measurement of one or more inducible liver enzymes, such enzymes include, in non-limiting example, CYP enzymes such as CYP2C9 (luciferin-H), CYP3A4 (luciferin-IPA), CYP1A1, CYP1A2, CYP2B6, CYP2A6, and CYP2D6 (luciferin ME-EGE), all CYP450 enzymes such as CYP2C8, CYP2C19, CYP2E1, and phase II enzymes such as UGTs, SULTs and NATs, and any combination thereof.

Levels of biomarkers such as for example specific metabolites may also be used in screening assays for agents. This may also be accomplished using standard cytological and/or histological techniques including the use of immunocytochemical techniques employing stains that recognize specific cellular components such as lipids, or antibodies that specifically bind to biomarkers with antigenic activity. For example, periodically serum-starved hepatocytes and non-parenchymal cell populations of the present disclosure may be exposed to a test agent or candidate therapeutic agents. After incubation, the periodically serum-starved hepatocytes and non-parenchymal cell populations may be examined for change in biomarker production as an indication of the efficacy of the test substance. Varying concentrations of a candidate therapeutic agent may be tested as known in the art to derive a dose-response curve.

(b) Target Validation

The compositions of the disclosure can be used in drug development for specific target identification and target validation. The disclosed periodically serum-starved hepatocytes and non-parenchymal cell populations are useful for identifying targets and predicting the role of one or more biomolecules in liver function in a disease or disorder of the liver. A "disease or disorder of the liver" is any medical condition having a negative effect on any liver function. Non-limiting examples of liver diseases and disorders include cirrhosis, diabetes, fibrosis, any chronic hepatitis (including but not limited to A, B, C, D, and E), non-alcoholic fatty liver disease ("NAFLD"), alcoholic fatty liver, tumors of the liver such as hepatic carcinoma, and genetic disorders such as alpha-1-anti-trypsin deficiency. For example, the cultures and systems may be used to identify proteins playing a potential role in fibrosis of the liver, or those playing a potential role in diabetic processes or diabetic liver pathways.

The periodically serum-starved hepatocytes and non-parenchymal cell populations and systems are also useful for validating the predicted role of one or more biomolecules in liver function in a disease or disorder of the liver. For example, proteins identified in preliminary studies (e.g., studies of primary hepatocytes in conventional culture systems or cryogenically preserved hepatocytes, studies in other liver models, differential expression studies, etc.) as playing a potential role in disease processes or disease pathways can be tested in a composition as described herein to confirm the potential role. Proteins that may be identified in periodically serum-starved hepatocytes and non-parenchymal cell populations, for example proteins suspected to play a role in diseased or disordered liver function, may be modulated (e.g., up-regulated or down-regulated) in the periodically serum-starved hepatocytes and non-parenchymal cell populations described herein, and processes and pathways related to the disease or disorder may be assayed following modulation. For example, candidate proteins can be "knocked out/down" using gene knockout or suppression techniques, for example, using various genomic editing techniques, or the introduction of RNA interference (RNAi) agents. Inhibition of liver pathways may be tested following down-regulation and candidate proteins thought to be important in disease or disordered liver function may be thus validated.

Any method using the co-cultures as disclosed herein may comprise initially preparing or otherwise obtaining a co-culture of hepatocytes and non-parenchymal cells as described herein. In one aspect, a stable, growing co-culture is established as described herein above. In one aspect, the present disclosure provides a method of determining the efficacy of a candidate therapeutic agent for treating a disease or disorder of the liver. The candidate therapeutic agent may be a small molecule, a peptide, a polypeptide, an oligonucleotide, a polynucleotide, or an antibody.

The periodically serum-starved hepatocytes and non-parenchymal cell populations are exposed to varying concentrations of the candidate therapeutic agent. The amount of the candidate therapeutic agent may be, according to knowledge available to those of skill in the art, an amount representing a proposed dose or range of proposed doses in a clinical population. The time over which the hepatocytes in the periodically serum-starved hepatocytes and non-parenchymal cell population are exposed to the candidate therapeutic agent may be, according to knowledge available to those of skill in the art, a period of days, weeks, or months representing time course of exposure in a clinical population. After incubation with the agent, the periodically serum-starved hepatocytes and non-parenchymal cell population is examined to determine impact of the agent if any on one or more target biomolecules or pathways identified as potentially involved in liver function in a disease or disorder of the liver, as described above. Once a testing range is established, varying concentrations of the agent can be tested to determine therapeutically effective amount of the test compound.

As noted above, the hepatocytes can be obtained or derived from donors. In further aspects, hepatocytes can be derived from stem cells obtained from one or more donors. In another aspect, the hepatocytes can be obtained from one or more donors suffering from a disease or disorder of the liver. Alternatively, the hepatocytes can be derived from stem cells obtained from one or more donors suffering from a disease or disorder of the liver.

By way of example, hepatocytes can be obtained from one or more donors suffering from a metabolic disorder of the liver. The methods therefore encompass, for example, a method for testing a candidate therapeutic agent for treating a disorder of the liver, including maintaining a periodically serum-starved hepatocytes and non-parenchymal cell population as described herein for a time and under conditions sufficient to allow albumin and/or urea production by the hepatocytes in the periodically serum-starved hepatocytes and non-parenchymal cell population; and determining a level of albumin and/or urea production by the hepatocytes in the periodically serum-starved hepatocytes and non-parenchymal cell population, wherein the level of albumin and/or urea production relative to the level of albumin and/or urea production in a population of a hepatocyte and non-parenchymal cell population continually grown in a culture comprising serum is indicative of the efficacy of the test compound as an therapeutic agent for treating the disorder of the liver. The method may further comprise, prior to determining the level of albumin and/or urea production, periodically serum-starved hepatocytes and non-parenchymal cell population for at least 1 week, at least 2 weeks, at least 3 weeks, at least 4 weeks, at least 5 weeks, at least 6 week.

It should be understood that the present disclosure encompasses methods of identifying any test agent useful for modulating a biological activity of interest in a hepatocyte, in which a periodically serum-starved hepatocytes and non-parenchymal cell population as disclosed herein is contacted with the test agent; the periodically serum-starved hepatocytes and non-parenchymal cell population is maintained for a time and under conditions sufficient for the hepatocytes to generate a signal indicative of the biological activity; and a signal generated by the hepatocytes in the presence of the test agent is detected, wherein the signal relative to a signal generated in a hepatocyte in a hepatocytes and non-parenchymal cell population continually grown in a culture comprising serum is indicative of an effect on the biological activity of interest in the hepatocytes. The signal indicative of the biological activity of interest may be for example a protein expression level or a protein secretion level. The biological activity of interest may be albumin production and/or urea synthesis.

(c) Toxicity Studies

In addition to the above-described uses of the periodically serum-starved hepatocytes and non-parenchymal cell populations and/or systems of the disclosure in screening for therapeutic agents for treating a disease or disorder of the liver, the periodically serum-starved co-cultures may also be used in toxicology studies to determine the hepatotoxicity of an agent identified as a potential therapeutic agent. Toxicology studies may be performed on periodically serum-starved co-cultures featuring hepatocytes from donors suffering from a disease or disorder of the liver, as described herein, which may be contrasted with comparable studies in cells from a different source. The periodically serum-starved hepatocytes and non-parenchymal cell populations described herein may be used in vitro to test a variety of potential therapeutic compounds for hepatotoxicity. Any of the screening methods described herein above may further comprise determining the toxicity of the agent by measuring in the hepatocytes in the periodically serum-starved co-culture at least one cell signal indicative of cell toxicity. Still further, the periodically serum-starved co-cultures may be used to determine the hepatic clearance of a potential therapeutic agent. Accordingly, the serum-starved hepatocytes and non-parenchymal cell populations may be used to quantitatively determine hepatic clearance rates of drugs. Additionally, the serum-starved hepatocytes and non-parenchymal cell populations may be used to determine drug metabolites. Accordingly, using the serum-starved hepatocytes and non-parenchymal cell populations disclosed herein, metabolite profile data may be obtained for a potential therapeutic agent.

Toxicity results may be assessed for example by observation of any of the following: a change in albumin and/or urea production, induction of any inducible liver enzyme such as cytochrome P450 (CYP) enzymes, cellular necrosis, loss of membrane integrity, cell lysis, decrease in cell viability, apoptosis, mitochondrial membrane potential, mitochondrial DNA, ER stress, organelle stress, change in endothelial cell surface markers, secretion of cell factors, and steatosis, using any one or more of vital staining techniques, ELISA assays, RT-qPCR, immunohistochemistry, imaging, electron microscopy, and the like or by analyzing the cellular content of the culture, e.g., by total cell counts, and differential cell count, by metabolic markers such as MTT and XTT, or by hepatocyte imaging technology (HIAT).

For example, serum-starved hepatocytes and non-parenchymal cell populations as described herein are exposed to varying concentrations of a candidate therapeutic agent. The amount of the candidate therapeutic agent may be, according to knowledge available to those of skill in the art, an amount representing a proposed dose or range of proposed doses in a clinical population. The time over which the hepatocytes are exposed to the candidate therapeutic agent may be, according to knowledge available to those of skill in the art, a period of days, weeks, or months representing time course of exposure in a clinical population. After incubation with the agent, the serum-starved co-culture is examined to determine the highest tolerated dose, i.e., the concentration of the agent at which the earliest morphological and/or functional abnormalities appear or are detected. Cytotoxicity testing may also be performed using a variety of supravital dyes to assess cell viability in the serum-starved hepatocytes and non-parenchymal cell populations, using techniques known to those skilled in the art. Once a testing range is established, varying concentrations of the agent can be examined for hepatotoxic effect.

The present disclosure thus provides a method for determining the cellular toxicity of a candidate therapeutic agent or test compound, the method comprising contacting a serum-starved hepatocytes and non-parenchymal cell population as described herein with the test compound; maintaining the serum-starved co-culture for a time and under conditions sufficient to allow an effect of the test compound on the hepatocytes; and taking a test measurement and/or otherwise obtaining test data indicative of a negative impact of the test compound on hepatocytes, which is indicative of toxicity of the test compound. The test measurement can be any measurement which provides an indicator of hepatic cell function. In a non-limiting example, at least one indicator of hepatic function can be a measure of albumin production, urea production, ATP production, glutathione production, enzyme activity, lipid accumulation, liver gene expression, liver protein expression, or inducible liver enzyme activity in the hepatocytes. For example, the test measurement can be a measurement of at least one or any combination of albumin, urea, enzyme activity, lipid accumulation, ATP production, and gene expression. The test measurement can be a measurement of at least one inducible liver (e.g., CYP) enzyme level. Test data may include applying hepatocyte imaging technology (HIAT) to the hepatocytes and/or human endothelial cells to obtain a test image. Test data may include using other imaging technology on the co-cultures to obtain a test image. The test measurement and/or test image is compared to a control measurement or control image from the hepatocytes before contact with the test compound, and a difference between the test measurement and control measurement, or between test image and control image is indicative of toxicity of the test compound. For example, a relative decrease in albumin and/or urea production in test measurements as compared to control, following exposure of the co-culture to the test compound is indicative of hepatotoxicity.

The present disclosure also provides a method of determining the toxicity arising from a drug interaction. For example, the potential toxicity of an interaction between a first test compound and a second test compound can be examined by contacting a periodically serum-starved hepatocytes and non-parenchymal cell population as described herein with the first and second test compounds; maintaining the periodically serum-starved co-culture for a time and under conditions sufficient to allow an effect of an interaction between the first and second test compounds on the hepatocytes; and taking a test measurement and/or otherwise obtaining test data as described above, which is indicative of toxicity of the interaction of the first and second test compounds.

The present disclosure also provides a method of determining whether a test compound alleviates hepatic dysfunctions caused by hepatocytes. For example, the effects of a test compound can be examined by contacting a periodically serum-starved hepatocytes and non-parenchymal cell population as described herein with the test compound; maintaining the a periodically serum-starved co-culture for a time and under conditions sufficient to allow an effect of the test compound on the hepatocytes; and taking a test measurement and/or otherwise obtaining test data as described above, which is indicative of effect of test compounds on hepatic function. In some aspects more than one test compound can be examined at one time. For example, two, three, four, five, six, 7, 8, 9, or 10 test compounds can be examined.

Additionally, the present disclosure thus also provides a method for determining the effects of chronically elevated or reduced levels of glucose, fructose and/or fatty acids on the liver and liver function. The method comprises for example contacting a periodically serum-starved hepatocytes and non-parenchymal cell population as described herein with a predetermined amount of one or more metabolites such as glucose, fructose, and or fatty acids, wherein the hepatocytes are obtained from one or more donors suffering from a disorder of the liver; maintaining the periodically serum-starved co-culture for a time and under conditions sufficient for the hepatocytes to generate a signal indicative of modified cellular function induced by the predetermined amount of one or more metabolites; and detecting the signal generated by hepatocytes in the presence of the one or more metabolites, wherein the signal relative to a signal generated in a control cell subject to the same conditions is indicative of an effect of the amount of the one or more metabolites on the hepatocytes. The signal indicative of an effect on cell function may be a change in transcription, translation or secretion of a protein, cellular necrosis, loss of membrane integrity, cell lysis, decrease in cell viability, apoptosis, mitochondrial membrane potential, mitochondrial DNA, ER stress, and steatosis. The predetermined amount may be an amount which is elevated or reduced relative to a control amount which is representative of an amount of each metabolite which is considered within the range of normal in vivo values for the metabolite. The time over which the hepatocytes are exposed to the elevated or reduced level(s) of metabolite(s) may be, according to knowledge available to those of skill in the art, a period of days, weeks or months representing chronic elevation or reduction of the metabolite in a clinical population.

It should be understood that many other signals of toxicity from the hepatocytes within a periodically serum-starved hepatocytes and non-parenchymal cell population can be detected and/or measured and compared to controls to identify and/or quantify toxicity induced by a candidate therapeutic agent, wherein the signal relative to a signal generated in hepatocytes and non-parenchymal cell populations continually cultured in culture medium comprising serum, is indicative of a toxic effect of the candidate agent on the hepatocytes. Such signals include, in non-limiting example, cellular necrosis, loss of membrane integrity, cell lysis, decrease in cell viability, apoptosis, mitochondrial membrane potential, mitochondrial DNA, ER stress, and steatosis, any one of which can be readily measured using techniques and materials known in the art.

(d) Personalized Medicine

It has been found that certain correlations can exist between an individual subject's particular genotype with respect to specific molecular markers, and drug treatment efficacy. Any of the periodically serum-starved co-cultures and methods described herein can also be used to develop personalized medicine, to determine whether any such correlation exists between a particular genotype and selected drug treatment for a disease or disorder of the liver. For example, serum-starved co-cultures can be prepared using hepatocytes derived from pluripotent stem cells obtained from a variety of donors of different genotypes, and any therapeutic candidate can be tested for efficacy against each genotype to determine whether any one or subset of the tested genotypes fares better or worse with a given therapeutic candidate. Any therapeutic candidate can be tested for effect on any inducible liver enzymes, and/or for a negative interaction with a second therapeutic candidate. Such information considered together with the genotype of an individual subject, can be used by a health care provider to determine a treatment option with the highest likelihood of efficacy for the individual subject, and/or to determine a risk of a negative side effect in the individual subject from a therapeutic candidate.

(e) Regenerative Medicine

The present disclosure also provides methods of engineering liver tissue for regenerative medicine. The liver tissue prepared via the methods disclosed herein may be used to replace failing livers. The use of the physiologic hepatocyte medium comprising human serum greatly enhances the stabilization of liver cells prior to implantation. Further, the medium prevents the liver cells from developing disease phenotypes prior to implantation.

It will be readily apparent to those skilled in the art that other suitable modifications and adaptations of the methods of the disclosure described herein are obvious and may be made using suitable equivalents without departing from the scope of the disclosure or the embodiments disclosed herein. Having now described the present disclosure in detail, the same will be more clearly understood by reference to the following examples, which are included for purposes of illustration only and are not intended to be limiting of the disclosure.

III. Kits Containing Co-Cultures of Hepatocytes and at Least One Non-Parenchymal Cell Population The present disclosure also provides a kit for determining the effect of a test agent on hepatocytes. A kit may comprise for example: a population of human hepatocytes and at least one non-parenchymal cell population for preparing one or more MPCCs as disclosed herein. In one aspect, the hepatocytes may be obtained from one or more human donors suffering a disorder of the liver. The kit may further comprise a culture medium as described herein, and/or additional materials or reagents for testing various biological activities of the cells in culture. For example, the kit may contain separately packaged amounts of a glucose-free medium, human serum, glucose, insulin, L-glutamine, transferrin, selenium, glucagon, dexamethasone, HEPES, a stain or dye such as but not limited to a fluorimetric dye, a lipid dye such as Nile red, and/or a cellular stain for glycogen such as PAS stain. The kit may further comprise one or more culture substrates such as a glass, silicon, or polystyrene slide or culture well, and an amount of a cell adhesion molecule. The cell adhesion molecule may be disposed according to a micropattern on the culture substrate as described herein above. Alternatively, the kit may provide an amount of the cell adhesion molecule and a PDMS stencil which can be used together to establish a micropattern as described herein on the culture substrate.

The kit may further comprise a reporter molecule or label capable of generating a signal indicative of a level of a cellular activity of interest in the hepatocytes, such as but not limited a vital dye, a lipid dye, a colorimetric agent, or a bioluminescent marker. The kit may include a detectable label such as a fluorophore, a radioactive moiety, an enzyme, a chromophore, a chemiluminescent label, or the like, and/or reagents for carrying out detectable labeling. The labels and/or reporter molecules, any calibrators and/or controls can be provided in separate containers or pre-dispensed into an appropriate assay format, for example, into microtiter plates.

It is contemplated for example that one or more of the presently disclosed co-cultures can be provided in the form of a kit with one or more containers such as vials or bottles, with each container containing a separate population of cells and/or reagents and washing reagents employed in an assay. The kit can comprise at least one container for conducting the assay, and/or a buffer, such as an assay buffer or a wash buffer, either one of which can be provided as a concentrated solution, a substrate solution for the detectable or a stop solution. The kit may comprise all components, e.g., reagents, standards, buffers, diluents, etc., which are necessary to perform the assay. The kit may contain instructions for determining the presence or amount of any metabolite, biomarker, label, or reporter of interest in the co-culture, in paper form or computer-readable form, such as a disk, CD, DVD, or the like, and/or may be made available online.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme cofactors, enzyme substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. Where appropriate, the kit optionally also can contain reaction vessels, mixing vessels, and other components that facilitate the preparation of reagents or the test sample. The kit can also include one or more instruments for assisting with obtaining a test sample, such as a syringe, pipette, forceps, measured spoon, or the like.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Fabrication of micropatterned co-cultures (MPCCs) begin by first coating Type I rat tail collagen on tissue culture polystyrene plates and then patterned into circular domains using soft lithographic techniques and plasma ablation. Next primary human hepatocytes were seeded into patterned tissue culture wells and allowed to adhere to the collagen domains. To create co-cultures, supportive 3T3-J2 non-growth arrested fibroblasts or growth arrested fibroblasts were seeded 18-24 hours after seeding hepatocytes.

For growth arrested fibroblast cultures, fibroblasts were cultured until they reached 90% confluency and the treated with mitomycin C the day of seeding with micropatterned hepatocytes. Specifically, cultures were first washed with 1×PBS, to removed residual medium, and then incubated with 1 µg/ml mitomycin C in fibroblast maintenance medium (10% bovine serum, 1% penicillin/streptomycin, and high glucose DMEM) for ~4 hours in the cell culture incubator. Mitomycin C containing medium was then removed and replaced with fibroblast maintenance medium for at least 30 minutes prior to splitting and seeding fibroblasts into cultures containing patterned hepatocytes.

Example 2

MPCCs were cultured in 5 mM glucose containing maintenance medium for 2 weeks. Cultures were treated with various starvation treatments, 1 hour, 1 day, 2 days and 3 days. To start the starvation, cultures were washed once with 1×PBS, and then incubated in 5 mM glucose containing serum free medium for the specified time. This medium was also supplemented with 1% penicillin/streptomycin and 1.5% HEPES buffer. After the starvation period, cultures were then placed back in maintenance medium for 5-8 days, depending on the previous starvation period. This was continued for 4 weeks, including the initial starvation.

Figure 2A:
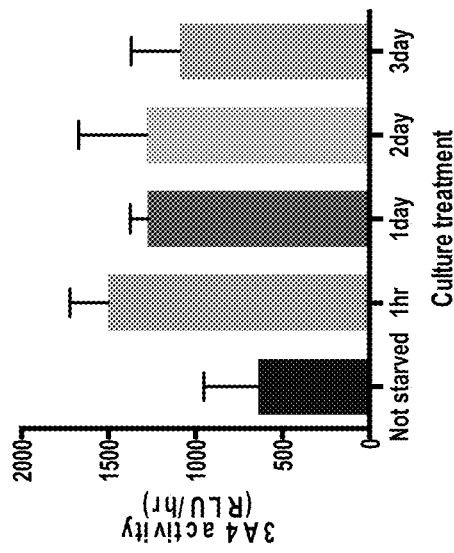
FIG. 2A depicts a graph showing the amount of CYP3A4 activity by co-cultures comprising hepatocytes and non-parenchymal cell populations wherein the composition is periodically incubated in serum-free culture medium for 1 hour, 1 day, 2 days, or 3 days and a co-culture comprising hepatocytes and non-parenchymal cell populations continually cultured in culture medium comprising serum (not starved). Error bars represent SD.

During the periodical starvation period, cultures with the various starvation treatments were assessed for changes in morphology (FIGS. 1A-E), albumin production (FIG. 1F), urea synthesis (FIG. 1G) and polarization (bile canaliculi) at the terminal 6 week time point (FIGS. 1H-1L). As another mechanism to measure hepatocyte function, drug enzyme activity levels were measured in non-starved cultures and starved cultures at the terminal 6 week time point. CYP3A4 (FIG. 2A) and CYP2A6 (FIG. 2B) enzyme activity was higher in all starvation treated cultures compared to untreated cultures. Of the starvation treatments, the 1, 2, and 3 day starvation periods had higher combined liver functions and polarization when compared to one hour starvation treatment or no starvation periods.

Example 3

MPCCs were cultured in 5 mM glucose containing maintenance medium for 2 weeks. Cultures were then washed once with 1×PBS, and then incubated in 5 mM glucose containing serum free medium for the 2 days to start the starvation treatment. After the starvation period, cultures were then placed back in maintenance medium for 5 days. This was continued for 4 weeks, including the initial starvation. A schematic of the timeline for the starvation treatment is provided in FIG. 3A. During the starvation treatment, cultures were assessed how starvation affects hepatocyte morphology, and homotypic interactions or island area using phase contrast imaging over 6 weeks in vitro (FIG. 3B). Assessments show hepatocyte island morphology and area was retained over 6 weeks in starved cultures, whereas non-starved culture island area diminished over time and typical hepatocyte morphology was lost by 6 weeks in culture (FIGS. 3C-3I).

Example 4

Figure 4C:
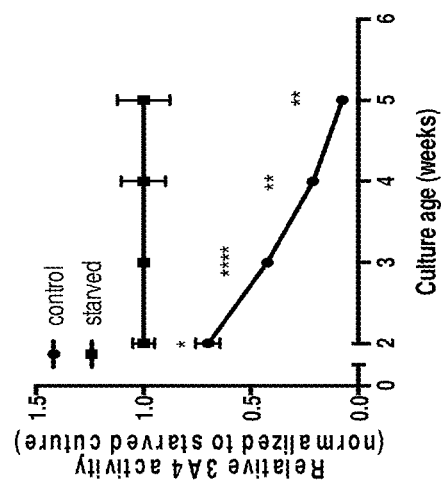
FIG. 4C depicts a graph showing the amount of CYP3A4 activity in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) over 40 days of culture. Error bars represent SEM where , *, and **** represent $p<0.01$, $p<0.001$ and $<0.0001$, respectively, assessed via t-test between non-starved and starved cultures.
Figure 4B:
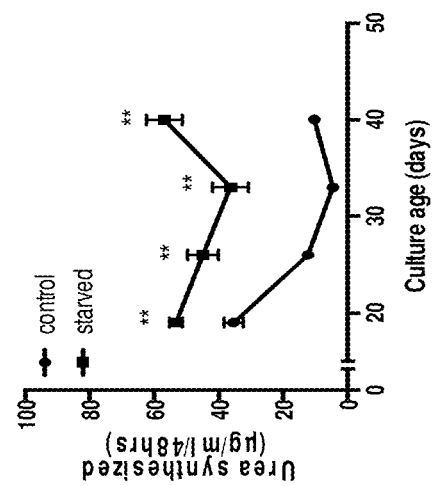
FIG. 4B depicts a graph showing the amount of urea produced in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) over 40 days of culture. Error bars represent SEM where , *, and **** represent $p<0.01$, $p<0.001$ and $<0.0001$, respectively, assessed via t-test between non-starved and starved cultures.
Figure 4A:
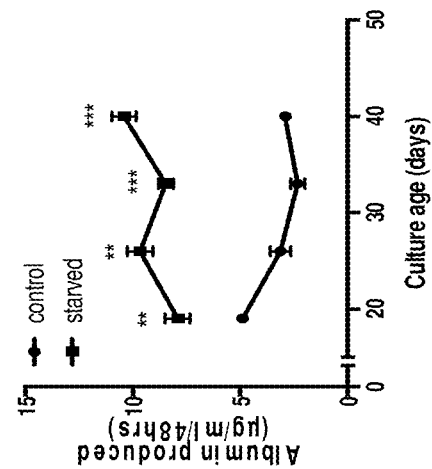
FIG. 4A depicts a graph showing the amount of albumin produced in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) over 40 days of culture. Error bars represent SEM where , *, and **** represent $p<0.01$, $p<0.001$ and $<0.0001$, respectively, assessed via t-test between non-starved and starved cultures.

MPCCs were cultured in 5 mM glucose containing maintenance medium for 2 weeks. Cultures were then washed once with 1×PBS, and then incubated in 5 mM glucose containing serum free medium for the 2 days to start the starvation treatment. After the starvation period, cultures were then placed back in maintenance medium for 5 days. This was continued for 4 weeks, including the initial starvation. Albumin production (FIG. 4A) and urea synthesis (FIG. 4B) were higher in starved cultures compared to non-starved cultures, indicating that starvation increases hepatocyte function in MPCCs.

Figure 5A:
FIG. 5A depicts a graph showing the amount of CYP2A6 activity in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) at 2, 3, 4, and 6 weeks of culture. Error bars represent SD.
Figure 5B:
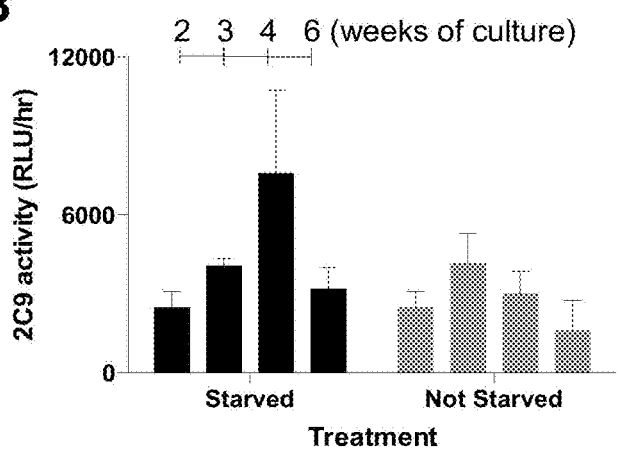
FIG. 5B depicts a graph showing the amount of CYP2C9 activity in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) at 2, 3, 4, and 6 weeks of culture. Error bars represent SD.
Figure 5C:
FIG. 5C depicts a graph showing the amount of CYP1A2 activity in co-cultures comprising hepatocytes and non-parenchymal cell populations wherein the composition is periodically incubated in serum-free culture medium and co-cultures comprising hepatocytes and non-parenchymal cell populations continually cultured in culture medium comprising serum (non-starved) at 2, 3, 4, and 6 weeks of culture. Error bars represent SD.

As another mechanism to measure hepatocyte function, drug enzyme activity levels were measured in in starved and non-starved cultures over time. CYP3A4 activity was ~5 fold higher in starved cultures (FIG. 4C), CYP2A6 enzyme activity was ~2 fold higher in starved cultures (FIG. 5A), CYP2C9 enzyme activity was ~2 fold higher in starved cultures (FIG. 5B), and CYP1A2 enzyme activity was ~1 fold higher in starved cultures (FIG. 5C) when compared over 4 weeks of culture to non-starved cells at 4 weeks of culture.

Additionally, after 6 weeks of culture, hepatocyte polarization was quantified by measuring the amount of fluorescent transporter specific dye excreted in non-starved and starved cultures (FIGS. 4E-4F). In starved cultures, hepatocyte polarization was four fold higher than non-starved cultures (FIG. 4D). This was correlated with an increase in total phosphorylated adenosine monophosphate activated kinase (p-AMPK), which is implicated in maintaining hepatocyte polarity (FIG. 4G). These results suggest that periodic starvation helps retain hepatocyte functions and polarization over time.

Example 5

Pure hepatocyte cultures were created by first diluting Type I rat tail collagen in molecular grade water to achieve a final concentration of 100 μg/ml and then adding to tissue culture polystyrene plates and incubating for 2 hours at 37° C. Coated wells were washed with water twice and dried prior to seeding primary human hepatocytes. Hepatocytes were seeded at a density of 1.16 million cells/mL, and cultures were switched to their respective conditions after seeding for 4 hours.

Example 6

Figure 6C:
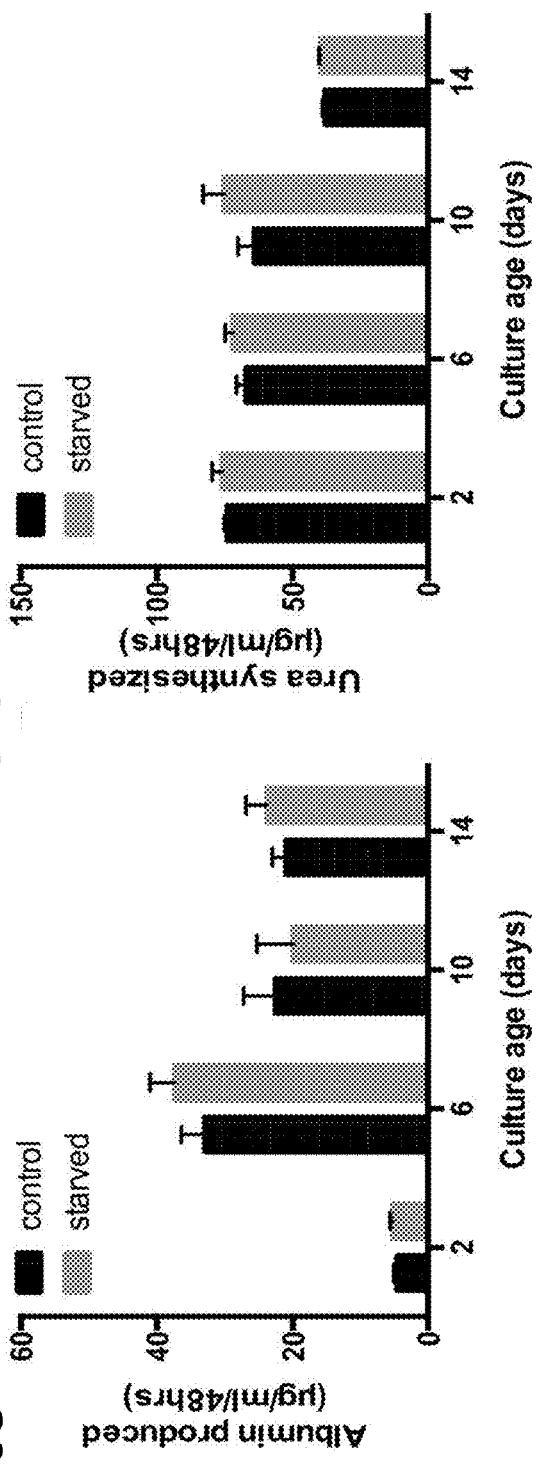
FIG. 6C depicts a graph showing the amount of albumin produced in MPCCs comprising hepatocytes wherein the composition is periodically incubated in serum-free culture medium and MPCCs comprising hepatocytes continually cultured in culture medium comprising serum (non-starved) after 14 days of culture. Error bars represent SD.
Figure 6D:
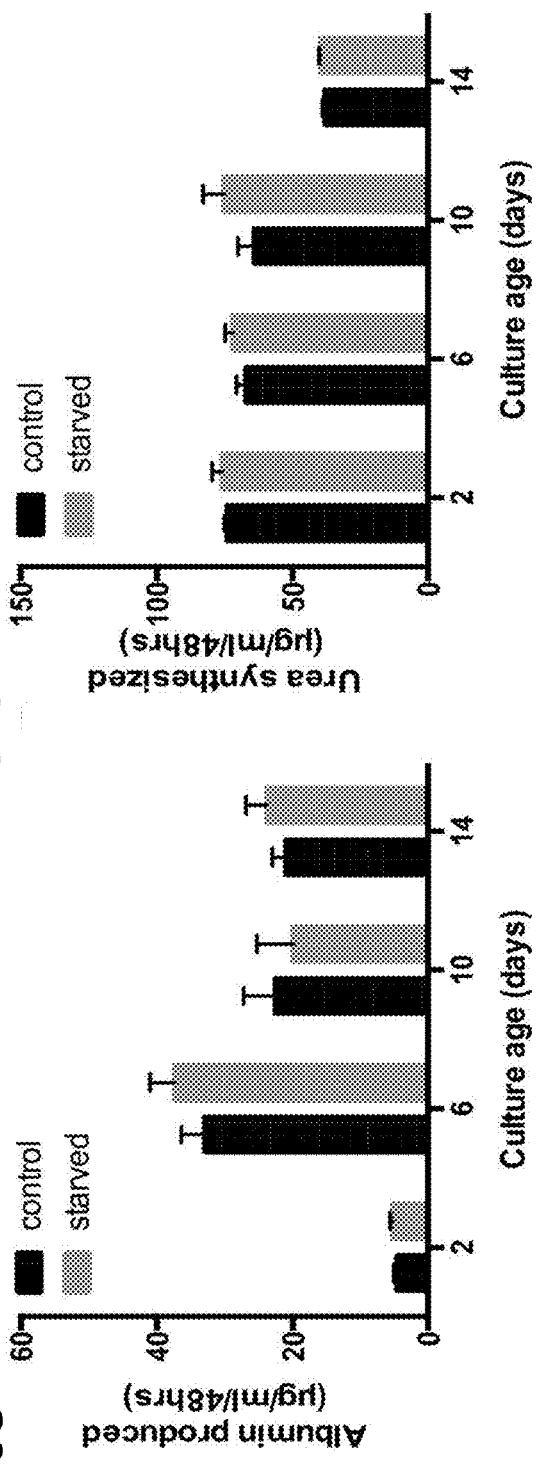
FIG. 6D depicts a graph showing the amount of urea produced in MPCCs comprising hepatocytes wherein the composition is periodically incubated in serum-free culture medium and MPCCs comprising hepatocytes continually cultured in culture medium comprising serum (non-starved) after 14 days of culture. Error bars represent SD.
Figure 6E:
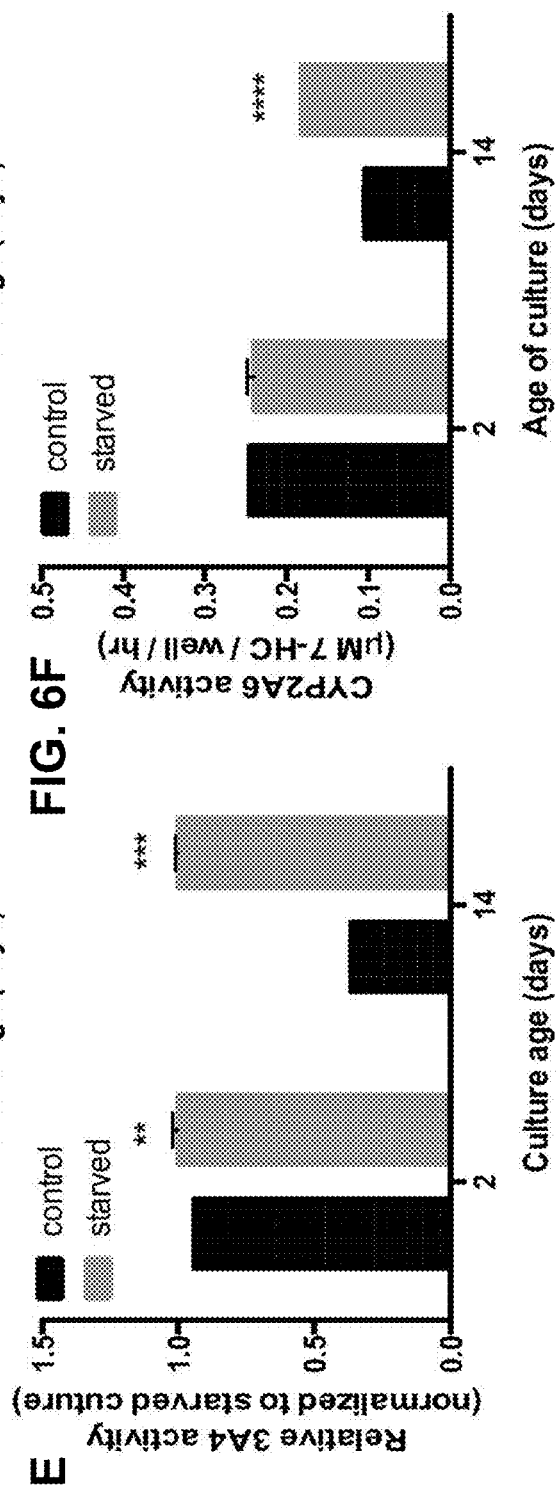
FIG. 6E depicts a graph showing the amount of CYP3A4 enzyme activity in MPCCs comprising hepatocytes wherein the composition is periodically incubated in serum-free culture medium and MPCCs comprising hepatocytes continually cultured in culture medium comprising serum (non-starved) after 14 days of culture. Error bars represent SD.
Figure 6F:
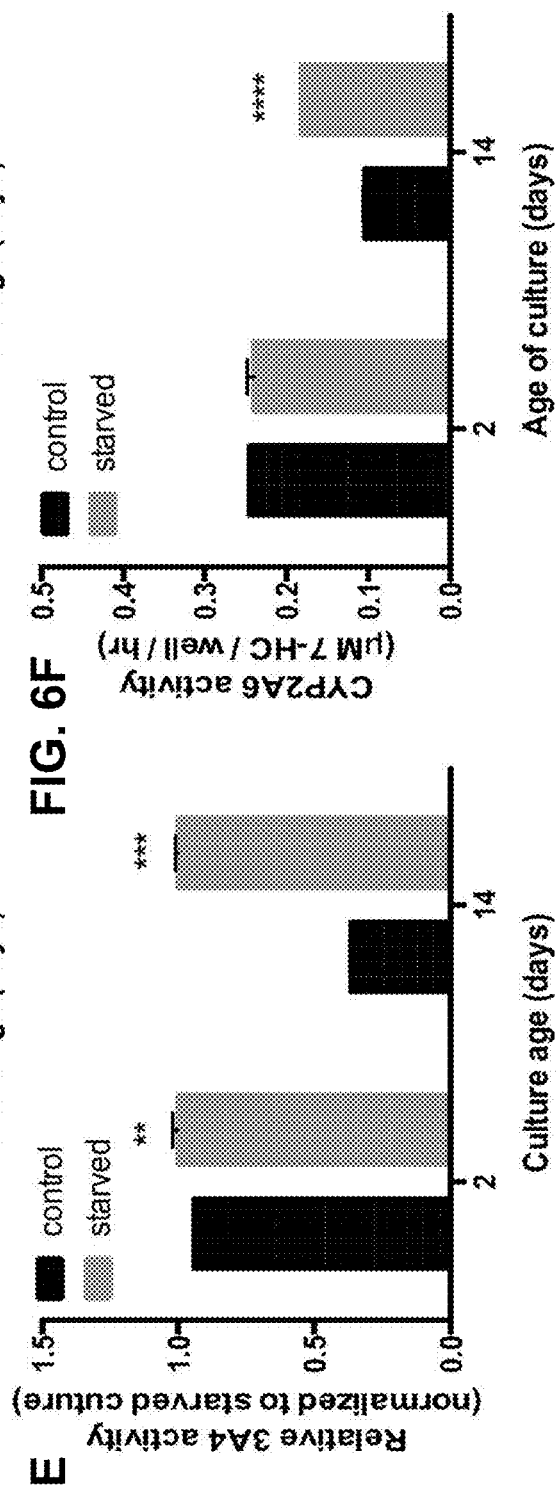
FIG. 6F depicts a graph showing the amount of CYP2A6 enzyme activity in MPCCs comprising hepatocytes wherein the composition is periodically incubated in serum-free culture medium and MPCCs comprising hepatocytes continually cultured in culture medium comprising serum (non-starved) after 14 days of culture.
Figure 6G:
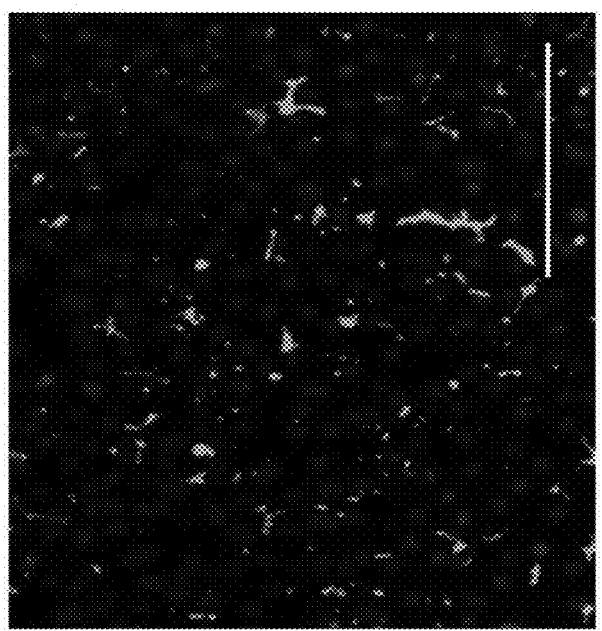
FIGS. 6G-6H depicts images of MPCCs comprising hepatocytes wherein the composition is periodically incubated in serum-free culture medium (FIG. 6H) and MPCCs comprising hepatocytes continually cultured in culture medium comprising serum (non-starved) (FIG. 6G) after 14 days of culture wherein bile canaliculi was assessed using CDCFDA fluorescent staining (green) and Hoechst 33342 (blue) to visualize cell nuclei. Scale bars represent 400 µm.
Figure 6H:
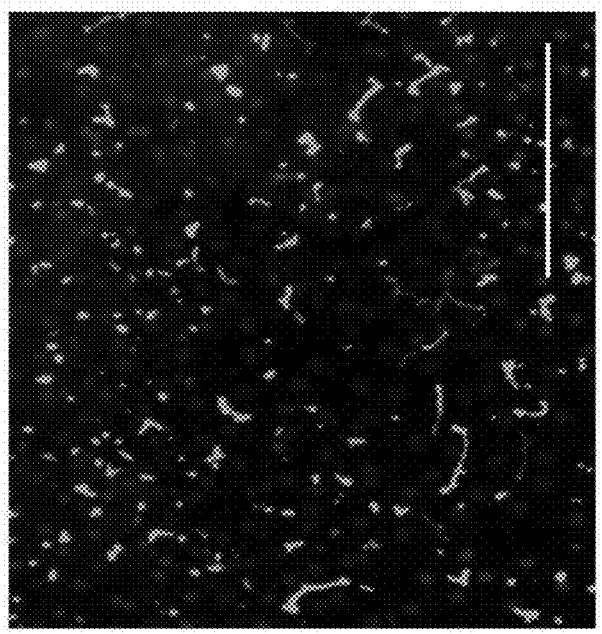

For pure culture studies, hepatocytes were switched to hepatocyte maintenance medium after 4 hours of seeding. Cultures were starved 2 days later and every 2 days after that for a total of 14 days of culture. During the periodical starvation period, cultures were assessed at day 14 of for morphological changes (FIG. 6B) and compared to non-starved cultures (FIG. 6A). Additionally, albumin production (FIG. 6C), urea synthesis (FIG. 6D), CYP3A4 enzyme activity (FIG. 6E) and CYP2A6 (FIG. 6F) were quantified over time as measures of hepatocyte function. Hepatocyte polarization (bile canaliculi), assessed via fluorescent dye excretion, was assessed in starved and non-starved cultures after 2 weeks of culture (FIGS. 6G-6H). Results show a slight increase in albumin production and urea synthesis and a significant increase in CYP3A4 and CYP 2A6 enzyme activity in starved cultures compared to non-starved cultures. Further, starvation treatment enhanced hepatocyte bile canaliculi formation in starved cultures compared to non-starved cultures.

Example 7

To gain mechanistic insight into the potential impact of AMPK activation on retaining hepatocyte functions and polarization, the effects of pharmacologic AMPK activation in the absence of starvation was assessed. Specifically, MPCCs were periodically treated with metformin, an AMPK activator, during the normal starvation period every week for 4 weeks in serum-containing medium. Metformin treated MPCCs had 1.7, 1.5 and 1.6 fold higher levels of CYP3A4 activity (FIG. 7C), as well as albumin (FIG. 7A) and urea production (FIG. 7B), respectively, over time when compared to non-starved cultures. These functional markers were significantly higher in metformin treated cultures than control cultures; however, the magnitude was still below starved culture levels. Importantly, hepatocyte island area (FIGS. 7F-7H) and polarization (FIGS. 7I-7K) were not significantly higher in metformin treated versus non-starved control MPCCs. These results suggest that periodic starvation may prolong hepatocyte functions by increasing AMPK activation, however, the long-term maintenance of hepatocyte homotypic interactions and polarization requires other factors obtained through starvation.

Example 8

Figure 9B:
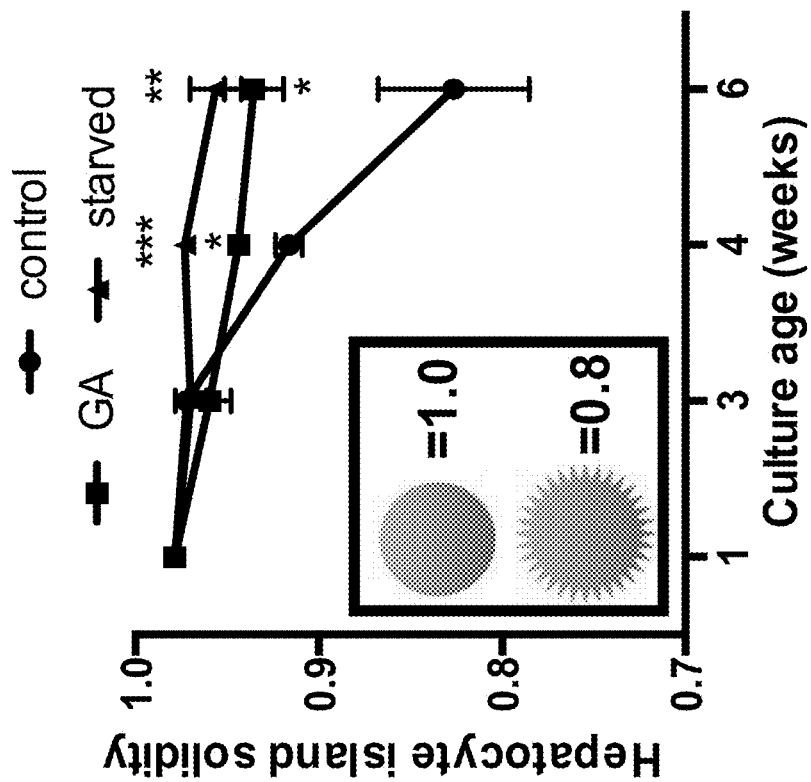
FIG. 9B depicts a graph showing the solidity of hepatocyte islands in co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) after 4 weeks of culture whereby the solidity of hepatocyte islands is measured by dividing the island area by the convex hull area. Error bars represent SEM were *,  and * represent $p<0.05$, $p<0.01$ and $<0.001$, respectively, assessed via one way ANOVA across treatments.
Figure 9A:
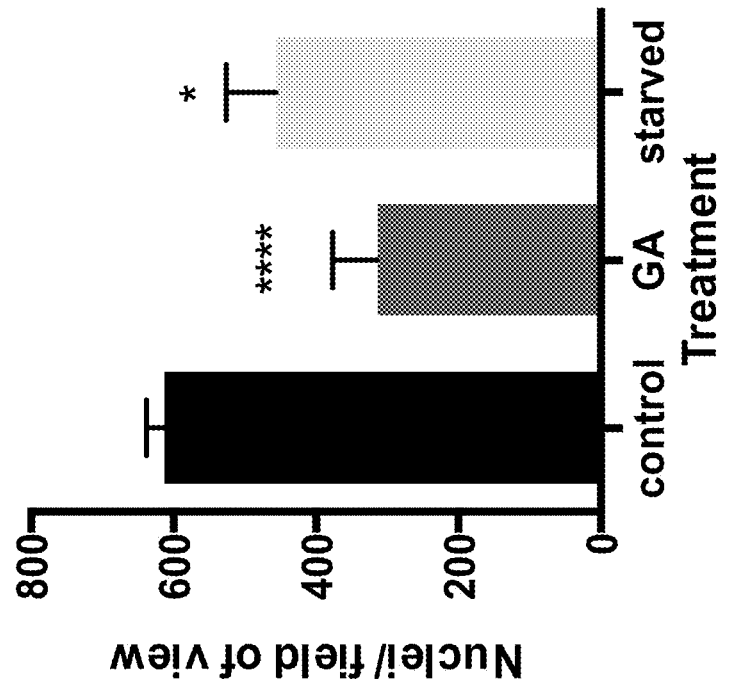
FIG. 9A depicts a graph showing the number of non-parenchymal cells (fibroblasts) between hepatocyte islands of co-cultures comprising hepatocytes and non-parenchymal cell populations wherein the composition is periodically incubated in serum-free culture medium (starved), co-cultures comprising hepatocytes and non-parenchymal cell populations wherein the non-parenchymal cells (fibroblasts) are growth arrested (GA), and co-cultures comprising hepatocytes and non-parenchymal cell populations continually cultured in culture medium comprising serum (control) after 4 weeks of culture. Error bars represent SEM where *,  and * represent $p<0.05$, $p<0.01$ and $<0.001$, respectively, assessed via one way ANOVA across treatments.
Figure 10:
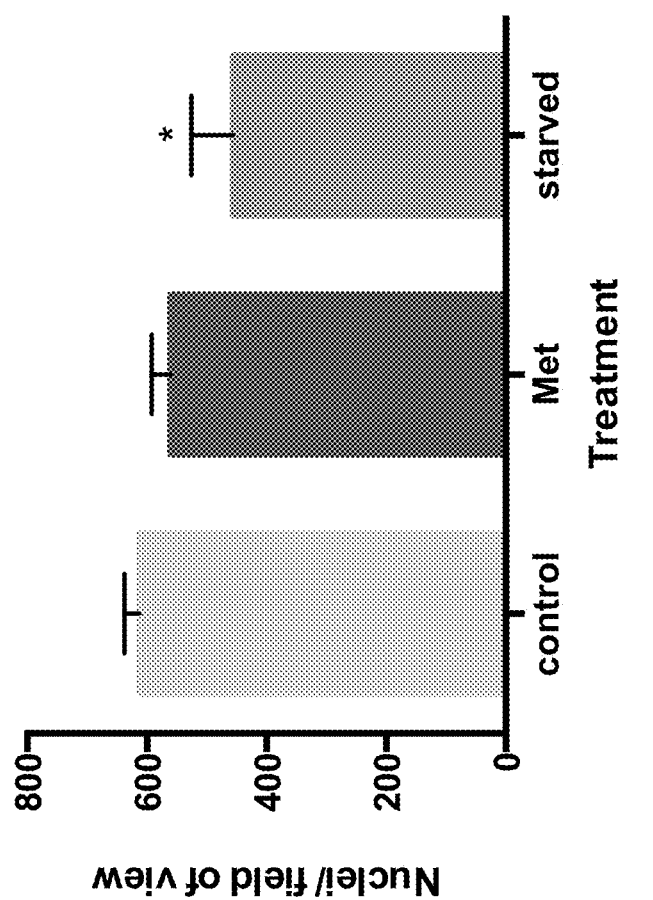
FIG. 10 depicts a graph showing the fibroblast density, assessed via live cell imaging of nuclei using Hoechst 33342 staining, of non-parenchymal cells (fibroblasts) in co-cultures comprising hepatocytes and non-parenchymal cell populations wherein the composition is periodically incubated in serum-free culture medium (starved), co-cultures comprising hepatocytes and non-parenchymal cell populations wherein the composition is periodically incubated in serum-free culture medium in the presence of metformin (met), and co-cultures comprising hepatocytes and non-parenchymal cell populations continually cultured in culture medium comprising serum (control) after 4 weeks of culture. Error bars represent SD where * represents $p<0.05$, assessed via one way ANOVA across treatments.
Figure 11F:
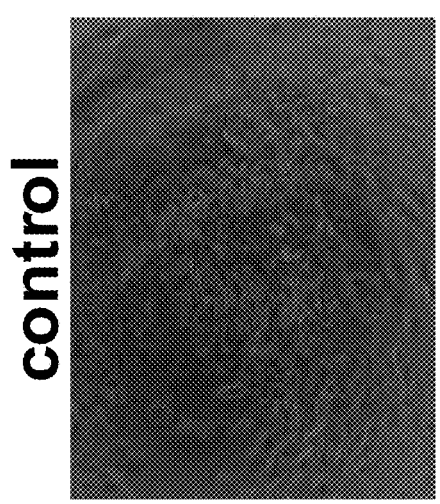
FIGS. 11F-11H depicts images of co-cultures comprising hepatocytes wherein the composition is periodically incubated in serum-free culture medium (starved) (FIG. 11H), co-cultures comprising hepatocytes and non-parenchymal cell populations wherein the non-parenchymal cells (fibroblasts) are growth arrested (GA) (FIG. 11G), and co-cultures comprising hepatocytes and non-parenchymal cell populations continually cultured in culture medium comprising serum (control) (FIG. 11F) after 6 weeks of culture. Scale bars represent 400 µm.
Figure 11G:
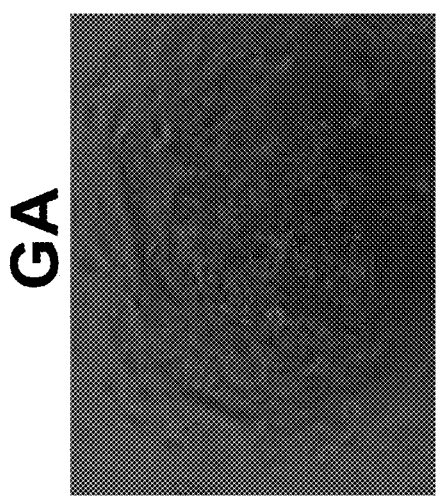
Figure 11H:
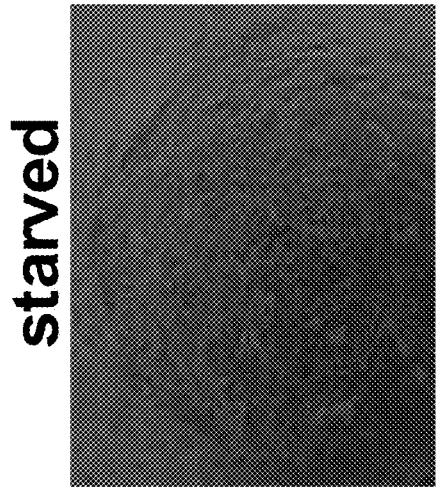
Figure 11I:
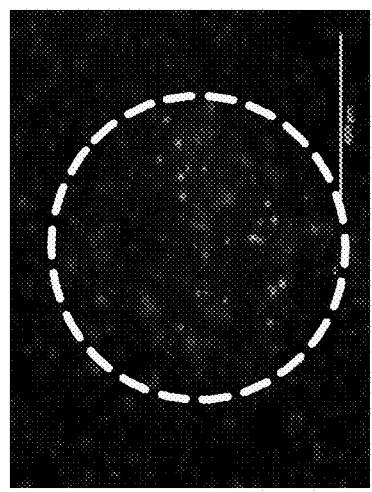
FIGS. 11I-11K depicts images of co-cultures comprising hepatocytes wherein the composition is periodically incubated in serum-free culture medium (starved) (FIG. 11K), co-cultures comprising hepatocytes and non-parenchymal cell populations wherein the non-parenchymal cells (fibroblasts) are growth arrested (GA) (FIG. 11J), and co-cultures comprising hepatocytes and non-parenchymal cell populations continually cultured in culture medium comprising serum (control) (FIG. 11I) after 6 weeks of culture wherein bile canaliculi was assessed using CDCFDA fluorescent staining (green) and Hoechst 33342 (blue) to visualize cell nuclei. Circles outline hepatocyte islands and scale bars represent 400 µm.
Figure 11J:
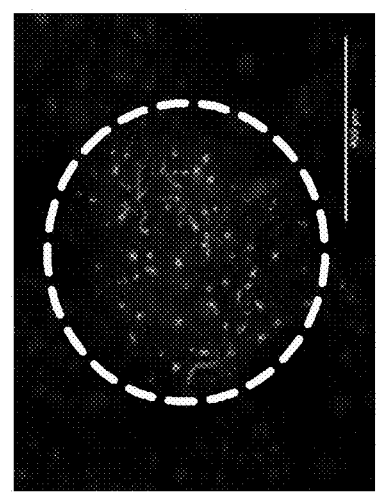
Figure 11K:
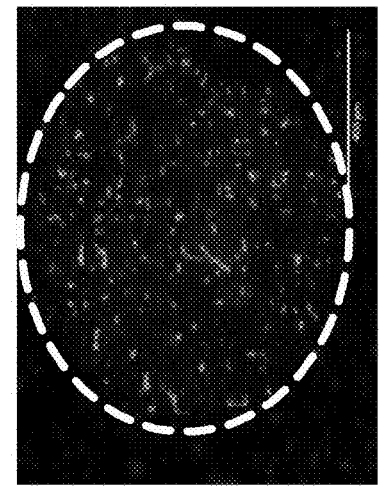

Besides the hepatocyte specific changes noted with starvation, changes were also observed in fibroblast morphology during starvation and subsequent density after starvation (FIGS. 8A-8B). During starvation, some supportive fibroblasts assume a rounded, rather than spread, morphology, which suggested that fibroblasts might detach during the serum starvation, and accordingly fibroblast DNA was reduced by ~4 fold after starvation (FIG. 8C). Supporting this, the number of fibroblasts between hepatocyte islands after starvation were also lower (FIG. 9A). Fibroblast numbers did not change in metformin treated MPCCs (FIG. 10). These results suggest that the starvation protocol reduces fibroblast numbers over time, and led to the hypothesis that preventing fibroblast overgrowth might have effects on maintaining hepatocyte polarization.

To assess the effects of reduced fibroblast numbers on hepatocyte alone, fibroblasts were growth arrested using mitomycin C prior to incorporation into MPCCs. The effects of growth arrested fibroblasts on hepatocytes were assessed without serum starvations. Fibroblast numbers between hepatocyte islands were significantly reduced compared to non-starved cultures (FIG. 9A). Importantly, the solidity of hepatocyte islands, measured by dividing the island area by the convex hull area, was significantly higher in MPCCs with growth arrested fibroblasts and starved cultures (FIG. 9B). In control cultures, homotypic interactions and the maintenance of the hepatocyte island shape is gradually lost over time (FIGS. 9D-9F), while this is maintained in starved cultures (FIGS. 9J-9L) or cultures with growth arrested fibroblasts (FIGS. 9G-9I). Supporting these findings, MPCCs with growth arrested fibroblasts had on average 2, 1.5 and 1.5 fold higher levels of CYP3A4 activity (FIG. 11C), as well as albumin (FIG. 11A) and urea production (FIG. 11B), respectively, over time when compared to non-starved cultures. Importantly, hepatocyte polarity was significantly retained in MPCCs with growth-arrested fibroblasts to a similar level as starved cultures (FIG. 11E and FIGS. 11I-11K), while hepatocyte island area was still lost over time (FIG. 11D and FIGS. 11F-11H). These results suggest that preventing fibroblast overgrowth with periodic starvation may prolong hepatocyte functions by maintaining an optimal level of fibroblasts in culture and preventing their disruption of hepatocyte homotypic interactions.

Example 9

Figure 12A:
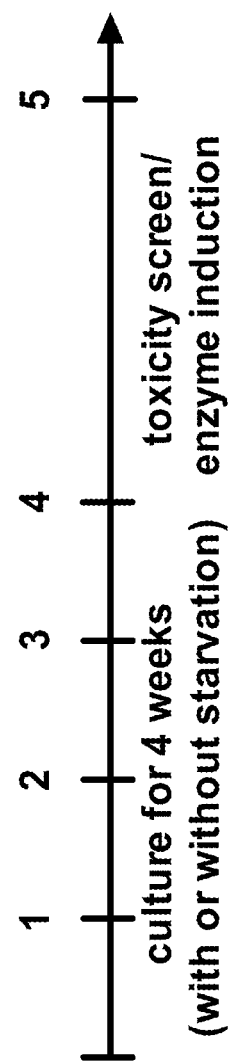
FIG. 12A depicts a schematic of the timeline used to periodically serum-starve MPCCs comprising hepatocytes and non-parenchymal cell populations for 4 weeks before adding 5 toxins and 5 non-toxins for drug toxicity screening.

To assess the potential utility of the starvation protocol for drug toxicity screening after prolonged culture, we treated starved and non-starved MPCCs with 5 toxins and 5 non-toxins after 3 weeks of starvation (time line provided in FIG. 12A). To prevent potential drug-protein interactions, cultures were dosed with compounds in serum free medium. Cultures were treated 3 times over a period of 6 days (i.e. every 2 days), with multiples of the maximum concentration observed in the blood after administration to humans, Cmax. Specifically, cultures were treated with 25*Cmax, 100*Cmax or a vehicle, dimethyl sulfoxide (DMSO), control. Albumin and urea production were used to identify hepatospecific toxicity since fibroblast ATP cannot be distinguished from hepatocyte ATP and could therefore show non-specific toxicity of cultures. Additionally, albumin and urea have been shown to be more sensitive markers of hepatotoxicity than ATP in micropatterned co-cultures. Accordingly, when albumin or urea levels dropped below 50% of the DMSO control, the compound was considered toxic, and the toxic concentration that reduced the response by 50% (TC50) was interpolated from the dose response curves between DMSO and 25*Cmax, if the latter value fell below 50%, or between 25*Cmax and 100*Cmax, and graphed.

Figure 12B:
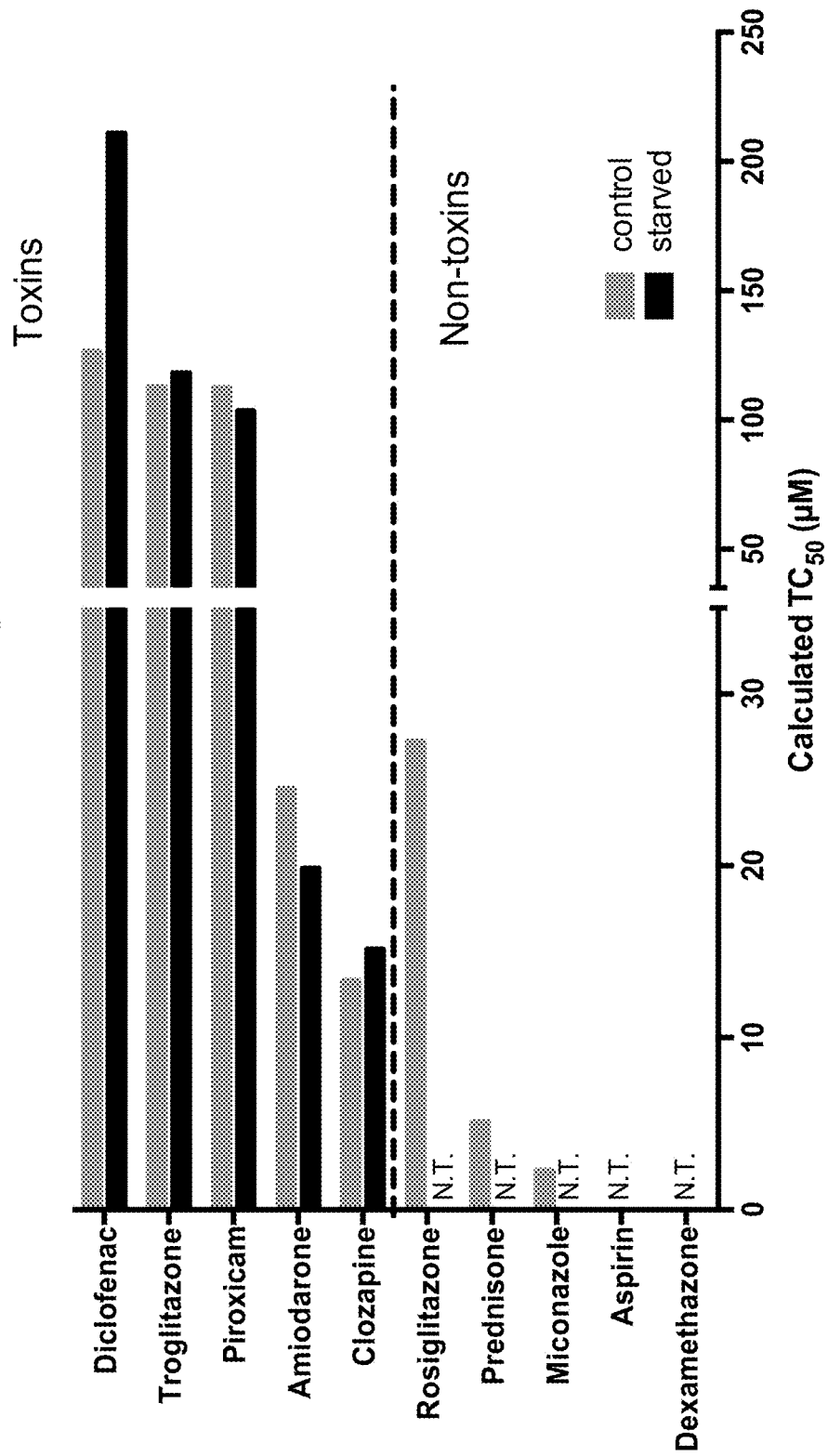
FIG. 12B depicts a graph showing the $TC_{50}$ values for albumin production from co-cultures comprising hepatocytes and non-parenchymal cell populations wherein the composition is periodically incubated in serum-free culture medium (starved) and co-cultures comprising hepatocytes and non-parenchymal cell populations continually cultured in culture medium comprising serum (control) after co-cultures were treated with toxins—diclofenac, troglitazone, piroxicam, amiodarone, or clozapine, or non-toxins—rosiglitazone, prednisone, miconazole, aspirin, and dexamethasone. N.T. represents not toxic. Error bars represent SD.
Figure 12C:
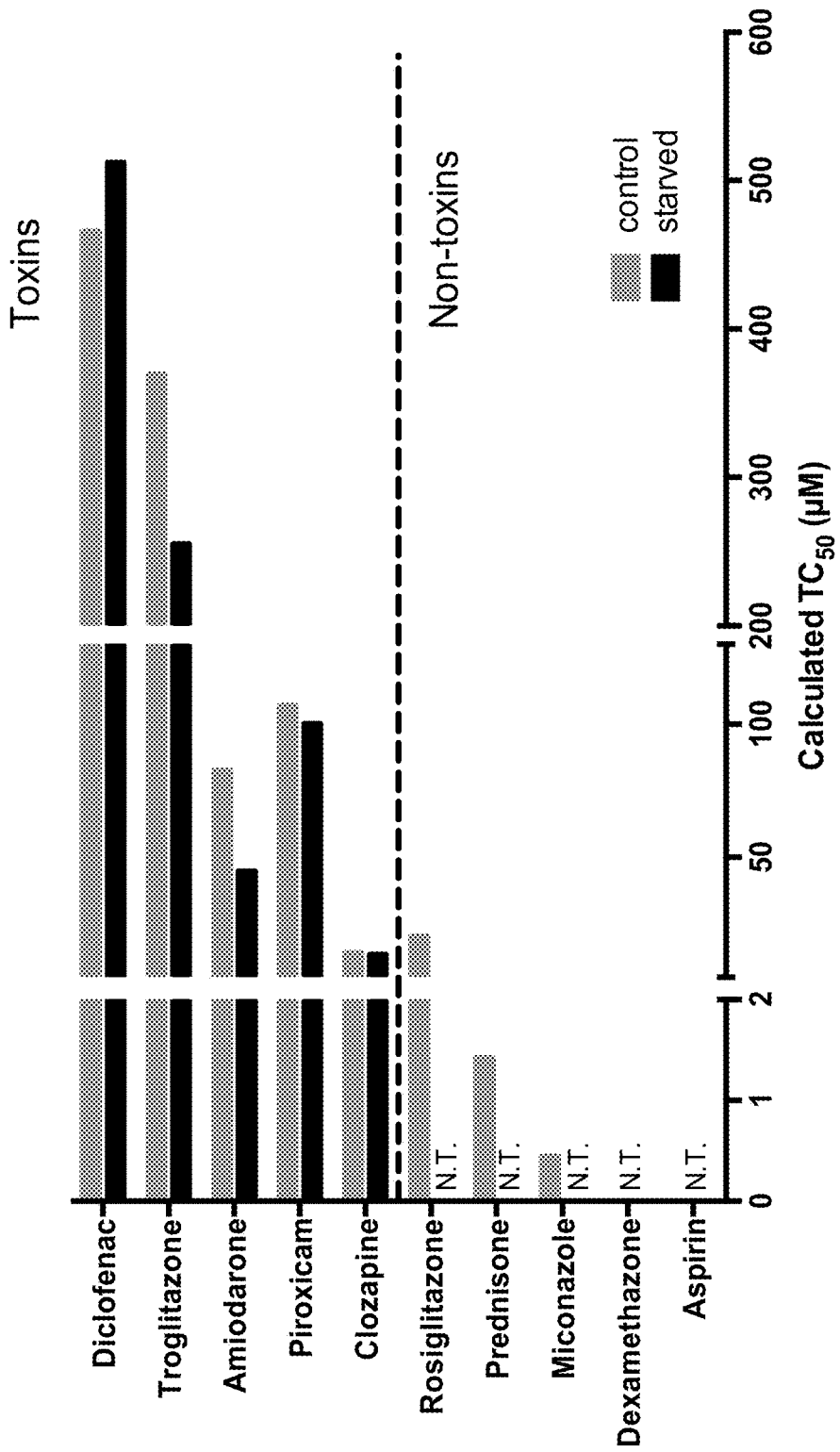
FIG. 12C depicts a graph showing the $TC_{50}$ values for urea synthesis from co-cultures comprising hepatocytes and non-parenchymal cell populations wherein the composition is periodically incubated in serum-free culture medium (starved) and co-cultures comprising hepatocytes and non-parenchymal cell populations continually cultured in culture medium comprising serum (control) after co-cultures were treated with toxins—diclofenac, troglitazone, piroxicam, amiodarone, or clozapine, or non-toxins—rosiglitazone, prednisone, miconazole, aspirin, and dexamethasone. N.T. represents not toxic. Error bars represent SD.
Figure 13A:
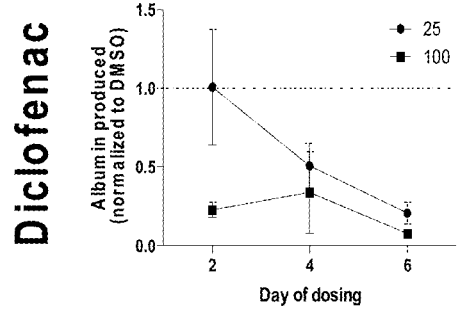
FIGS. 13A-13E depict graphs showing the amount of albumin produced from co-cultures comprising hepatocytes and non-parenchymal cell populations continually cultured in culture medium comprising serum after co-cultures were treated with 25 nM or 100 nM of toxins diclofenac (FIG. 13A), troglitazone (FIG. 13B), amiodarone (FIG. 13C), clozapine (FIG. 13D), and piroxicam (FIG. 13E) for 2, 4, and 6 days. Error bars are SD. All data was normalized to the vehicle, DMSO, control.
Figure 13B:
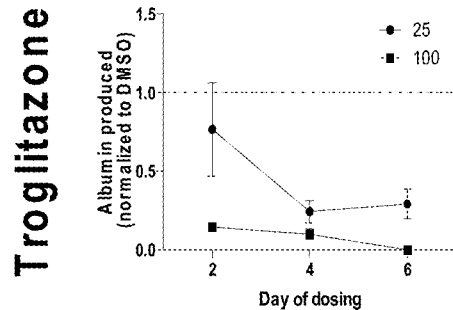
Figure 13C:
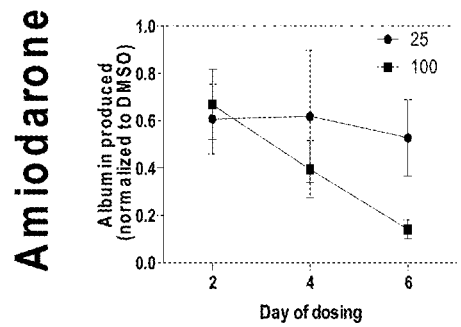
Figure 13D:
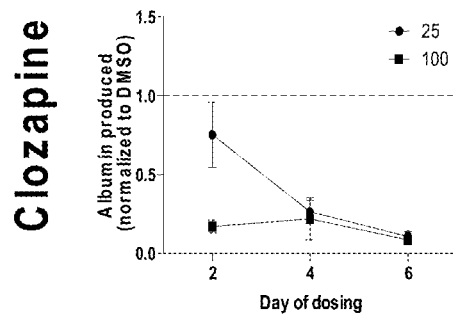
Figure 13E:
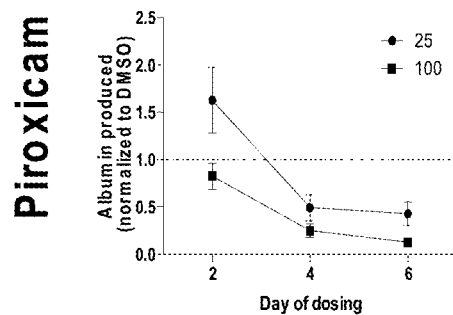
Figure 13F:
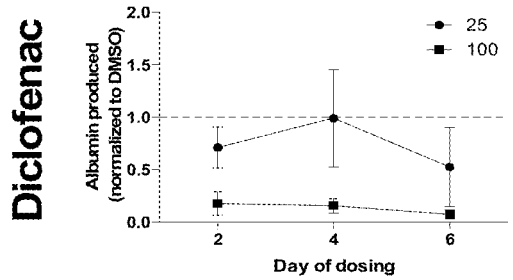
FIGS. 13F-13J depict graphs showing the amount of albumin produced from co-cultures comprising hepatocytes and non-parenchymal cell populations periodically incubated in serum-free culture medium (starved) after co-cultures were treated with 25 nM or 100 nM of toxins diclofenac (FIG. 13F), troglitazone (FIG. 13G), amiodarone (FIG. 13H), clozapine (FIG. 13I), and piroxicam (FIG. 13J) for 2, 4, and 6 days. Error bars are SD. All data was normalized to the vehicle, DMSO, control.
Figure 13G:
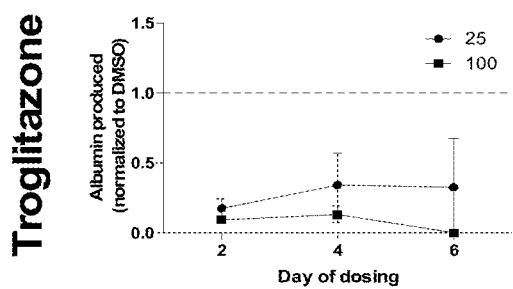
Figure 13H:
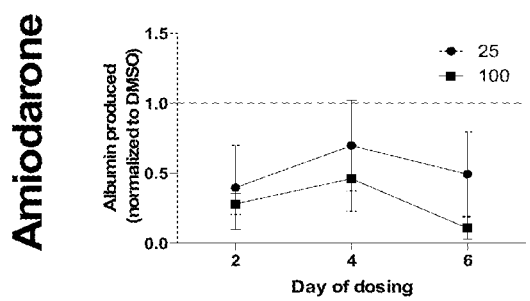
Figure 13I:
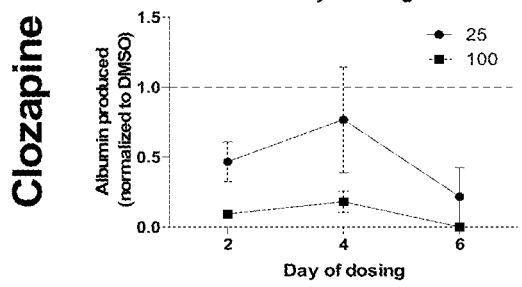
Figure 13J:
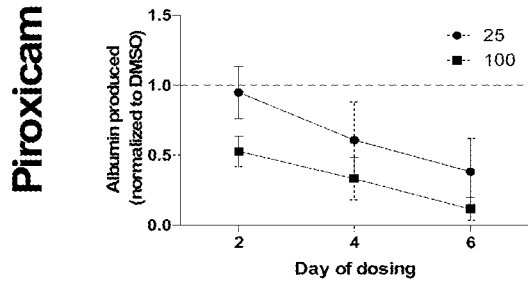
Figure 14A:
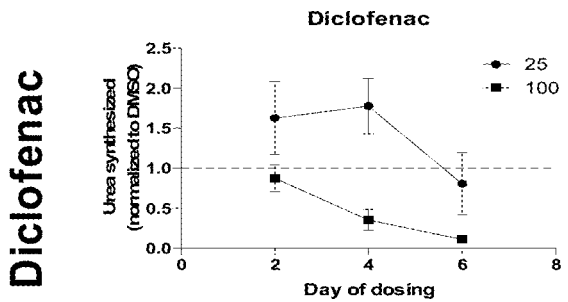
FIGS. 14A-14E depict graphs showing the amount of urea produced from co-cultures comprising hepatocytes and non-parenchymal cell populations continually cultured in culture medium comprising serum after co-cultures were treated with 25 nM or 100 nM of toxins diclofenac (FIG. 14A), troglitazone (FIG. 14B), amiodarone (FIG. 14C), clozapine (FIG. 14D), and piroxicam (FIG. 14E) for 2, 4, and 6 days. Error bars are SD. All data was normalized to the vehicle, DMSO, control.
Figure 14B:
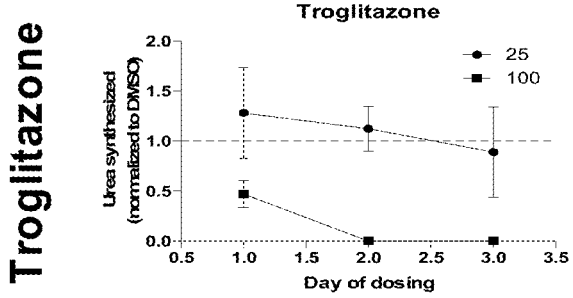
Figure 14C:
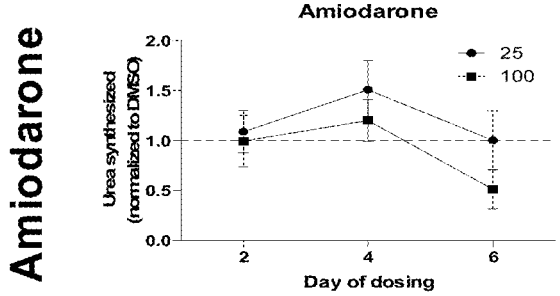
Figure 14D:
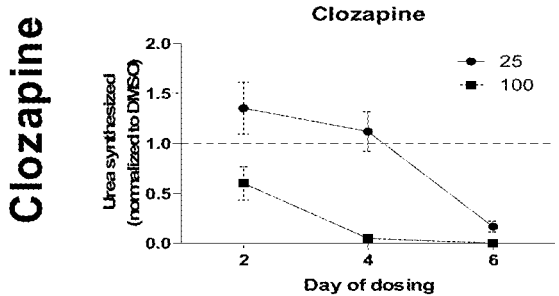
Figure 14E:
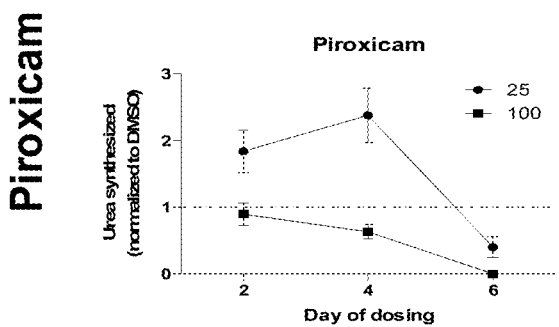
Figure 14F:
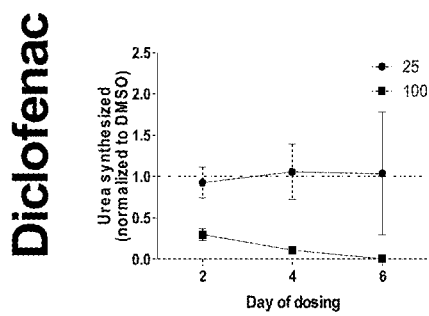
FIGS. 14F-14J depict graphs showing the amount of urea produced from co-cultures comprising hepatocytes and non-parenchymal cell populations periodically incubated in serum-free culture medium (starved) after co-cultures were treated with 25 nM or 100 nM of toxins diclofenac (FIG. 14F), troglitazone (FIG. 14G), amiodarone (FIG. 14H), clozapine (FIG. 14I), and piroxicam (FIG. 14J) for 2, 4, and 6 days. Error bars are SD. All data was normalized to the vehicle, DMSO, control.
Figure 14G:
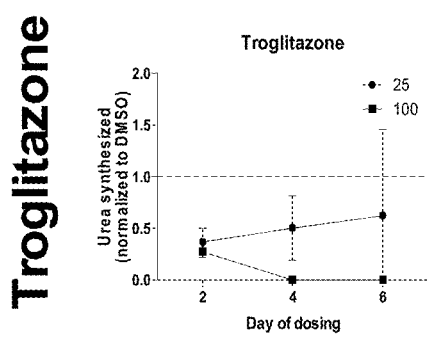
Figure 14H:
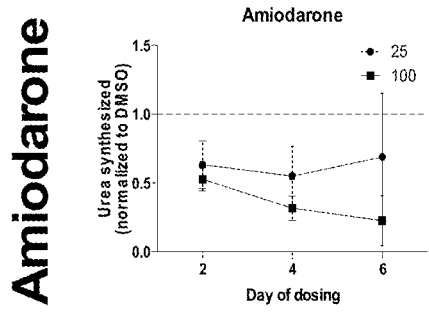
Figure 14I:
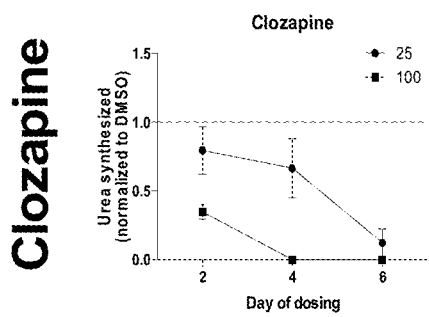
Figure 14J:
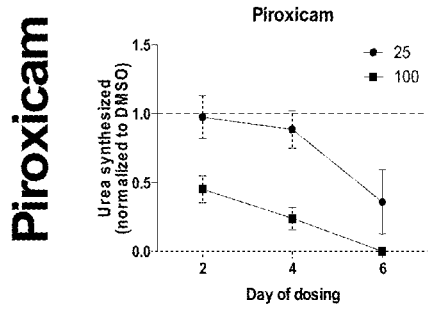

To screen for toxicity, starved or non-starved cultures were treated with compounds that have been extensively shown to be hepatotoxins. Using toxic compounds can assess the sensitivity of the system to identify toxic and non-toxic compounds. Sensitivity is calculated by dividing the total number of compounds identified as toxic by the total number of toxic compounds tested. Diclofenac, troglitazone, piroxicam, amiodarone and clozapine are considered liver toxins. The TC50 values for albumin production in non-starved cells treated with diclofenac (FIG. 12B and FIG. 13A), troglitazone (FIG. 12B and FIG. 13B), piroxicam (FIG. 12B and FIG. 13E), amiodarone (FIG. 12B and FIG. 13C) and clozapine (FIG. 12B and FIG. 13D) were similar to the TC50 values for albumin production in starved cells treated with diclofenac (FIG. 12B and FIG. 13F), troglitazone (FIG. 12B and FIG. 13G), piroxicam (FIG. 12B and FIG. 13J), amiodarone (FIG. 12B and FIG. 13H) and clozapine (FIG. 12B and FIG. 13I). The TC50 values for urea production in non-starved cells treated with diclofenac (FIG. 12C and FIG. 14A), troglitazone (FIG. 12C and FIG. 14B), piroxicam (FIG. 12C and FIG. 14E), amiodarone (FIG. 12C and FIG. 14C) and clozapine (FIG. 12C and FIG. 14D) were similar to the TC50 values for urea production in starved cells treated with diclofenac (FIG. 12C and FIG. 14F), troglitazone (FIG. 12C and FIG. 14G), piroxicam (FIG. 12C and FIG. 14J), amiodarone (FIG. 12C and FIG. 14H) and clozapine (FIG. 12C and FIG. 14I). TC50 values for urea were higher than the values obtained for albumin, regardless of culture treatment. These results suggest that starved and non-starved cultures have a high level of sensitivity.

Figure 13K:
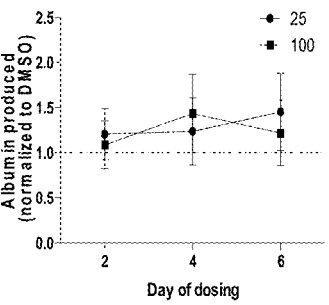
FIGS. 13K-13O depict graphs showing the amount of albumin produced from co-cultures comprising hepatocytes and non-parenchymal cell populations continually cultured in culture medium comprising serum after co-cultures were treated with 25 nM or 100 nM of non-toxins aspirin (FIG. 13K), dexamethasone (FIG. 13L), rosiglitazone (FIG. 13M), prednisone (FIG. 13N) and miconazole (FIG. 13O), for 2, 4, and 6 days. Error bars are SD. All data was normalized to the vehicle, DMSO, control. Error bars are SD. All data was normalized to the vehicle, DMSO, control.
Figure 13L:
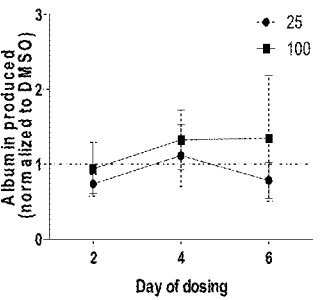
Figure 13M:
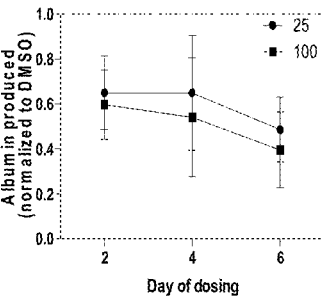
Figure 13N:
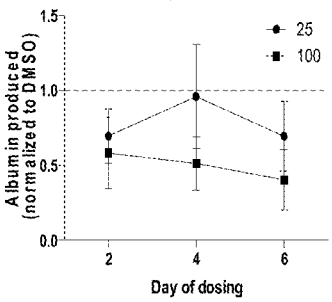
Figure 13O:
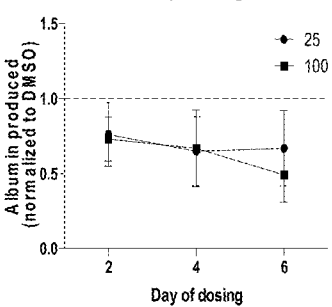
Figure 13P:
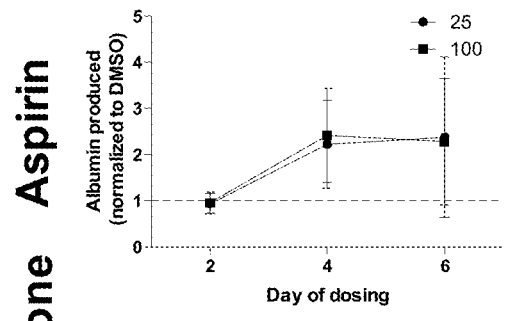
FIGS. 13P-13T depict graphs showing the amount of albumin produced from co-cultures comprising hepatocytes and non-parenchymal cell populations periodically incubated in serum-free culture medium (starved) after co-cultures were treated with 25 nM or 100 nM of non-toxins aspirin (FIG. 13P), dexamethasone (FIG. 13Q), rosiglitazone (FIG. 13R), prednisone (FIG. 13S) and miconazole (FIG. 13T), for 2, 4, and 6 days. Error bars are SD. All data was normalized to the vehicle, DMSO, control. Error bars are SD. All data was normalized to the vehicle, DMSO, control.
Figure 13Q:
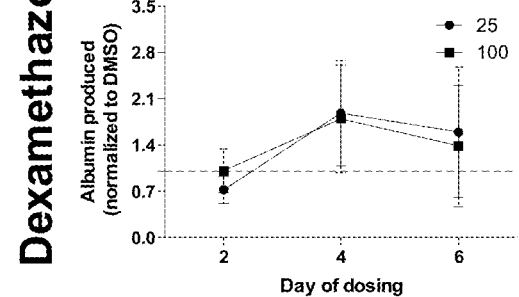
Figure 13R:
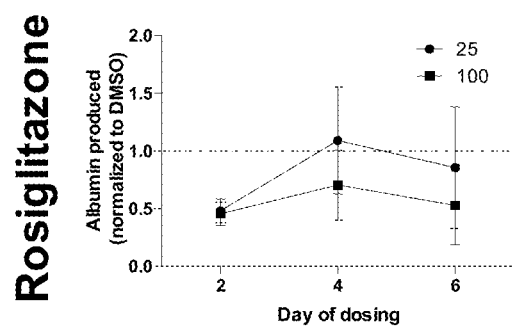
Figure 13S:
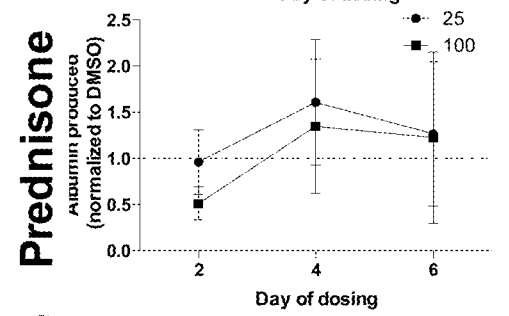
Figure 13T:
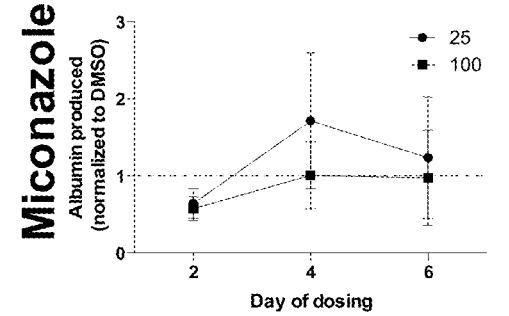
Figure 14K:
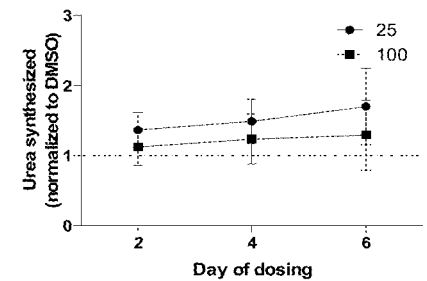
FIGS. 14K-14O depict graphs showing the amount of urea produced from co-cultures comprising hepatocytes and non-parenchymal cell populations continually cultured in culture medium comprising serum after co-cultures were treated with 25 nM or 100 nM of non-toxins aspirin (FIG. 14K), dexamethasone (FIG. 14L), rosiglitazone (FIG. 14M), prednisone (FIG. 14N) and miconazole (FIG. 14O), for 2, 4, and 6 days. Error bars are SD. All data was normalized to the vehicle, DMSO, control. Error bars are SD. All data was normalized to the vehicle, DMSO, control.
Figure 14L:
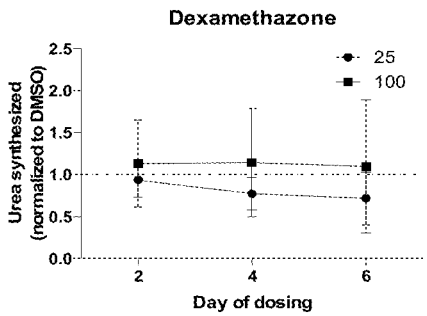
Figure 14M:
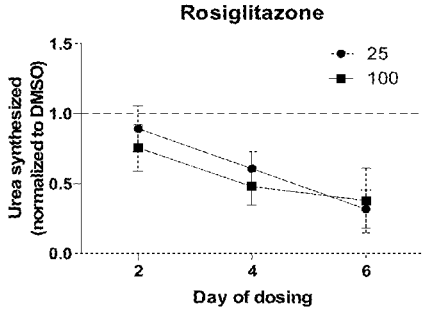
Figure 14N:
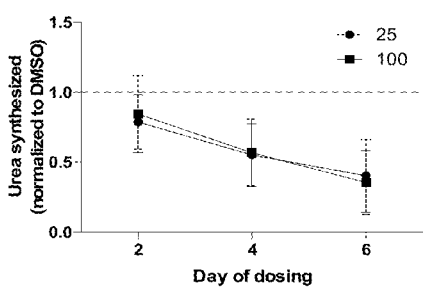
Figure 14O:
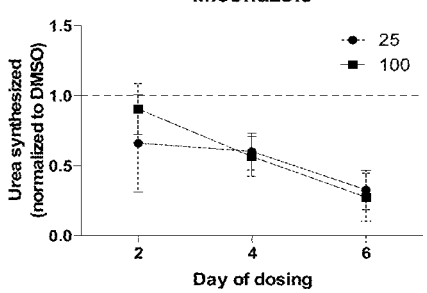
Figure 14P:
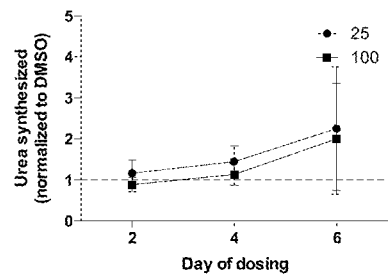
FIGS. 14P-14T depict graphs showing the amount of urea produced from co-cultures comprising hepatocytes and non-parenchymal cell populations periodically incubated in serum-free culture medium (starved) after co-cultures were treated with 25 nM or 100 nM of non-toxins aspirin (FIG. 14P), dexamethasone (FIG. 14Q), rosiglitazone (FIG. 14R), prednisone (FIG. 14S) and miconazole (FIG. 14T), for 2, 4, and 6 days. Error bars are SD. All data was normalized to the vehicle, DMSO, control. Error bars are SD. All data was normalized to the vehicle, DMSO, control.
Figure 14Q:
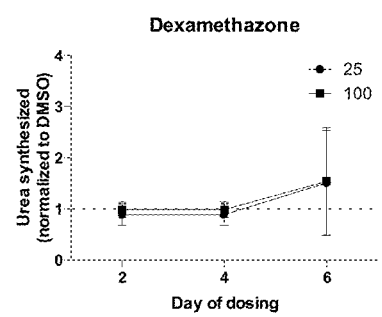
Figure 14R:
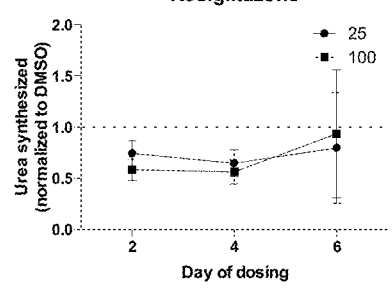
Figure 14S:
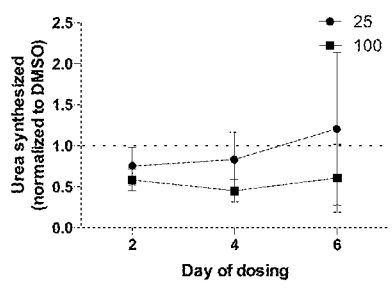
Figure 14T:
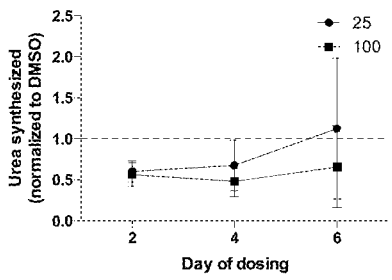

To assess starved and non-starved cultures specificity, cultures were treated with non-liver toxins at increasing concentrations of the Cmax. Specificity is defined as the ability of the system to correctly distinguish non-toxic compound from toxic compounds. This is calculated by dividing the number of compound identified as non-toxic by the total number of compounds tested. Rosiglitazone, prednisone, miconazole, dexamethazone and aspirin are considered non-liver toxins. The TC50 values for albumin production in non-starved cells treated with rosiglitazone (FIG. 12B and FIG. 13M), prednisone (FIG. 12B and FIG. 13N), miconazole (FIG. 12B and FIG. 13O), dexamethazone (FIG. 12B and FIG. 13L) and aspirin (FIG. 12B and FIG. 13K) were compared to the TC50 values for albumin production in starved cells treated with rosiglitazone (FIG. 12B and FIG. 13R), prednisone (FIG. 12B and FIG. 13S), miconazole (FIG. 12B and FIG. 13T), dexamethazone (FIG. 12B and FIG. 13Q) and aspirin (FIG. 12B and FIG. 13P) The TC50 values for urea production in non-starved cells treated with rosiglitazone (FIG. 12C and FIG. 14M), prednisone (FIG. 12C and FIG. 14N), miconazole (FIG. 12C and FIG. 14O), dexamethazone (FIG. 12C and FIG. 14L) and aspirin (FIG. 12C and FIG. 14K) were compared to the TC50 values for urea production in starved cells treated with rosiglitazone (FIG. 12C and FIG. 14R), prednisone (FIG. 12C and FIG. 14S), miconazole (FIG. 12C and FIG. 14T), dexamethazone (FIG. 12C and FIG. 14Q) and aspirin (FIG. 12C and FIG. 14P). Starved cultures did not identify any of the non-toxins as toxic even at the 100*Cmax dose (FIG. 13D and FIG. 14D), whereas non-starved cultures identified 3 of the 5 non-toxins as potentially toxic (FIG. 13C and FIG. 14C) (i.e.: albumin and urea levels fell below 50% of the control with increasing doses of the compound) (FIG. 12B). Specifically, rosiglitazone, prednisone and miconazole were all identified as toxic in non-starved cultures. This suggests that the specificity of starved cultures is 100%, while non-starved cultures have a specificity of 40%.

Example 10

To assess the potential utility of the starvation protocol to identify drug-drug interactions after prolonged culture, starved and non-starved MPCCs were treated with known enzyme inducers and then drug enzyme activity were assessed. Induction of CYP3A4, CYP1A2 and CYP2C9 was carried out with 2 treatments of phenobarbital, omeprazole, and rifampin, respectively, over 4 days in serum free medium, respectively. Enzyme induction was assessed by comparing the enzyme activity of cultures treated with either the inducer or the vehicle control (DMSO) after 4 days of treatment.

Figure 12F:
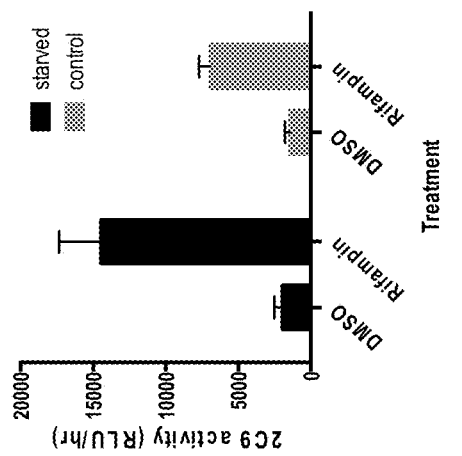
FIG. 12F depicts a graph showing the amount of CYP2C9 enzyme activity in co-cultures comprising hepatocytes wherein the composition is periodically incubated in serum-free culture (starved) medium and co-cultures comprising hepatocytes continually cultured in culture medium comprising serum (non-starved, control) after 4 weeks of culture in the presence of CYP2C9 inducers, DMSO or rifampin. Error bars represent SD.
Figure 12E:
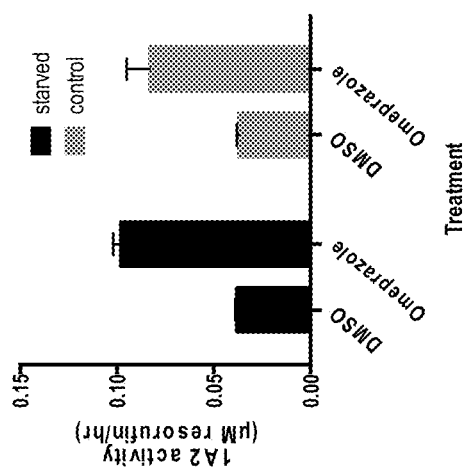
FIG. 12E depicts a graph showing the amount of CYP1A2 enzyme activity in co-cultures comprising hepatocytes wherein the composition is periodically incubated in serum-free culture (starved) medium and co-cultures comprising hepatocytes continually cultured in culture medium comprising serum (non-starved, control) after 4 weeks of culture in the presence of CYP1A2 inducers, DMSO or omeprazole. Error bars represent SD.
Figure 12D:
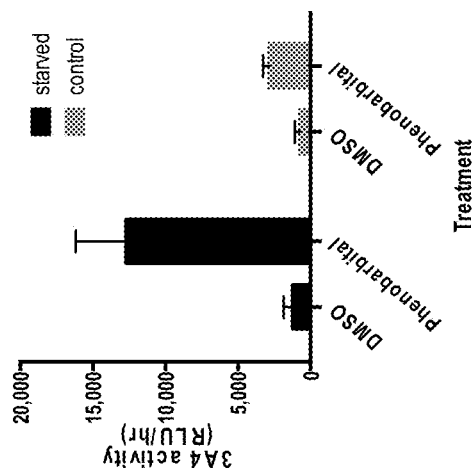
FIG. 12D depicts a graph showing the amount of CYP3A4 enzyme activity in co-cultures comprising hepatocytes wherein the composition is periodically incubated in serum-free culture (starved) medium and co-cultures comprising hepatocytes continually cultured in culture medium comprising serum (non-starved, control) after 4 weeks of culture in the presence of CYP3A4 inducers, DMSO or phenobarbital. Error bars represent SD.

Major differences in the level of enzyme induction were observed between starved and non-starved cultures. Non-starved culture CYP2C9 induction was 4.8 (±1.2) fold, while starved CYP2C9 induction was 7.3 (±2.5) fold (FIG. 12F). Non-starved culture CYP3A4 induction was 3.7 (±1.6) fold, while starved CYP3A4 induction was 10.2 (±5.8) fold (FIG. 12D). CYP1A2 induction was similar between starved, 2.6 (±0.12) fold, and non-starved cultures, 2.2 (±0.3) fold (FIG. 12E). These results suggest that periodic starvation prolongs the ability of hepatocytes to respond to enzyme inducers.

Example 11

To determine the optimum serum-free medium for the starvation protocol, MPCCs comprising hepatocytes were cultured in the following culture mediums: 1) a culture medium comprising serum (non-starved); 2) a serum-free culture medium (starved) that does not contain glucose or glucagon; 3) a serum-free culture medium (starved) that contains 2 nM glucagon but does not contain glucose; 4) a serum-free culture medium (starved) that contains 25 mM glucose (high glucose) but does not contain glucagon; and, 5) a serum-free culture medium (starved) that contains 25 mM glucose (high glucose) and 2 nM glucagon.

Figure 15A:
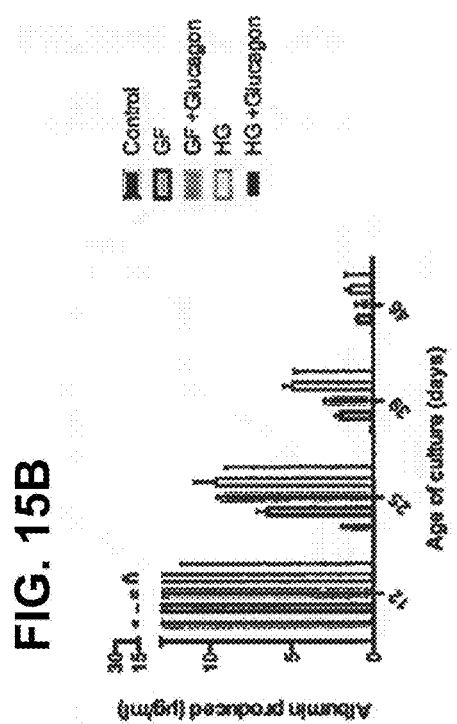
FIG. 15A depicts a graph showing the amount of urea produced in MPCCs comprising hepatocytes wherein: 1) the composition is in culture medium comprising serum (non-starved) after 12 days, 25 days, 39 days, and 46 days of culture (control); 2) the composition is periodically incubated in serum-free culture medium (starved) that does not contain glucose or glucagon after 12 days, 25 days, 39 days, and 46 days of culture (GF); 3) the composition is periodically incubated in serum-free culture medium (starved) that contains 2 nM glucagon but does not contain glucose after 12 days, 25 days, 39 days, and 46 days of culture (GF+Glucagon); 4) the composition is periodically incubated in serum-free culture medium (starved) that contains 25 mM glucose (high glucose) but does not contain glucagon after 12 days, 25 days, 39 days, and 46 days of culture (HG); and, 5) the composition is periodically incubated in serum-free culture medium (starved) that contains 25 mM glucose (high glucose) and 2 nM glucagon after 12 days, 25 days, 39 days, and 46 days of culture (HG+Glucagon). Error bars represent SD.
Figure 15B:
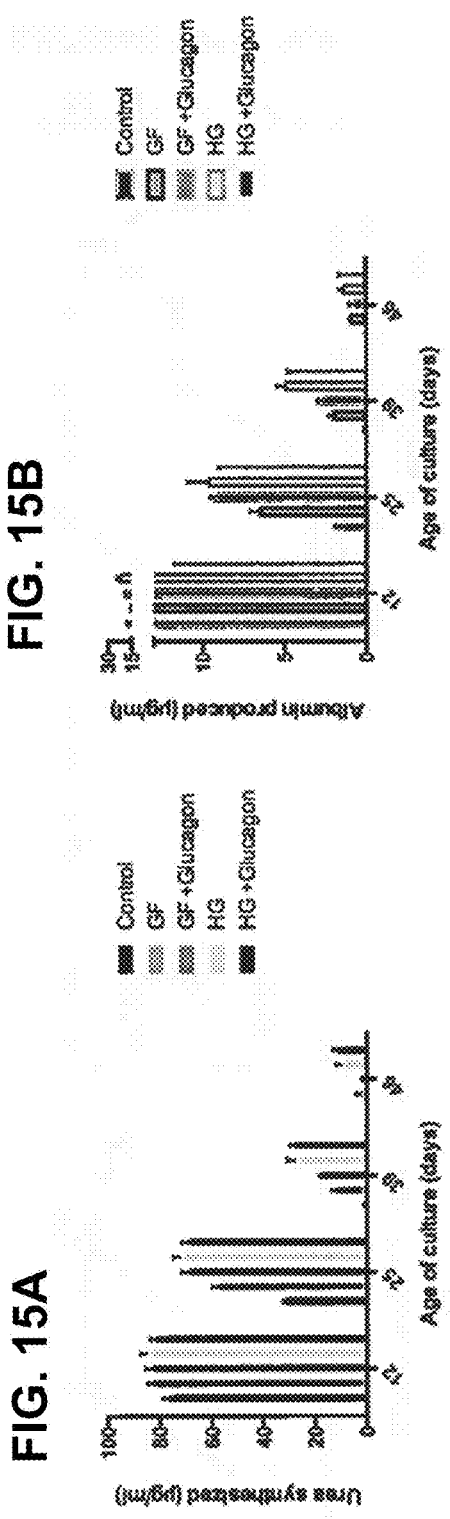
FIG. 15B depicts a graph showing the amount of albumin produced in MPCCs comprising hepatocytes wherein: 1) the composition is in culture medium comprising serum (non-starved) after 12 days, 25 days, 39 days, and 46 days of culture (control); 2) the composition is periodically incubated in serum-free culture medium (starved) that does not contain glucose or glucagon after 12 days, 25 days, 39 days, and 46 days of culture (GF); 3) the composition is periodically incubated in serum-free culture medium (starved) that contains 2 nM glucagon but does not contain glucose after 12 days, 25 days, 39 days, and 46 days of culture (GF+Glucagon); 4) the composition is periodically incubated in serum-free culture medium (starved) that contains 25 mM glucose (high glucose) but does not contain glucagon after 12 days, 25 days, 39 days, and 46 days of culture (HG); and, 5) the composition is periodically incubated in serum-free culture medium (starved) that contains 25 mM glucose (high glucose) and 2 nM glucagon after 12 days, 25 days, 39 days, and 46 days of culture (HG+Glucagon). Error bars represent SD.
Figure 15C:
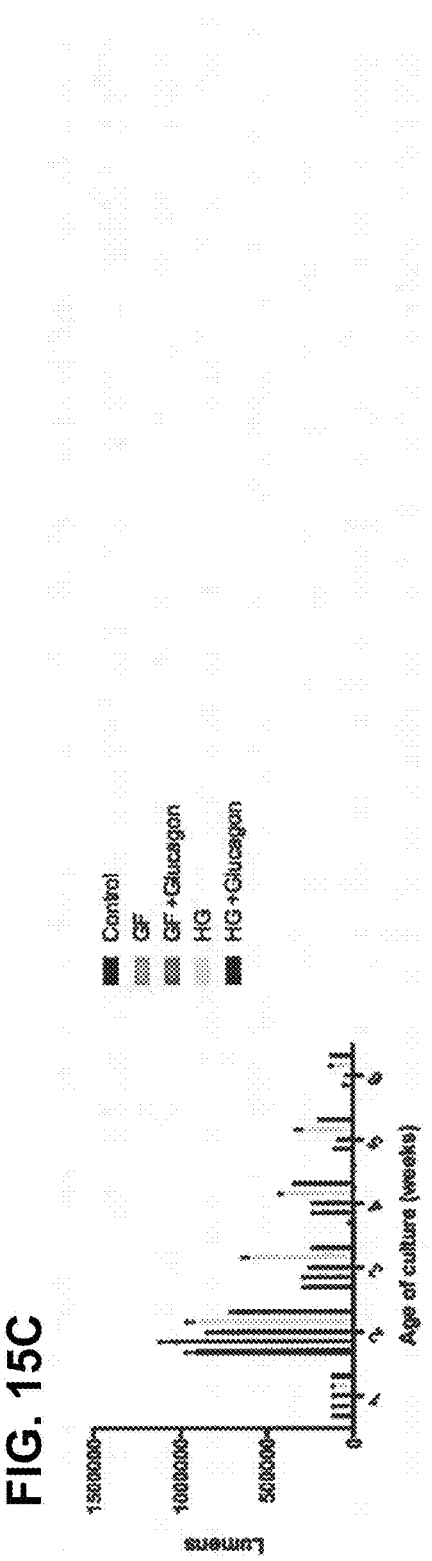
FIG. 15C depicts a graph showing the amount of CYP3A4 activity in MPCCs comprising hepatocytes wherein: 1) the composition is in culture medium comprising serum (non-starved) after 12 days, 25 days, 39 days, and 46 days of culture (control); 2) the composition is periodically incubated in serum-free culture medium (starved) that does not contain glucose or glucagon after 12 days, 25 days, 39 days, and 46 days of culture (GF); 3) the composition is periodically incubated in serum-free culture medium (starved) that contains 2 nM glucagon but does not contain glucose after 12 days, 25 days, 39 days, and 46 days of culture (GF+Glucagon); 4) the composition is periodically incubated in serum-free culture medium (starved) that contains 25 mM glucose (high glucose) but does not contain glucagon after 12 days, 25 days, 39 days, and 46 days of culture (HG); and, 5) the composition is periodically incubated in serum-free culture medium (starved) that contains 25 mM glucose (high glucose) and 2 nM glucagon after 12 days, 25 days, 39 days, and 46 days of culture (HG+Glucagon). Error bars represent SD.

Urea synthesis (FIG. 15A) and albumin production (FIG. 15B), markers of hepatic function, were measured in each of the MPCC cultured as described above at 12, 25, 39, and 46 days of culture. All MPCC cultures retained the ability to synthesis urea at 12 days; however, urea production in un-starved cells decreased after 25 days compared to the all serum-starved cells. Among the MPCCs cultured in the serum-free mediums, inclusion of glucose in the serum-free medium slightly improved hepatic function in the MPPC cultures over 6 weeks. An additional method of assessing hepatic activity, measuring CYP34A activity, was also performed and yielded similar results (FIG. 15C). Overall, inclusion of glucose in the serum-free culture media improved hepatic functions over several weeks as compared to a glucose-free, serum-free, culture media.

Discussion of Examples.

Hepatocytes are notoriously difficult to maintain in vitro using conventional methods, although recent advances have made it possible to prolong the lifetime of hepatocytes outside the body (Godoy et al., ARCH TOXICOL. 2013, 87(8):

1315). Successful efforts have taken inspiration from in vivo microenvironmental cues and physiological processes (Huh et al., TRENDS IN CELL BIOLOGY. 2011, 21(12): 745). One dynamic physiologic process that has not been investigated for its impact on hepatocyte longevity is nutrient and hormonal fluctuations. Here the potential benefits of mimicking the fasting and feeding cycles in the body on hepatocyte in vitro lifetime are addressed. A protocol was developed where cell culture medium components, specifically serum and hormones, are periodically removed to mimic some aspects of fasting and feeding in the liver, which we termed starvation (Diaz-Muñoz et al., COMP HEPATOL. 2010, 9:5). It was found that cyclic starvation every week had profound effects on hepatocytes ranging from morphologic stability to prolonged hepatocyte function.

The micropatterned co-culture (MPCC) platform was utilized which has been shown to sustain hepatocytes for at least 3 weeks in vitro for various applications (9). Importantly, hepatocytes in this system retain their ability to respond to hormones and nutrients, which is necessary to investigate the potential utility of dynamic culturing methods such as periodic starvations (Davidson and Khetani, SCI. REP. 2016, 6: 28178; Davidson et al., TISSUE ENGINEERING PART C: METHODS. 2015, 21(7), 716). Since the goal was to increase the functional lifetime of liver cells, the MPCC platform is a great system to assess this since liver cell secretions and hepatocyte colonies can be tracked over time to assess the loss of cells using simple phase contrast microscopy. Further, use of the MPCC system to address how starvation impacts liver cell lifetime allows modulation of those of hormones and serum to support long-term functions, which more accurately mimics a starved or fasted state. During fasting, nutrients and insulin levels decrease significantly and this can be easily mimicked by removing serum and insulin from the culture medium (Nelson and Halberg, J. NUTR. 1986, 116(11): 2244). Specifically, after 2 weeks of culture stabilization in maintenance medium, the cultures were washed with saline to remove excess nutrients, and then incubated MPCCs with a base medium lacking any serum or hormones.

Surprisingly, it was found that starvation drastically increased the lifetime and function of hepatocytes in our system. Even a one-hour starvation seemed to benefit hepatocyte functions, although a 2-day starvation period was found to be the optimal starvation time with respect to multiple hepatocyte functions. MPCCs that were periodically starved for 5 weeks had similar morphology and island size as 2-week old cultures. Accordingly, liver cell functions such as albumin and urea production were sustained at similar or higher levels to 2-week old cultures whereas non-starved culture function rapidly declined after 3 weeks of culture. Additionally, drug metabolism, which is notoriously difficult to retain in liver cells, was retained to at least 50% of the 2-week values in starved cultures after 5 weeks of culture, while non-starved cultures lost almost all drug metabolism capabilities by 5 weeks in culture. Since hepatocyte homotypic interactions (i.e. hepatocyte island integrity) was retained, we found a corresponding retention of hepatocyte transporter function in starved cultures, which was visualized with live cell imaging of a fluorescent transporter specific dye export, while this was mostly lost in non-starved cultures (Li et al., NAT. CELL BIOL. 2016, 18(3): 311).

Since altered feeding schedules, abnormal hormone levels and an abundance of nutrients are associated with altered liver function, without being bound to any one theory, it is believed that the periodic starvation prevents the buildup of toxins and metabolic related disease from occurring and prolongs hepatocyte lifetime in the disclosed cultures (Hatori et al., CELL METABOLISM. 2012, 15(6):848; Bailey et al., JOURNAL OF ENDOCRINOLOGY. 2014, 222(2):R7; Yamajuku et al., SCI. REP. 2012, 2:439; Diaz-Muñoz et al., COMP HEPATOL. 2010, 9:5). The maintenance of liver transporters observed should enable proper removal of toxins that build up in hepatocytes over time (Halilbasic et al., JOURNAL OF HEPATOLOGY. 2013, 58(1):155). Additionally, the retention of drug metabolism enzymes after starvation could allow for turnover of any toxic biologic compounds unknowingly present in cell culture medium. Lastly, hepatocytes accumulate less lipid droplets when exposed to the starvation protocol, which could limit the buildup of toxic lipids and prevent premature apoptosis (Feldstein et al., HEPATOLOGY. 2004, 40(1):185).

Periodic fasting is associated with increased lifetime in species ranging from yeast all the way up to rodents and humans, and has been classically attributed to the activation of the energy sensing enzyme adenosine monophosphate (AMP) activated kinase (AMPK) (Brandhorst et al., CELL METABOLISM. 2015, 22(1):86; Lee and Min, BMB REP. 2013, 46(4):181). It was found that the serum starvation protocol described above led to increased levels of activated AMPK (Ching et al., AMERICAN JOURNAL OF PHYSIOLOGY—CELL PHYSIOLOGY. 2010, 299(5):C1171). AMPK activation is also associated with increased hepatic nuclear receptor activation, transporters, and lipid turnover, which may explain why starved cultures had less lipid accumulation when compared to nonstarved cultures (Kulkarni et al., PHARM. RES. 2013, 30(9):2232). Interestingly, as disclosed above, it was found that the starvation protocol reduced the number of fibroblast numbers, either in pure fibroblast or MPCC, when compared to non-starved cultures. Taken together, the starvation protocol likely prolongs hepatocyte functions in co-cultures by activating AMPK and preventing overgrowth of supportive fibroblasts.

To mechanistically investigate this hypothesis, experiments were carried out where AMPK was artificially activated using a nontoxic AMPK activator, metformin, and prevented fibroblast overgrowth, by growth arresting the fibroblast population with mitomycin c, in place of starvation and it was assessed how these perturbations affect hepatocyte longevity and functions (Kim et al., DIABETES. 2007, 57(2):306). Metformin treatment or growth arresting fibroblasts in MPCCs significantly prolonged the functional lifetime of hepatocytes over an untreated control, although not to the same extent as the starvation protocol. The studies described above further suggest that the starvation protocol may prolong hepatocyte lifetime by activating AMPK and preventing fibroblast overgrowth, although other factors are clearly involved in prolonging longevity.

To appraise the potential impact of a longer functioning culture, the impact of starvation on hepatocyte drug toxicity screening capabilities was assessed and potential drug-drug interactions via enzyme induction identified. MPCCs have been rigorously tested and successfully utilized for the aforementioned applications, although this utility has not been characterized at later time points (i.e. >3 weeks) (Khetani and Bhatia, NAT BIOTECHNOL. 2017, 26(1):120; Khetani et al., TOXICOLOGICAL SCIENCES. 2013, 132(1):107). MPCCs were fabricated in 96 well plates for drug toxicity screens and the starvation protocol worked equally well in this format. After 4 weeks in culture, as discussed above, it has been found that without starvation MPCCs could still identify hepatotoxins with 100% accuracy and showed significant enzyme induction. Although non-starved MPCCs incorrectly identified 3 out of the 5 non-liver toxins as toxic and also had much lower levels of induction when compared to starved cultures. Importantly, starved cultures correctly identified all toxic and non-toxic compounds at the drug concentrations tested. The results from these screening studies highlight the overall benefit of periodic starvation and suggest that it could be an essential component for the maintenance of proper function of engineered tissues in drug toxicity studies, which are highly needed (Paul et al., NAT. REVIEWS DRUG DISCOVERY. 2010, 9(3):203).

Importantly, the disclosures above show that starvation not only prolongs hepatocyte lifetime, but it also improves overall cell health to help give proper responses for important applications such as distinguishing toxic drugs accurately.

Methods for Examples.

(a) Cell Culture and MPCC Fabrication

MPCCs were fabricated using the same methods previously described in Davidson et al., TISSUE ENGINEERING PART C: METHODS. 2015, 21(7):716, the disclosure of which is herein incorporated by reference in its entirety. Briefly, type I rat tail collagen was first coated on tissue culture polystyrene plates and then patterned into circular domains using soft lithographic techniques and plasma ablation. Next primary human hepatocytes were seeded into patterned tissue culture wells and allowed to adhere to the collagen domains. To create co-cultures, supportive 3T3-J2 fibroblasts were seeded 18-24 hours after seeding hepatocytes. In specified experiments within this study, growth arrested fibroblasts were used in place of non-growth arrested fibroblasts. For growth arrested fibroblast cultures, fibroblasts were cultured until they reached 90% confluency and the treated with mitomycin C the day of seeding with micropatterned hepatocytes. Specifically, cultures were first washed with 1×PBS, to removed residual medium, and then incubated with 1 µg/ml mitomycin C in fibroblast maintenance medium (10% bovine serum, 1% penicillin/streptomycin, and high glucose DMEM) for ~4 hours in the cell culture incubator. Mitomycin C containing medium was then removed and replaced with fibroblast maintenance medium for at least 30 minutes prior to splitting and seeding fibroblasts into cultures containing patterned hepatocytes.

Pure hepatocyte cultures were created as previously described (20). Briefly, Type I rat tail collagen was diluted in molecular grade water to achieve a final concentration of 100 µg/ml and added to tissue culture polystyrene plates and incubated for 2 hours at 37° C. Coated wells were washed with water twice and dried prior to seeding primary human hepatocytes. Hepatocytes were seeded at a density of 1.16 million cells/mL, and cultures were switched to their respective conditions after seeding for 4 hours.

(b) Starvation Protocol and Experimental Timeline

Once MPCCs were fabricated, they were cultured in 5 mM glucose containing maintenance medium for 2 weeks. Cultures were treated with various starvation treatments, 1 hour, 1 day, 2 day and 3 days. To start the starvation, cultures were washed once with 1×PBS, and then incubated in 5 mM glucose containing serum free medium for the specified time. This medium was also supplemented with 1% penicillin/streptomycin and 1.5% HEPES buffer. After the starvation period, cultures were then placed back in maintenance medium for 5-8 days, depending on the previous starvation period. This was continued for 4 weeks, including the initial starvation. To mimic starvation, we treated cultures with metformin, which activates AMPK, at a concentration of 250 µM in hepatocyte maintenance medium during the same period, 2 days, where cultures were starved.

For pure culture studies, hepatocytes were switched to hepatocyte maintenance medium after 4 hours of seeding. Cultures were starved 2 days later and every 2 days after that for a total of 14 days of culture. This shorter serum starvation protocol was used because of the shorter lifetime of pure hepatocyte cultures compared to co-cultured hepatocyte systems.

(c) Biochemical Assays

Biochemical assays (albumin production, urea synthesis) and enzyme activity assays (CYP2A6, CYP3A4 and CYP1A2) were carried out as previously described in Davidson et al., SCI. REP. 2016; 6:28178, the disclosure of which is herein incorporated by reference in its entirety. Additionally, CYP2C9 enzyme activity was assessed in these studies and this was carried out by incubating cultures with the CYP2C9 specific substrate Luciferin-H for 3 hours in serum free/phenol red free medium. Culture medium was collected after this incubation period and analyzed according to manufacturer protocols (Promega, Madison, Wis.).

(d) Live Cell Imaging, Staining and Image Analysis

Hepatocyte island morphology was monitored over time using phase contrast imaging. Additionally, we assessed bile canaliculi over time using CDCFDA fluorescent staining and Hoechst 33342 to visualize cell nuclei. Specifically, cultures were washed 1 time with serum free medium containing 5 mM glucose, 1% penicillin/streptomycin and 1.5% HEPES buffer and glucose free DMEM containing 4 mM supplemented L-glutamine. CDCFDA and Hoechst 33342 were added to this same serum free culture medium at a concentration of 2 µM and 1 µM, respectively, immediately before treating cultures, and then cultures were treated for 15 minutes in the cell culture incubator. This staining medium was then removed and cultures were washed 3 times with serum free medium, and the third wash was left in the culture dish. Cultures were then imaged using the EVOS FL microscope, where the CDCFDA (bile) stain was imaged using the GFP light cube, and the nuclear stain was imaged using the DAPI light cube. Analysis of hepatocyte island area and solidity was carried out in FIJI by outlining phase contrast images of hepatocyte islands and using the shape descriptors feature in the analysis as described in Schneider et al., NAT METHODS. 2012; 9:671-675, the disclosure of which is herein incorporated by reference in its entirety. The area of excreted CFDA (bile canaliculi), was assessed by setting a threshold that included all fluorescent signal and quantifying the threshold area/ island.

(e) Drug Screening and Enzyme Induction

To assess drug toxicity, cultures were incubated with increasing multiples of the specific drug's Cmax, the average maximal concentration the drug reaches in patient's blood after administration. Specifically, compounds were first dissolved in DMSO at 100,000 times their Cmax, and then added to serum free culture medium (containing 5 mM glucose, 1% ITS+ (Corning) 1% penicillin/streptomycin and 1.5% HEPES buffer, 100 nM dexamethasone, 2 nM glucagon and glucose free DMEM containing 4 mM supplemented L-glutamine) at a concentration of 25*Cmax or 100*Cmax. By diluting compounds at 100,000*Cmax, we could maintain a concentration of 0.1% w/v DMSO in the culture medium. Accordingly, 0.1% DMSO was used as the vehicle control for these studies. Cultures were treated 3 times with compounds, every 2 days, for a total of 6 days of treatment.

For enzyme induction, cultures were treated with prototypical enzyme inducers (rifampin for CYP2C9, phenobarbital for CYP3A4 and omeprazole for CYP1A2) or their vehicle control, over 4 days, which consisted of 2 treatments every 2 days. Specifically, rifampin, phenobarbital, and omeprazole or the vehicle control were added to the same medium used for drug toxicity screening at a concentration of 25 µM, 1 mM, and 10 µM. Enzyme induction was assessed by first incubating induced or vehicle treated control cultures with respective enzyme specific substrates and then secondly quantifying the amount of substrate turnover that occurred over 1-3 hours, depending on the specific enzyme tested.

(f) Statistical Analyses

Each experiment was carried out in three or more wells for each condition. Two to three cryopreserved PHH donors were used to confirm observed trends. Microsoft Excel and GraphPad Prism 5.0 (La Jolla, Calif.) were used for data analysis and plotting data. Statistical significance of the data was determined in representative experiments using the Student's t-test or one-way ANOVA with Dunnett's multiple comparison tests for post hoc analysis.

What is claimed is:

1. A method of culturing a population of hepatocytes in vitro, comprising:
   (1) seeding the population of hepatocytes in a micropattern on a culture substrate,
   wherein the micropattern comprises a predetermined two-dimensional pattern of multiple microdots, the micropattern defined by a microdot diameter and a center-to-center spacing between each of any two neighboring microdots, and the microdots comprise the hepatocytes;
   (2) incubating the population of hepatocytes for at least 18 hours;
   (3) seeding the population of hepatocytes that has incubated for at least 18 hours with at least one non-parenchymal cell population, wherein the space between the microdots comprises the non-parenchymal cell population to achieve a co-culture;
   (4) incubating the co-culture in a maintenance culture medium for a time period of about 8 days to about 6 weeks before the composition is incubated in a serum-free culture medium, wherein the maintenance culture medium comprises serum; and
   (5) incubating the co-culture in a serum-free culture medium for a time period of about 2 hours to about 6 weeks, wherein the serum-free culture medium does not comprise serum,
   (6) alternating steps (4) and (5) at least twice.

2. The method according to claim 1, wherein each microdot has a diameter of about 500 µm and the center-to-center spacing between each of any two neighboring microdots is about 1200 µm.

3. The method according to claim 1, wherein the co-culture is incubated in maintenance culture medium for at least one time period of at least 2 weeks before the composition is incubated in serum-free culture medium.

4. The method according to claim 1, wherein the composition is incubated in serum-free culture medium for at least one time period of about 2 hours to about 3 days.

5. The method according to claim 4, wherein the co-culture is incubated serum-free culture medium for at least one time period of about 2 days.

6. The method according to claim 1, wherein the composition is
   (a) incubated in maintenance culture medium for a time period of about 8 days, and
   (b) incubated in serum-free culture medium for a time period of about 2 hours to about 3 days,
   wherein (a) and (b) are alternated at least twice.

7. The method according to claim 1, wherein said composition exhibits at least one indicator of hepatocyte function at least 4 weeks in culture.

8. The method according to claim 1, wherein said co-culture exhibits at least one indicator of hepatocyte function at least 6 weeks in culture.

9. The method according to claim 7, wherein said at least one indicator of hepatocyte function is selected from albumin production, urea production, ATP production, glutathione production, enzyme activity, lipid accumulation, liver gene expression, liver protein expression, or CYP2C9 activity, CYP3A4 activity, CYP1A1 activity, CYP1A2 activity, CYP2B6 activity, CYP2A6 activity, CYP2D6 activity, CYP2C8 activity, CYP2C19 activity, or CYP2E1 activity.

10. The method according to claim 1, wherein said composition retains hepatocyte morphology at least 4 weeks in culture.

11. The method according to claim 10, wherein said co-culture retains hepatocyte morphology at least 6 weeks in culture.

12. The method according to claim 1, wherein the serum-free culture medium comprises glucose.

13. The method according to claim 12, wherein the serum-free culture medium comprises glucagon.

14. The method according to claim 1, wherein the hepatocytes are human hepatocytes.

15. The method according to claim 1, wherein at least one of the non-parenchymal cell populations comprises non-human stromal cells selected from the group consisting of fibroblasts, fibroblast-derived cells, macrophages, endothelial cells, stellate cells, pericytes, inflammatory cells, cholangiocytes and other types of stromal cells, and combinations thereof.

16. The method according to claim 15, wherein the stromal cells comprise 3T3-J2 murine embryonic fibroblasts.

17. The method according to claim 15, wherein the stromal cells are growth arrested.

* * * * *